United States Patent
Álvarez González et al.

(10) Patent No.: US 11,998,643 B2
(45) Date of Patent: Jun. 4, 2024

(54) NANOSTRUCTURE LIPID SYSTEM

(71) Applicants: UNIVERSIDADE DE SANTIAGO DE COMPOSTELA, Santiago de Compostela (ES); FUNDACIÓN INSTITUTO DE INVESTIGACIÓN SANITARIA DE SANTIAGO DE COMPOSTELA (FIDIS), Santiago de Compostela (ES); SERVIZO GALEGO DE SAÚDE, Santiago de Compostela (ES)

(72) Inventors: José Víctor Álvarez González, Santiago de Compostela (ES); Francisco Javier Otero Espinar, Santiago de Compostela (ES); Mª Luz Couce Pico, Santiago de Compostela (ES); Asteria Luzardo Álvarez, Lugo (ES); Cristobal Colón Mejeras, Santiago de Compostela (ES); MªRosaura Leis Trabazo, Santiago de Compostela (ES)

(73) Assignees: UNIVERSIDADE DE SANTIAGO DE COMPOSTELA, Santiago de Compostela (ES); SERVIZO GALEGO DE SAÚDE, Santiago de Compostela (ES); FUNDACIÓN INSTITUTO DE INVESTIGACIÓN SANITARIA DE SANTIAGO DE COMPOSTELA (FIDIS), Santiago de Compostela (ES)

( * ) Notice: Subject to any disclaimer, the term of this patent is extended or adjusted under 35 U.S.C. 154(b) by 320 days.

(21) Appl. No.: 17/259,110

(22) PCT Filed: Jul. 10, 2019

(86) PCT No.: PCT/EP2019/068629
§ 371 (c)(1),
(2) Date: Jan. 8, 2021

(87) PCT Pub. No.: WO2020/011896
PCT Pub. Date: Jan. 16, 2020

(65) Prior Publication Data
US 2021/0322328 A1 Oct. 21, 2021

(30) Foreign Application Priority Data
Jul. 10, 2018 (EP) .................................. 18382513

(51) Int. Cl.
| | |
|---|---|
| *A61K 9/50* | (2006.01) |
| *A61K 38/46* | (2006.01) |
| *A61K 38/47* | (2006.01) |
| *A61K 38/48* | (2006.01) |
| *A61K 47/10* | (2017.01) |
| *A61K 47/22* | (2006.01) |
| *A61K 47/24* | (2006.01) |
| *A61P 3/00* | (2006.01) |
| *A61P 19/04* | (2006.01) |

(52) U.S. Cl.
CPC .......... *A61K 9/5073* (2013.01); *A61K 9/5015* (2013.01); *A61K 9/5031* (2013.01); *A61K 9/5089* (2013.01); *A61K 38/465* (2013.01); *A61K 38/47* (2013.01); *A61K 38/482* (2013.01); *A61K 47/10* (2013.01); *A61K 47/22* (2013.01); *A61K 47/24* (2013.01); *A61P 3/00* (2018.01); *A61P 19/04* (2018.01)

(58) Field of Classification Search
CPC .......... A61P 19/04; A61P 3/00; A61K 9/5073; A61K 9/5015; A61K 9/5031; A61K 9/5089; A61K 38/465; A61K 38/47; A61K 38/482; A61K 47/10; A61K 47/22; A61K 47/24
See application file for complete search history.

(56) References Cited

U.S. PATENT DOCUMENTS

| | | | |
|---|---|---|---|
| 4,214,046 A | 12/1980 | Papahadjopoulos et al. | |
| 4,241,046 A * | 12/1980 | Papahadjopoulos ... | A01N 25/28 424/420 |
| 5,656,289 A * | 8/1997 | Cho ..................... | A61K 9/1275 424/463 |
| 5,665,700 A * | 9/1997 | Cho ....................... | A61K 38/28 514/937 |
| 11,230,694 B2 | 1/2022 | Martínez Lamas et al. | |
| 2020/0064358 A1 | 2/2020 | González Juanatey et al. | |
| 2020/0173997 A1 | 6/2020 | Cubiella Fernández et al. | |
| 2020/0191789 A1 | 6/2020 | Piñeiro Ces et al. | |

(Continued)

FOREIGN PATENT DOCUMENTS

| | | | | |
|---|---|---|---|---|
| CN | 102106821 | * | 6/2011 | ............. A61K 9/127 |
| EP | 2 317 968 A2 | | 5/2011 | |

(Continued)

OTHER PUBLICATIONS

CN102106821 Machine Translation (Year: 2011).*

(Continued)

*Primary Examiner* — Sean M Basquill
(74) *Attorney, Agent, or Firm* — Seed IP Law Group LLP

(57) ABSTRACT

The present invention is related to systems of administration of enzymes or other proteins, preferably for use in enzyme replacement therapy (ERT), in particular for the treatment of Lysosomal diseases. In particular, the invention encompasses the preparation of a composition based on nanostructured lipid systems and its use in the manufacture of a therapeutic product.

13 Claims, 32 Drawing Sheets

(56) References Cited

U.S. PATENT DOCUMENTS

| | | |
|---|---|---|
| 2020/0393461 A1 | 12/2020 | Pego Reigosa et al. |
| 2021/0275680 A1 | 9/2021 | De La Fuente Freire et al. |
| 2021/0275687 A1 | 9/2021 | De La Fuente Freire et al. |

FOREIGN PATENT DOCUMENTS

| | | | |
|---|---|---|---|
| WO | 03/030865 A1 | 4/2003 | |
| WO | WO-03030865 A1 * | 4/2003 | ............. A61K 38/28 |

OTHER PUBLICATIONS

Rui Yang, et al., Preparation of Gel-Core-Solid Lipid Nanoparticle: A Novel Way to Improve the Encapsulation of Protein and Peptide, 58 Chem. Pharm. Bull. 1195 (Year: 2010).*

Antonia J Almeida & Eliana Souto, Solid Lipid Nanopaticles as a Drug Delivery System for Peptides and Proteins, 59 Adv. Drug Del. Rev. 478 (Year: 2007).*

Divyesh H Shastri, Effective Delivery Routes and Strategies for Solid Lipid Nanoparticles (SLN) and Nanostructured Lipid Carriers (NLC), 23 Curr. Pharma. Des. 6592 (Year: 2017).*

Shevchenko et al., "Mass Spectrometric Sequencing of Proteins from Silver-Stained Polyacrylamide Gels," *Analytical Chemistry* 68(5):850-858, Mar. 1, 1996.

Shilov et al., "The Paragon Algorithm, a Next Generation Search Engine That Uses Sequence Temperature Values and Feature Probabilities to Identify Peptides from Tandem Mass Spectra," *Molecular & Cellular Proteomics 6.9*:1638-1655, May 2007.

* cited by examiner

A)

B)

C)

A)

B)

C)

D)

NANOSTRUCTURE LIPID SYSTEM

FIELD OF THE INVENTION

The present invention is related to systems of administration of enzymes or other proteins, preferably for use in enzyme replacement therapy (ERT), in particular for the treatment of Lysosomal diseases. In particular, the invention encompasses the preparation of a composition based on nanostructured lipid systems and its use in the manufacture of a therapeutic product.

BACKGROUND OF THE INVENTION

Lysosomal Storage Diseases are a group of approximately 70 hereditary disorders associated with deficiencies in the lysosomal enzymes and still is a serious medical, social and health problem. They are caused by the deficit of intralysosomals specific enzymes or enzymes involved in the transport of proteins from the nucleus to the cytoplasm, responsible for the acidic hydrolysis of macromolecules within the lysosomes. This enzymatic deficiency produces a progressive accumulation of the substrate of the enzyme at the cellular level in different tissues of the body, which leads to a chronic and multi-organic disease. There are different types of lysosomal diseases depending of the macromolecules that accumulate at the intracellular level.

The treatment of lysosomal diseases, has been improved in recent years due to the development of enzyme replacement therapies (ERT). Currently, there are a few recombinant enzymes that can be used in ERTs for various diseases. Lysosomal diseases that are treated with enzyme replacement include:

MPS I (Hurler disease, disease Hurler-Scheie, Scheie disease), whose treatment is the Laronidase [Aldurazyme®].

MPS-II (Hunter's disease) that is treated with idursulfase [Elaprase®].

MPS IV-(A Morquio disease) dealing with the elosulfase alfa.

MPS VI (Maroteaux-Lamy syndrome) whose treatment is Galsulfasa [Naglazyme®].

MPS VII (Sly syndrome) whose treatment is alfa vestronidasa [Mepsevii®].

Gaucher disease treated with imiglucerase [Cerezyme®] or Velaglucerase alfa (Vpriv)®).

Fabry disease treated with agalsidase beta [Fabrazyme®] or agalsidase alfa [Replagar].

Pompe disease treated with Alglucosidasa alfa [Myozyme®].

Batten disease whose treatment is alfa cerliponasa [Brinuera®].

Wolman disease whose treatment is alfa sebelipasa [Kanura®]

Alpha-mannosidosis treated with velmanasa [Lamzede®].

Most of the drugs used in ERT are formulated as a dispersion solution of the enzyme in an isotonic and sterile environment to be administering by intravenous route to the patients and provide the proteins that patients are unable to synthesize by themselves. This system has the disadvantage that to achieve effective concentrations at the lysosomal level, it is necessary to infuse high enzyme concentrations solutions slowly, for at least 3-4 hours to ensure the enzyme accumulation in the interior of the lysosomes. The treatment should be repeated in relatively short periods of time (e.g. weekly) due to inefficient biodistribution of these proteins and its rapid biodegradation and elimination. To ensure its lysosome accumulation, enzymes must be modified including specific ligands of membrane transporter which mediate the internalization and accumulation of proteins in lysosomes. Nevertheless, its use is associated with some adverse effects. Most of the ERT based-treatments can produce during this administration or in the subsequent hours of treatment, disorders related to hypersensitivity and anaphylactic reactions caused by the high levels of the enzyme in the bloodstream. As in others enzymatic therapies, the patients develop antibodies of IgG type over time, which is related to immunological problems. In addition, enzymes have relatively high plasma clearance with small plasmatic half-life which causes the rapid elimination once the administration is interrupted. This fact means that administration must be repeated during relatively short periods of time. Due to the special weakness conditions in lysosomal storage diseases patients any side effect can become very a matter of importance. Thus, it is crucial to perform the enzyme administration under strict conditions. Although it is possible to administer the enzyme in the patient's home with nurse displaced in some enzyme replacement therapies, the importance of the side effects associated with treatment strongly have limited this possibility.

Therefore, the current lysosomal diseases ERT treatments consists of intravenous administration of the deficient enzyme by continuous infusion in order to reach the intracellular levels required for eliminating the material deposits. However, to reach therapeutic enzyme concentration inside the cells, it is necessary to prolong the administration of high concentrated enzyme solutions during extended periods of time. The use of these high concentrations promotes the appearance of awareness problems which seriously limits this type of treatment. Additionally, some Lysosomal Storage Diseases (MPSI, MPSII, MPSIII A and B, Metachromatic Leukodystrophy or neuronal ceroid lipofuscinoses (ncls)) have associated an important neurological component due to the fact that to get the efficacy of the treatment is necessary that the enzyme reaches the central nervous system. Since enzymes are unable to cross the brain barrier and this goal is not achieved by intravenous infusion in this case is necessary to use intrathecal or intracerebroventricular administration. To facilitate the administration is possible to implant an infuser or pump door in the patients.

For these reasons and to avoid these issues it is necessary to develop new strategies to protect the enzyme and to optimize the enzyme drug delivery systems. The present invention was developed with this goal.

BRIEF DESCRIPTION OF THE INVENTION

The present invention provides a pharmaceutical nanostructured lipid system (hereafter referred to as: "nanostructured lipid system of invention" or "composition of the invention"), preferably for use in ERT, as a vehicle for transporting enzymes or other proteins, which allows improving distribution, stability and availability of the protein at the cellular level, allowing the protein release during longer periods of times and reaching important target tissues, such as brain tissue, skeletal muscle, bone and cartilage. In the concrete case of ERT, the composition of the invention increases the plasmatic enzyme stability promoting the intracellular internalization of the Lipid System Nanostructured carrier at the lysosomal levels where it progressively releases the enzyme.

DETAILED DESCRIPTION OF THE INVENTION

Figure 1:
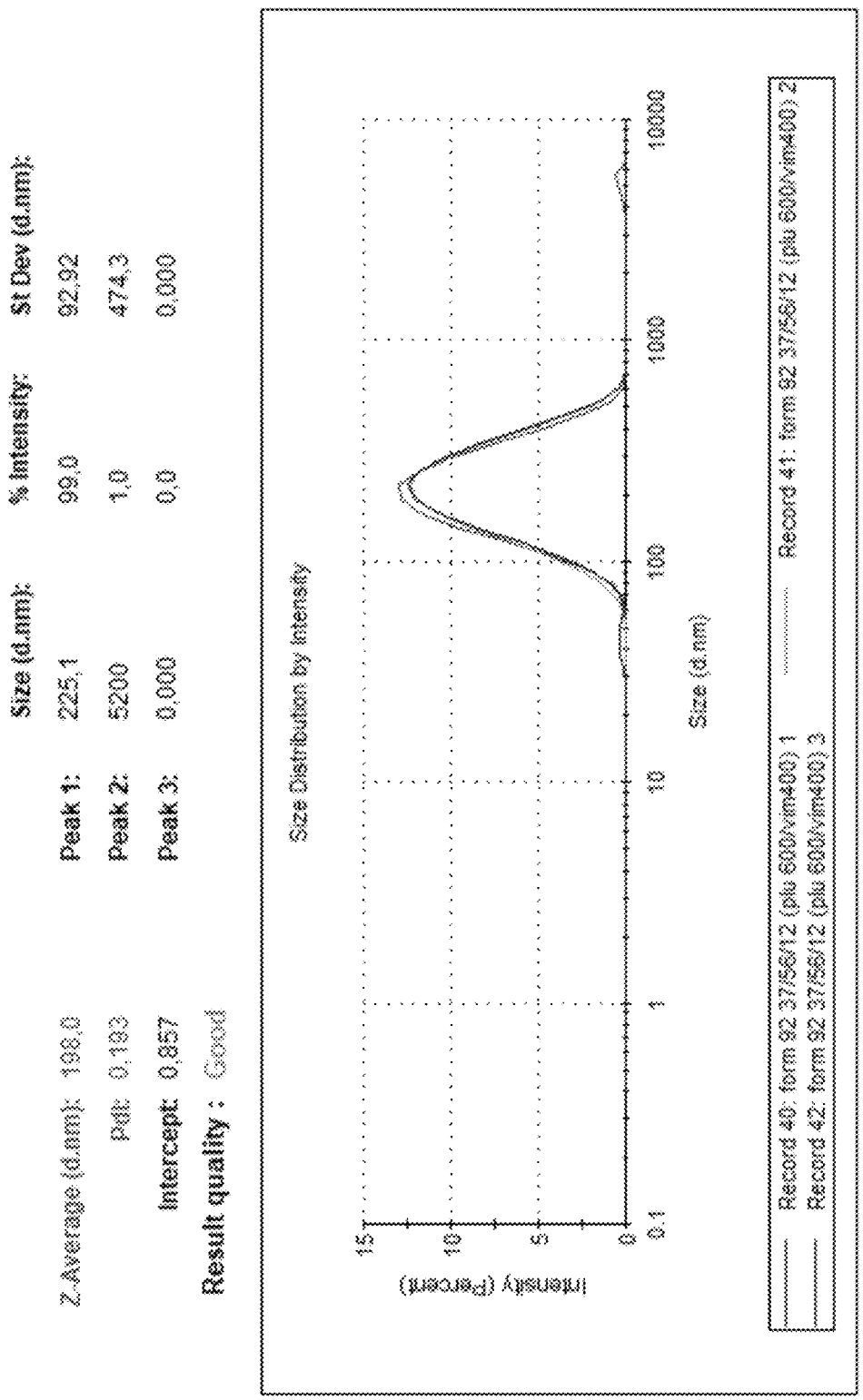
FIG. 1 Example of the size distribution of the nanostructured lipid carriers (NLC), determined by DLS.

The current treatment of lysosomal diseases consists of the intravenous administration by continuous infusion of the deficient enzyme in order to reach the intracellular levels required to remove accumulated deposits of material. However, due to their protein nature, enzymes are deficiently distributed inside cell tissues. Therefore, the repeated infusion of a high concentrated enzyme solution is required. The use of these concentrations promotes sensitization problems which restrict this type of treatment. In addition, it is not possible to achieve effective concentrations at the level of the central nervous system through the intravenous administration, thus it is required to replace the enzyme administration by the intrathecal or intracerebroventricular administration.

The present invention thus provides a pharmaceutical nanostructured lipid system, preferably to be used in ERT, as a vehicle to carry enzymes or other proteins and which allows improving its distribution, stability and availability at the cellular level, also enabling the protein release during longer periods of times, reaching a better distribution in target tissues, such as brain tissue, skeletal muscle, bone and cartilage. The composition of the invention increases the plasma stability of proteins, preferably enzymes, and promotes its internalization at the cellular level through the intracellular internalization in the lysosomal system of the lipid nanostructured carrier with the immobilized enzyme that is progressively released at this level.

Specifically, the composition of the invention is a pharmaceutical composition comprising the NLC (nanostructured lipid system), wherein the NLC comprises:
  (i) One or several lysosomal enzymes or proteins with activity on cellular metabolism such as infliximab, abatacerpt, rituximab, adalidumab, etanercept, golimumab, certolizumab, sifalimumab, anifrolumab or similar proteins. The lysosomal enzymes incorporated in the formulation would be any of those employed in the treatment of lysosomal diseases or similar deficits, such as elosulfase alfa, laronidase, idursulfase, galsulfase, imiglucerase, agalsidase, alglucosidase or N-acetyl glucosaminidase. Proteins would be immobilized on the gelled core (ii) or adsorbed on the surface (v);
  (ii) An aqueous core that is preferably gelled. The core is made of a solution, dissolution or dispersion of aqueous nature which may include: water, buffer solution of pH, salts, as well as a temperature responsive polymer that gels in function of the temperature or Ionic concentration: i.e. Poloxamer 407 (note that the denomination Poloxamer includes polymers tri-block with a central hydrophobic polypropylene oxide chain and two side chains of polyoxyethylene in different proportions. Example: P407 is made of a chain of polyoxypropylene 4000 Da and a 70% polyoxyethylene content); In addition to the Poloxamer 407, other possible gelling agents useful in the present invention can be selected from the list consisting of: Chitosan, hydroxypropyl cellulose (HPC), hidroxipropilmetil cellulose (HPMC) and di-block copolymer of polyethylene glycol and polylactic acid (PEG-PLGA-PEG);
  (iii) A lipid layer coating the aqueous core made of mixtures of solid and liquid lipids. Solid lipids such as long-chain fatty acids and its esters, such as stearic acid, palmitic acid, behenic, arachidonic palmitic-stearate of glyceryl, dibehenate of glyceryl cetyl-palmitate, of glyceryl trimiristin, tripalmitin tristearate; phospholipids such as phosphoglycerides and sphingolipids; acids and salts bile such as taurocholate, deoxicholate, glycocholate, hiodeoxycholate, litocholate and similar. Liquid lipids such as: media and short chain fatty acids and their esters, as valeric acid, caproic, caprylic, capric, lauric, pelargonic, enantic, as well as triglyceride of caproic acid, capric caprylic, or lauroyl-polyoxyglicerides; tocopherol or other derivatives of vitamin E; as well as natural oils of vegetable origin or animal as olive, corn, sesame, cotton, soybean, sunflower, coconut, or cod liver oil;

(iv) Surfactants and stabilizers. Surfactants and stabilizers like lecitins (eg. Soy, egg, corn, sunflower . . . ), poloxamers (188, 407), esters of polyethylene glycol or polyethylene (macrogolhydroxystearates, stearate polyethylene . . . ), polyoxyethylene castor oil, and esters of polysorbate with fatty acids (polysorbate 20, 65, 40, 60, 80); and (v) Surface modifying agents to avoid the opsonization of the NLC and modify the biodistribution. They include PEGylate agents as the polyethylene glycols of various molecular weights, substituted derivatives of vitamin D as tocopherol-succinate-PEG 1000 or hydrophilic colloids such as the polivinilalcohol hydrophilic polymers, polysaccharides such as chitosan, pectins . . . , or peptides.

The nanostructured lipid system of the present invention may be prepared according to the following protocol: in a first stage A, an aqueous solution, dissolution or dispersion that includes a thermogeling polymer as Poloxamer 407 or a temperature responsive polymer and optionally comprises one or several lysosomal enzymes or other proteins is added to an oily phase comprising a mixture of solid lipids and fluids and solvents, so a top layer (oily phase) and a bottom layer (aqueous phase) is formed; It is important to clarify that once the emulsion is formed the aqueous solution or dispersion constitutes the dispersed phase and the mixture of solid lipids and fluids with solvents, the continuous or dispersing phase. (B) in a second stage, a primary emulsion will be formed; this emulsion can be produced for example by using ultrasonic homogenization. (C) once the primary emulsion is formed, the dispersed phase (formed by droplets from the aqueous solution or dispersion) is chemically change to particles or droplets of gel as there is an increase of the temperature or Ionic concentration. (D) to the gel in oil system's resulting of (C) a new external aqueous phase comprising components to modify the surface properties is added to minimize the opsonization of the nanoparticles and modify their biodistribution. This new aqueous phase includes PEGylating components as polyethylene glycols of various molecular weights, derivatives of vitamin D as tocopherol-succinate-PEG 1000, hydrophilic colloids (hydrophilic polymers natural as the polyvinyl alcohol . . . ) or peptides. Once the new aqueous phase is added, the secondary emulsion is obtained for example by ultrasonic homogenization, resulting in a solid gel system in oil in water. (E) Afterwards, the lipids are solidified by adding the resulting system of stage (D) to an aqueous dispersion of surfactants with HLB greater than 10, preferably in an ice bath. In this step the lipids are solidified and deposited on the surface of gel particles forming the nanostructured systems. It is important to clarify that, in this secondary emulsion, the new aqueous dissolution or dispersion constitutes the continuous or dispersing phase and gel droplets covered by the mixture of solid lipids and fluids the dispersed phase.

Additionally, it must be noted that the nanostructured lipid system can be obtained in a powdery solid form that can be easily reconstituted in an aqueous vehicle, giving rise to a homogeneous dispersion of NLCs with the appropriate characteristics for intravenous administration. To obtain the powdery solid drying techniques such as freeze drying or spray drying may be used. In the case of freeze-drying it is necessary to add cryoprotectant agents to avoid the aggregation of the NLC which would prevent the correct re-dispersion. Among other, cryoprotectants agents that can be used include sucrose, glucose, maltose, trehalose, sorbitol, cyclodextrins, and glycerin among others. For freeze drying, the NLC containing cryoprotective agents are frozen, preferably quickly, to then remove the water by freeze-drying.

Based on the methodology described above, we have developed the first lipid system that provides solid lipid nanoparticles and the first step was to immobilize the enzyme elosulfase alfa, an enzyme useful to treat Morquio's disease. For the preparation of nanoparticles loaded with the enzyme elosulfase alfa the following components were used: Poloxamer 407 as an agent for preparing a gelled aqueous core; dichloromethane containing Phosphatidylcholine (soy lecithin) and stearic acid as the external phase of the first emulsion (i.e. as the lipid coating layer of the gelled aqueous core), and 2% Solutol HS15 (12 acid polyglycol ester-hydroxy stearic) in the external phase of the multiple emulsion to complete the D and E stages.

As a result of this approach, solid lipid nanoparticles were obtained with sizes between 170-800 nm and with variable enzymatic loading. The main observed drawbacks were the low enzyme immobilization capacity of the nanoparticles and the poor stability of the formulations since the particles were aggregated quickly after their preparation.

In order to stabilize them and to improve the enzyme immobilization rate, different formulations were elaborated incorporating surfactants in the final aqueous phase such as tween 80, sodium taurocholate, sodium cholate or soy lecithin or polymers such as PEG 300, 400 and 6000. This approach was carried out with the purpose of coating the particles with a hydrophilic layer of PEG (polyethylene glycol) that improve the stability and prevent phenomena such as the opsonization of the nanoparticles in vivo. For this purpose, the incorporation of D-α tocopherol acid polyethylene glycol 1000 succinate into the second aqueous phase was also tested. The lipophilic radicals of this compound promoted the interaction with lipids, so the pegylation of the surface of the particles was greatly improved.

Despite these modifications, solid lipid nanoparticles were destabilized shortly after their manufacture, undergoing agglomeration processes and an increase in particle size was also observed over time. After analyzing the results, it was concluded that the instability was associated with the use of stearic acid as the only lipid component.

Stearic acid is a crystalline solid product at room temperature, with a melting temperature of 69° C. Stearic acid crystallizes over time, giving rise to unstable rigid nanoparticles. Therefore, it was decided to partially or totally replace the composition of the lipid phase in order to obtain more stable nanostructured lipid systems than the solid lipid nanoparticles and to increase the enzyme loading.

With this aim, several tests were carried out incorporating different lipid components: triglycerides of the medium chain caprylic and capric fatty acids, cholesterol, microcrystalline trimyristin or glyceryl trimyristate, tristearin or microcrystalline glycerol tristearate, glyceryl behenate, as well as different vegetable oils such as coconut oil, cotton or olive oil. Different synthesis conditions were also tested, modifying the intensity and the time of the ultrasound homogenization step as well as the temperature intervals in the different stages of the process. After all, the definitive formulation was established in the following way: elosulfase alfa immobilized in a gelled inner core based on a polymer (Poloxamer 407) that become gel as a function of temperature; a lipid coating of the gelled aqueous core formed by mixtures of the following solid and liquid lipids: glyceryl behenate, glyceryl trimyristate, tristearin, cholesterol, virgin olive oil, triglycerides of capric and caprylic medium chain fatty acids and liquid soy lecithin; D-α tocopherol acid polyethylene glycol 1000 succinate for pegylation of the surface of the particles; and poloxamer 188 as surfactant, and added at a temperature that allows to force the solidification of the lipids by thermal shock caused by the sudden drop in temperature.

With this formulation, the researchers carried out successful studies of cellular internalization and NLC uptake in lysosomes of healthy and pathological tissue samples. The expression of the proteins involved in the biological processes of glycosaminoglycan metabolism and in particular of the proteins involved with keratan sulfate and involved in biological processes related to the development of the disease (extracellular matrix synthesis, collagen, cartilage and bone) was also determined. The stability in plasma of the enzyme immobilized in the NLCs was studied to determine the level of protection against proteases. Finally, the in vivo biodistribution of NLCs in organs and tissues of experimental animal models after intravenous administration was studied.

With the aim to demonstrate that the present invention is not restricted solely to a single formulation, thereafter we have demonstrated the achievement of new stable nanostructured lipid systems from the selective substitution of some of the components existing in the aforementioned formulation.

In addition, the nanostructured lipid system of invention not only has utility to treat lysosomal diseases but as shown in FIGS. 31 to 35, and 37 to 38, depending on the type of loaded protein, it is also possible to use it to treat or prevent problems of degeneration of the cartilage and bone, and therefore, to prevent or treat diseases such as osteoarthritis, rheumatoid arthritis, lupus erythematosus or traumatic injury. Enzymes particularly useful for the said treatment or prevention of degeneration of the cartilage in the nanostructured lipid system of the invention can be selected from the list consisting of: Laronidase [Aldurazyme®], idursulfase [Elaprase®], elosulfase alfa, and alfa vestronidasa [Mepsevii®]. Enzymes particularly useful for the said treatment or prevention of degeneration of the bone in the nanostructured lipid system of the invention, is elosulfase alfa.

On the other hand, the table above shows how olive oil (which is part of the liquid lipids) is interchangeable by cod liver oil or sunflower oil, liquid soy lecithin can be substituted by egg lecithin. The microcrystalline Trimyristin can be substituted by mixtures of triglycerides of caprylic and capric acid, Poloxamer 188 can be substituted by glyceride of capriocaproil macrogol-8/polyoxyl-8 and glyceryl behenate by glyceryl distearate.

It is thus important to clarify that the nanostructured lipid system of invention can have different compositions of the lipid layer. A lipid layer, in the context of the present invention, must be thus made up of a mixture of liquid and

| Substituted component | Added component | Size | PdI | Zeta potential | Yield % or formulation weight with respect to the initial weight of solids | Inmobilized enzyme | Enzymatic activity in nucleous. (μmol/L/h) | Enzymatic activity at surface. (μmol/L/h) |
|---|---|---|---|---|---|---|---|---|
| elosulfase alfa | laronidase | 246.8 | 0.154 | −14.4 | 56.352 | laronidase | 3.6 | 108 |
| elosulfase alfa | laronidase | 227.3 | 0.118 | −14.0 | 48.055 | laronidase | 3.8 | 164.6 |
| behenate of glyceril | Precirol gliceryl diestearate | 211.2 | 0.136 | −14.8 | 53.209 | laronidase | 5.6 | 163 |
| Poloxamer 188 | Gliceryl Caprio caproil macrogol-8/polyoxyl-8 | 185.7 | 0.175 | −11.2 | 23.209 | laronidase | 1.4 | 171.8 |
| Microcrystalline Trimyristin | triglycerides of the capric and Caprylic acid | 191.7 | 0.124 | −14.8 | 41.154 | laronidase | 2.4 | 29.8 |
| liquid soy lecithin | Egg lecithin | 195.8 | 0.102 | −9.44 | 53.141 | laronidase | 243 | 243 |
| Olive oil | Sunflower oil | 214.8 | 0.163 | −14.9 | 44.703 | laronidase | 3.6 | 84.4 |
| Olive oil | Cod liver oil | 278.9 | 0.290 | −11.9 | 27.736 | laronidase | 2 | 200 |
| Elosulfase alfa | laronidase | 246.8 | 0.154 | −14.4 | 56.352 | laronidase | 3.6 | 108 |
| Elosulfase alfa | laronidase | 227.3 | 0.118 | −14.0 | 48.055 | laronidase | 3.8 | 164.6 |
| Elosulfase alfa | idursulfase | 194.7 | 0.163 | −15.7 | 34.484 | idursulfase | 816 | 640 |
| Elosulfase alfa | idursulfase | 206.5 | 0.138 | −15.3 | 54.418 | idursulfase | 742 | 448 |

As shown the table above, the immobilized enzyme in the nanostructured lipid system of the invention may be replaced with success by other enzymes, such as idursulfase or laronidase. Therefore, the nanostructured lipid system of invention is not in any case limited to immobilizing elosulfase alfa for use in the treatment of Morquio A, but also this formulation may be used in treatment of other lysosomal storage diseases. Depending on the enzyme which is used to load in nanostructured lipid systems other lysosomal diseases could be treated. Examples of diseases that could be treated using nanostructured lipid systems of invention are: Hurler disease, disease Herler-Scheie, Scheie disease or Hunter disease.

solid lipids. The mixture can be simple (a single component of each class, a liquid and a solid) or complex (several components of every category, liquids and solids). In any case, it is essential or necessary to put together these two types of lipids (liquid and solid) to get an elastic and resistant lipid layer. If only solid lipids are used, such as stearic acid as example, the layer would turn out in too rigid coating, and lipids tend to crystallize destabilizing the nanostructured lipid system of invention. However, the incorporation of liquid lipids, which act as a plasticizer, allows the formation of a layer more elastic and resistant. On the other hand, if only liquid lipids are used, the consistency of the lipid layer is very low leading the formation of an emulsion instead of the nanostructured lipid system of invention.

In the context of the present invention the term "solid lipid" refers to: lipid material solid or waxy at room temperature (25° C. at 1 atm), composed by fatty acids, preferably long chain fatty acids, with a fusion event that begins (onset temperature) at temperatures above 35° C., determined by differential scanning calorimetry (DSC), preferably by over 37° C., most preferably above 40° C., with an HLB value lower than 10 and densities between 0.8 and 1 g/cm$^3$. Examples of solid lipids are long-chain fatty acids and their esters (stearic acid, palmitic acid, arachidic, behenic, palmitostearate of glyceryl, dibehenate of glyceryl cetylpalmitate, glyceryl tristearate, trimyristin, tripalmitin), phospholipids, acids and bile salts (e.g. taurocholate deoxicolate, glicocolate, hiodeoxicolate, glicocolate, litocolate and similars . . . ).

In the context of the present invention the term "liquid lipids" refers to: lipid material that behaves as a liquid at room temperature, composed on fatty acids, preferably short chain fatty acids, with a fusion event that begins (onset temperature) at temperatures below 30° C. and densities ranging from 0.88 to 0.97 g/cm$^3$. Some examples are short and medium chain fatty acids and their esters (e.g. valeric, caproic, caprylic, capric, lauric, pelargonic and enantic acid, lauroyl-polyoxy-glicerides or caprylic triglycerides . . . ), tocopherol or other vitamin E derivatives, natural oils of vegetable or animal origin (olive, soybean, sunflower, coconut, cotton, sesame, maize, cod liver oil . . . ).

It is important to note that according to the nomenclature recommended by the IUPAC for the abbreviated name of fatty acids based on the variant "n", the following formula is used:

$$C:D\ n-x,$$

Where: C: represents the number of carbon atoms of the fatty acid;
  D: the number of double bonds in the fatty acid, where it is assumed that the double bonds are in (the most common in the natural fatty acids) cis position;
  n: the position of the distal double bond, where n is the total number of carbons and x a number that provides the position. He is considered that, in the case of multiple chemical bounds, these are separated by a methylene group.

Example

Stearic acid: $CH_3(CH_2)_{16}COOH$; C18:0
Oleic acid: $CH_3(CH_2)_7CH=CH(CH_2)_7COOH$; 18:1n-9
Arachidonic acid: $CH_3(CH_2)_4CH=CH_2CH=CHCHCH_2CH=CHCH_2CH=CH(CH_2)_3COOH$; 20:4n-6

Therefore in accordance with this nomenclature, and in a preferred embodiment of the invention the lipid solids of the present are those that meet the following criteria
  (a) saturated fatty acids presenting values of C≥12 and C<41 and D=0;
  (b) unsaturated fatty acids and polyunsaturated trans, C>17 and C<25, D≥1, x between 1 and n−2;
  (c) monoesters of saturated fatty acids with values of C>14 and C<41 and D=0 with sorbitano, polyoxyethylene, polioxietilensorbitano, glycerine or diethylene glycol;
  (d) tri-esters formed between glycerol and saturated fatty acids with C≥3 and C<41 and D=0;
  (e) tri-esters formed between glycerol and unsaturated trans fatty acids; o
  (f) mixtures of any of them On the other hand in accordance with this nomenclature, and in another preferred embodiment of the invention liquid lipids are those that meet the following criteria
  (a) saturated fatty acids presenting values of C≥3 and C≤11 and D=0;
  (b) unsaturated fatty acids and polyunsaturated cis with C≥3 and C≤23, D≥1, x between 1 and n−2;
  (c) monoesters of fatty acids saturated with a values of C≥3 and C>14 y D=0 with sorbitan, polyoxyethylene, polyoxyethylen-sorbitan, glycerine or diethylene glycol;
  (d) tri-esters formed between glycerol and fatty acids saturated with C<3 and D=0
  (e) tri-esters formed between glycerol and unsaturated cis fatty acids C≥3 and C≤23, D≥1, x between 1 y n−2; or
  (f) mixtures of any of them In the context of the present invention the term "sterols" refers to: steroids formed by 27 to 29 carbon atoms. Its chemical structure is derived from the cyclopentane-hydrophenanthrene (sterane), a 17 carbon molecule made up of three hexagonal rings and pentagonal one. Cholesterol and bile salts are classified in the sterols group, which are used to give consistency to membranes and lipid layers and also as natural surfactants. Examples of sterols are cholesterol, the cholate sodium, sodium taurocholate.

In the context of the present invention the term "lipid soluble surfactants or lipids-dispersable surfactants" is understood as: surface-active molecules with low HLB values, less than 10. Lipids-dispersible surfactants are used in the first phase of the fabrication of the NLC to prepare the primary emulsion between the aqueous core components and the lipid layer. These surfactants are selected since they preferentially stabilize water in oil (W/O) emulsions. An example is the solid soy lecithin or egg lecithin with an HLB of 9.5.

In the context of the present invention the term "water soluble surfactants or water-dispersable surfactant" is understood as: surface-active molecules with HLB higher than 10 which stabilize emulsions of inner oil phase in external water phase. These surfactants are used in the last stage of the elaboration of the NLC, when the multiple W/O/W emulsion is formed to produce the hardening of the lipid layer. Examples of these surfactants are the Poloxamers, the glycerides, C8-C10 of polyethylene glycol, polysorbate 80, or own bile salts.

In the context of the present invention the term "pegylants agents" refers to: polymers derived from ethylene glycol, as the polyethylene glycols of various molecular weights, esters with fatty acids (eg. (15)—polyethylene glycol hydroxystearate) or with tocopherols. All are surface-actives, are dispersible in water and have HLB values >10. These products are able to stay accumulated on the surface of the NLC making it more hydrophilic. In the case of linear polymers of PEG (PEG 300, 400, 6000, 10000 etc.) an adsorption occurs on surface and in the case of the esterified derivatives such as tocopherol succinate-PEG 1000, tocopherol is anchored to the lipid layer, making it more effective.

The term "nanoparticle" refers to a structure with an average particle size less than 1 μm, and generally between 1 and 300 nm.

In the present invention Nanostructured lipid System is understood as a release system made of nanoparticles or nanocapsules prepared from, among other components, for mixtures of solid and liquid lipids. Due to the presence of a liquid lipid in the structure, a crystalline solid lipid network is disrupted and then, the crystallinity is reduced.

To study the physical properties of fusion processes of the lipid layers that are useful in the nanostructured lipid system of the invention, different mixtures (see table below) between solid lipid (M5), liquid lipids (M4) and solids and liquids (M1, M2, M3 and M6) were prepared. A treatment similar to that undergo these lipids in the preparation of the nanostructured lipid system of the invention was used. Lipids were dissolved in dichloromethane and evaporate to 50° C. to remove the solvent. Finally, the obtained mixtures were stored 24 hours at 5° C., and the same operation was carried out with pure solid lipids.

Differential Scanning calorimetry (DSC, TA Discovery) was used to determine the properties of fusion of mixtures of lipids by undergoing an initial cooling cycle from ambient temperature to 0° C. and later, warming up to 100° C. Both, performed at a heating rate of 10° C. per minute.

crystallinity than solid lipids. Lipids that begin to melt from the 50° C. can give rise to problems of stability. For these lipids, DSC curves also indicate a greater crystallinity degree than in mixtures of solid and liquid lipids.

In addition, to determine the modification in the crystallinity of the compositions of lipids tested in the nanostructured lipid system of invention comparing to solid lipids, the diffraction of crystalline powder was used. A diffractometer Philips, managed with a "PW1710", a vertical goniometer control unit "PW1820/00" and a "Enraf Nonius FR590" generator that operates at 40 Kv and 30 mA was used. X-rays were obtained from a sealed Cu tube and a graphite monochromator (X (Kan=1, 5406a). The XRD patterns were obtained within an angular range of 2-50° with a step of 0.02° and a time step of 2 s. Samples were taken to obtain optimal peak profiles for analysis, as well as to minimize the effect of preferred orientation. They were deposited on a

| M1 | | M2 | | M3 | | M4 | | M5 | | M6 | |
|---|---|---|---|---|---|---|---|---|---|---|---|
| glyceryl behenate | 25 mg | glyceryl behenate | 75 mg | | | | | glyceryl behenate | 91.5 mg | glyceryl behenate | 37 mg |
| timyristin | 25 mg | | | timyristin | 37.5 mg | | | timyristin | 91.5 mg | timyristin | 25 mg |
| tristearin | 25 mg | | | tristearin | 37.5 mg | | | | | tristearin | 25 mg |
| Cholesterol | 12 mg | Cholesterol | 12 mg | Cholesterol | 12 mg | | | | | | |
| Virgin olive oil | 100 mg | Virgin olive oil | 100 mg | Virgin olive oil | 100 mg | Virgin olive oil | 100 mg | | | Virgin olive oil | 100 mg |
| Triglycerides caprylic and capric acid | 33 mg | Triglycerides caprylic and capric acid | 33 mg | Triglycerides caprylic and capric acid | 33 mg | Triglycerides caprylic and capric acid | 33 mg | | | Triglycerides caprylic and capric acid | 33 mg |

Figure 23:
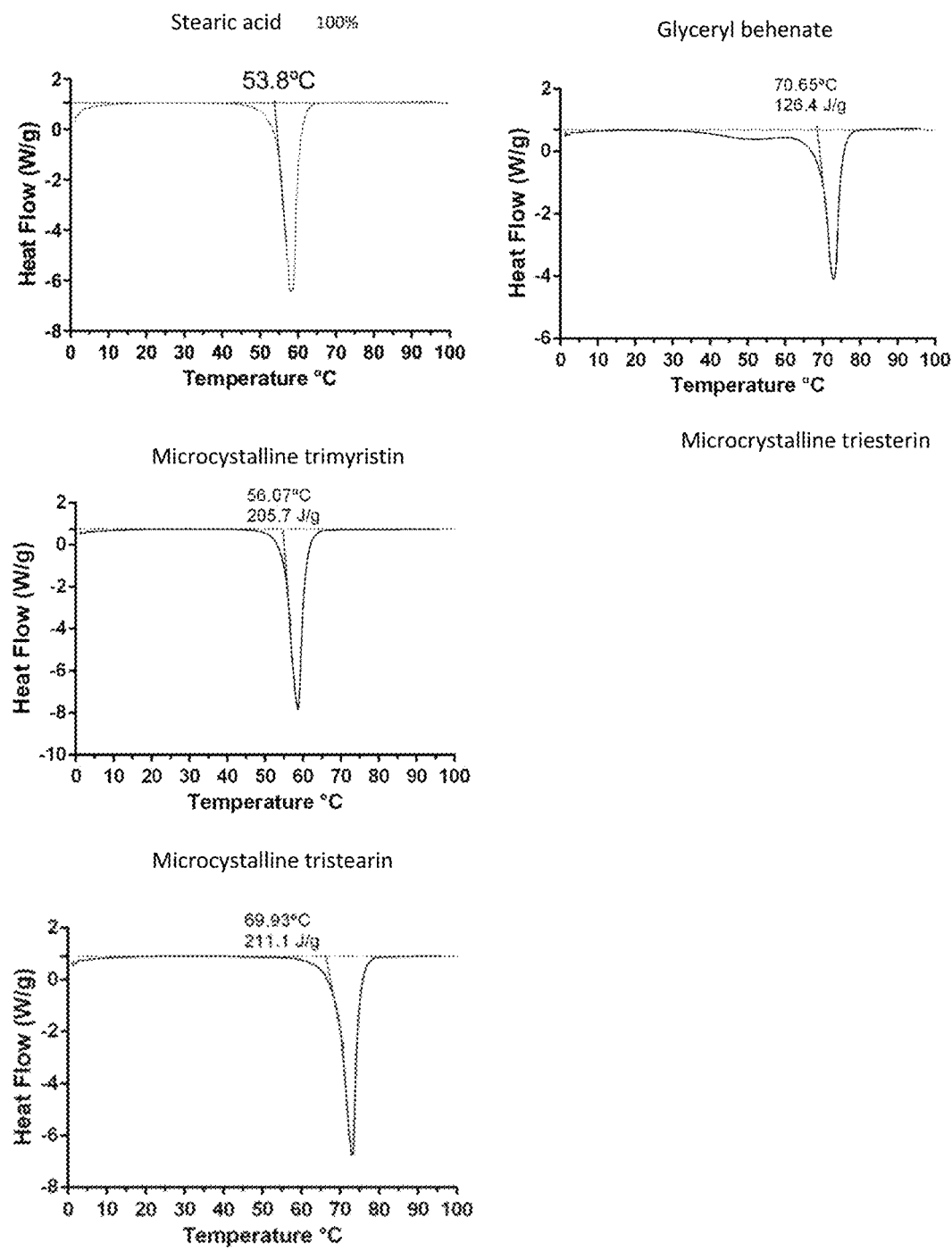
FIG. 23 DSC curves of solid lipids samples.

FIG. 23 shows the DSC curves of pure solid lipids. Solid lipids show a clear and sharp peak well defined with an onset temperature greater than 50° C. The sharp and well-defined bands of fusion are characteristic of high crystalline products.

Figure 21:
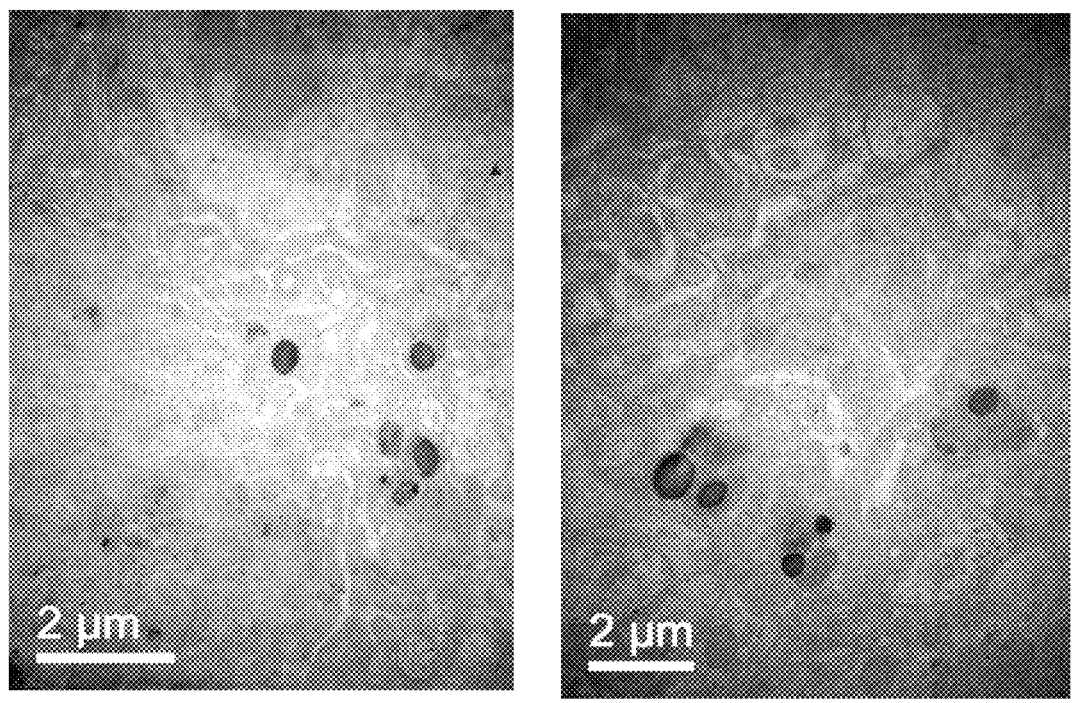
FIG. 21 Microphotographs obtained by transmission electronic microscopy of brain tissue samples from mice euthanatized 24 hours after the NLC administration by intravenous injection. In the picture, several NLC localized in the cytoplasm of neurons are observed.
Figure 24:
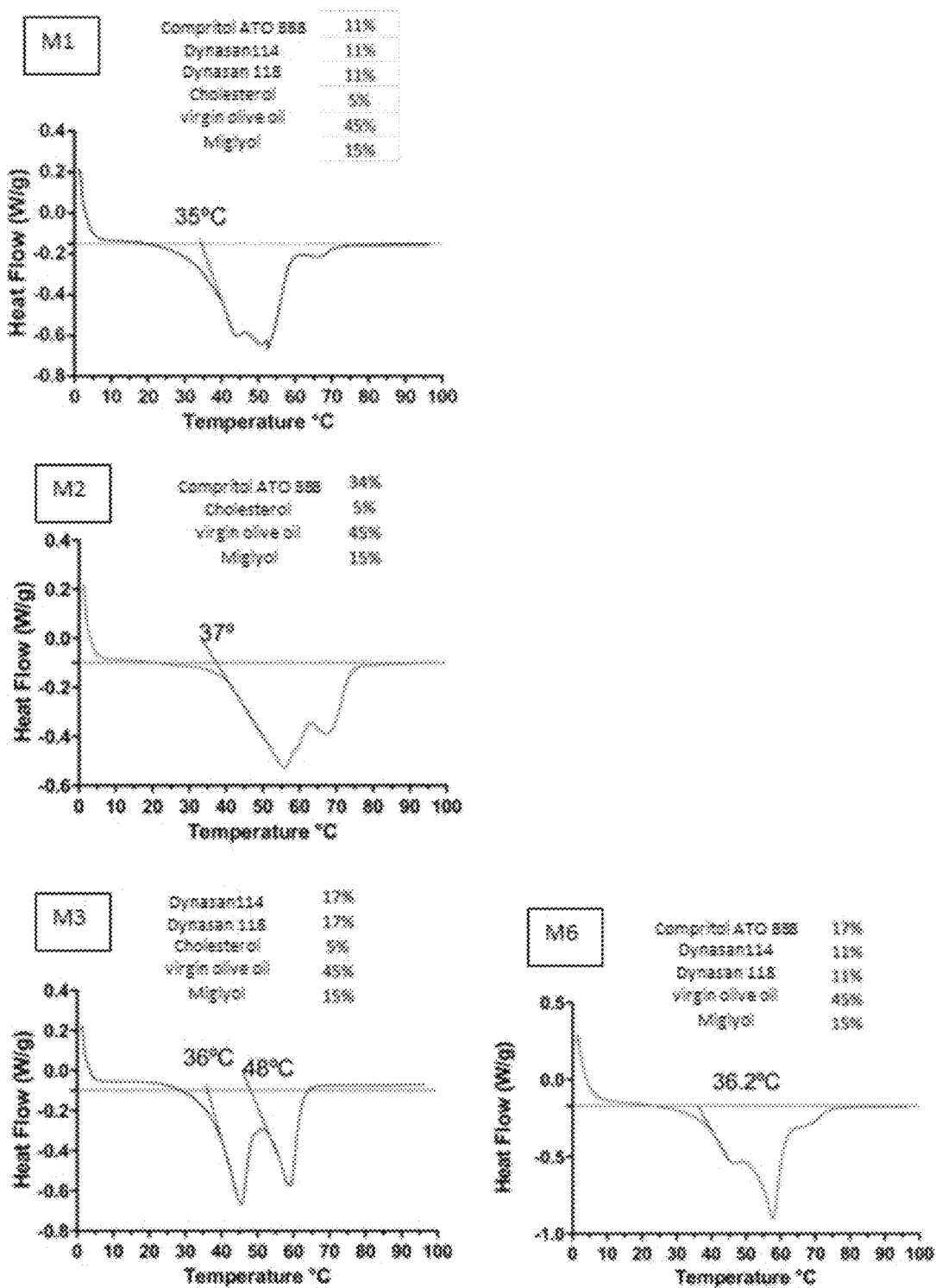
FIG. 24 DSC curves of some mixtures of solid lipids and liquids lipids used in the elaboration of the NLC. Mixtures include trimiristine (dynasan 114), tristearin (Dynasan 118) glyceryl behenate (Compritol ATO 888), triglycerides of capric and caprylic acid (Mygliol 812), cholesterol and olive oil.
Figure 25:
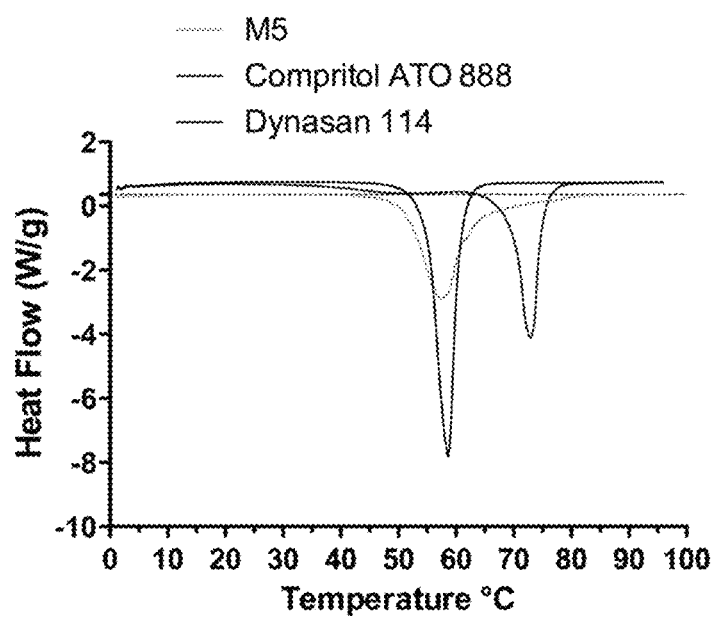
FIG. 25 DSC curves of glyceryl behenate (Compritol ATO 888), trimyristin (Dynasan 114) and its 1:1 mixture (P/P).

DSC of mixtures are shown in FIG. 24. In this figure, it is observed that the temperature of fusion decreases significantly compared with pure products, fusion bands are wider and the flow of heat per gram of substance is significantly lower than in the case of pure products. These changes indicate that solid lipids are more crystalline than mixtures. According to the literature timyristin and tristearin have a $T_{onset} > 53°$ C. and glyceryl behenate approximately 70° C., values that are coincident with those observed in FIG. 21. The mixture of trimyristin and glyceryl behenate reduces the melting temperature of the latter but remains above 50° C. and with a high degree of crystallinity, similar to the pure products (see FIG. 25).

Figure 26:
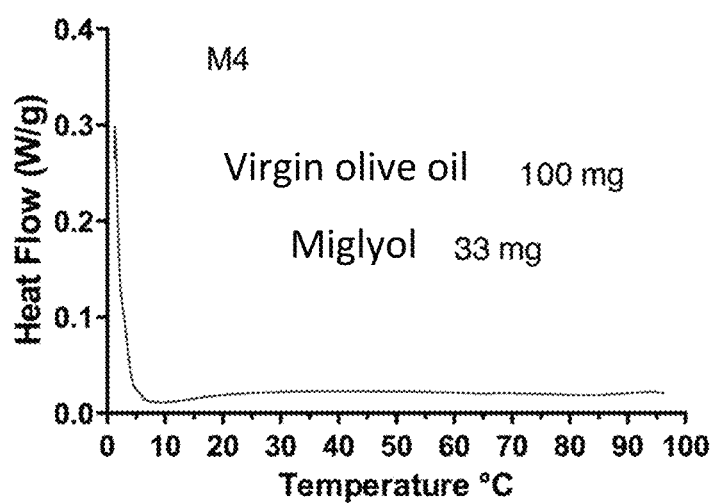
FIG. 26 DSC curves of olive oil, capric and capric triglycerides (Mygliol 812) and their mixtures (M4).
Figure 27:
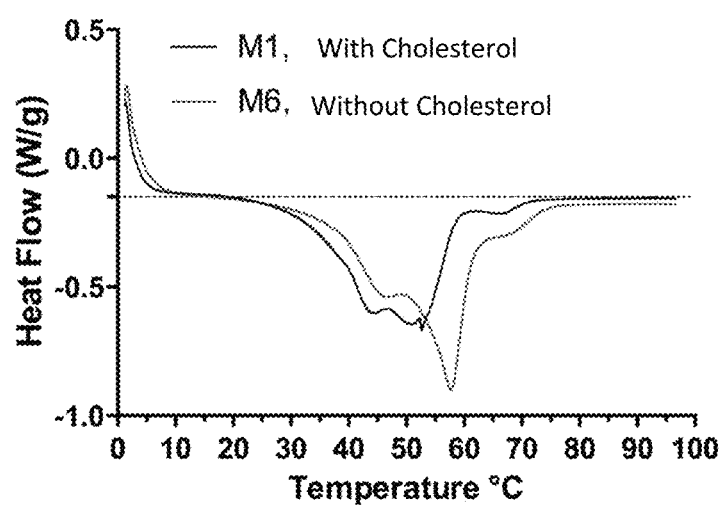
FIG. 27 DSC curves of mixtures M1 and M6. Both have the same composition but M1 also has cholesterol in the preparation.

On the other hand, liquid lipids do not show any transition (fusion) in the range of temperature studied, indicating that they are in liquid phase (see FIG. 26). In the mixtures, the presence of liquid lipids decrease significantly the melting temperature ($T_{onset}$), found around the interval 20° C.-40° C. In addition, heat flow (W/G) decreases significantly, indicating that mixtures form a less crystalline product than solid lipids. Thus, the addition of cholesterol at the mixtures leads to a more important decrease in the onset temperature and in the melting range, as well as in the crystallinity, acting as a plasticizer (see FIG. 24). Therefore in accordance with the results shown in FIGS. 21 to 25, the compositions of lipids tested more adequate to the elaboration of the nanostructured lipid system of invention are mixtures that begin to melt at temperatures between 20 and 40° C. having lower base of oriented crystals (Si (511) plate) to avoid the dispersion caused by vitreous support.

Figure 28:
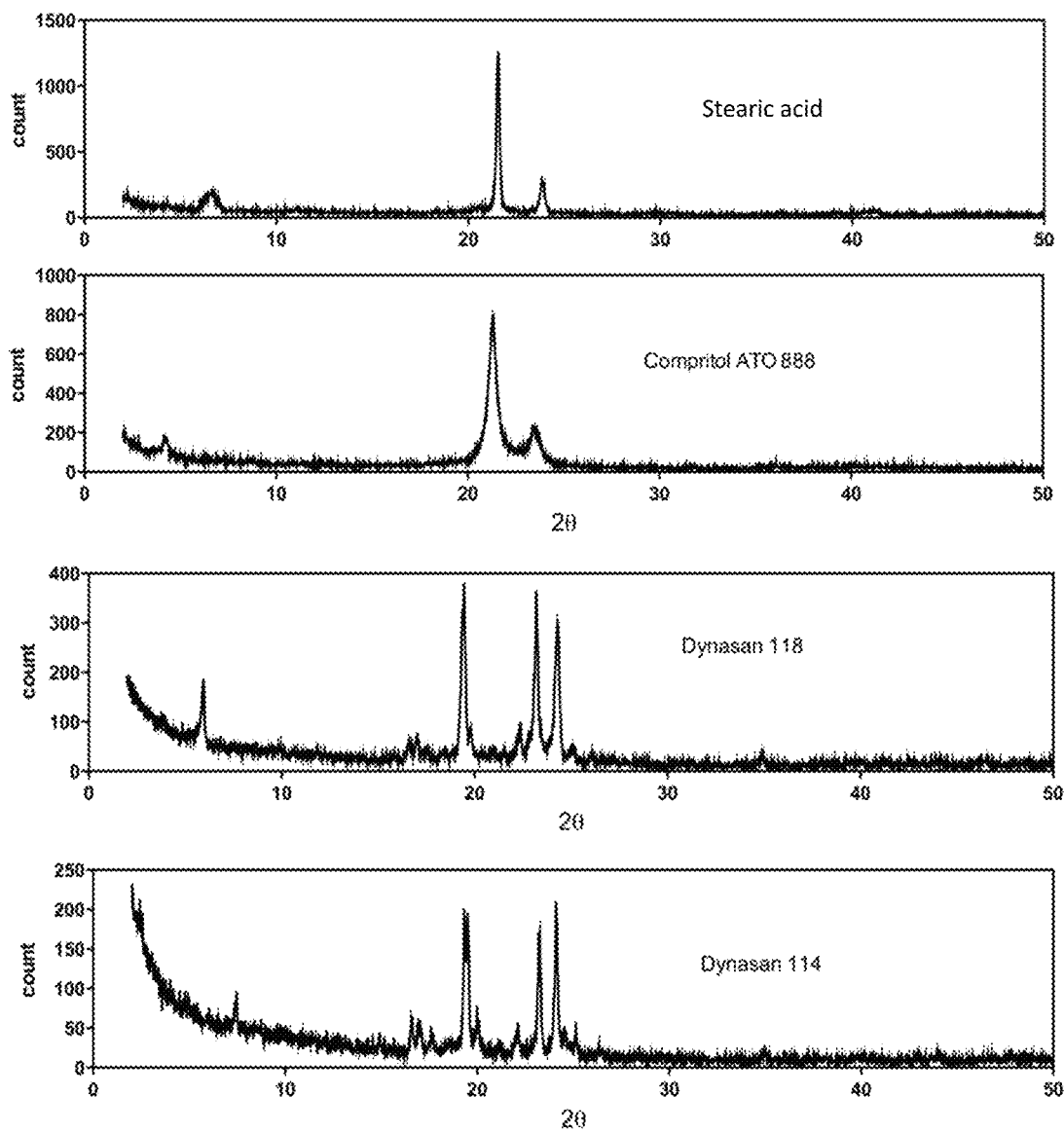
FIG. 28 X-ray diffractograms of some of the solid lipids used in the invention.
Figure 29:
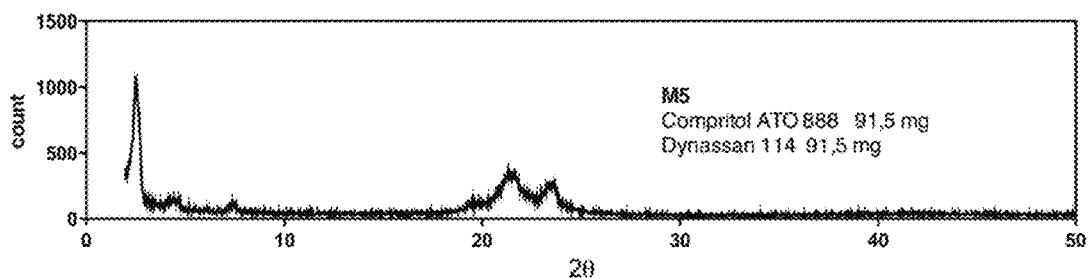
FIG. 29 X-ray diffractograms of the M5 mixture containing glyceryl behenate and trimyristin in a ratio of 1:1 (w:w).
Figure 30:
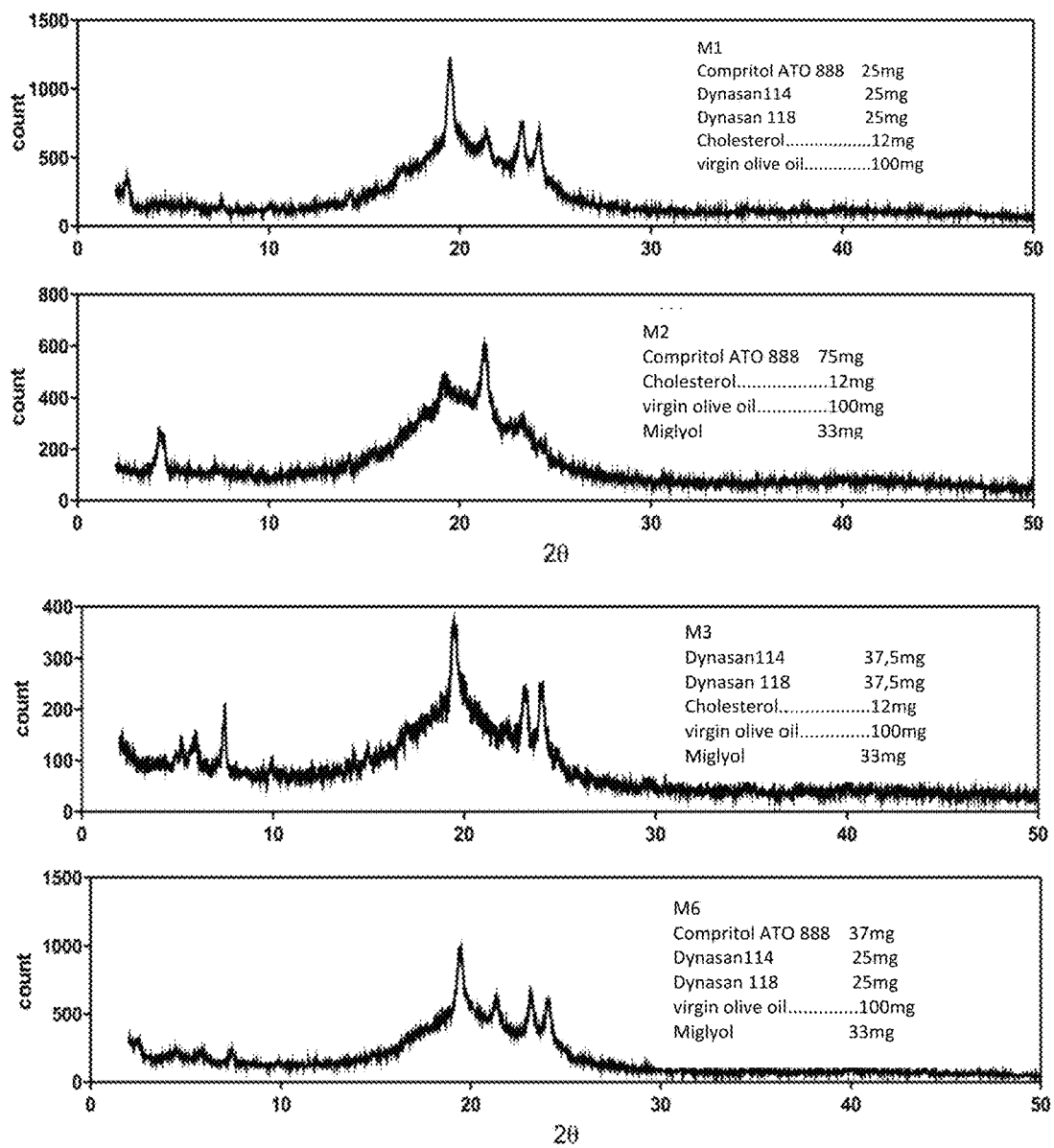
FIG. 30 X-ray diffractograms of mixtures M1, M2, M3 and M6 containing different solid lipids and liquid lipids.
Figure 31:
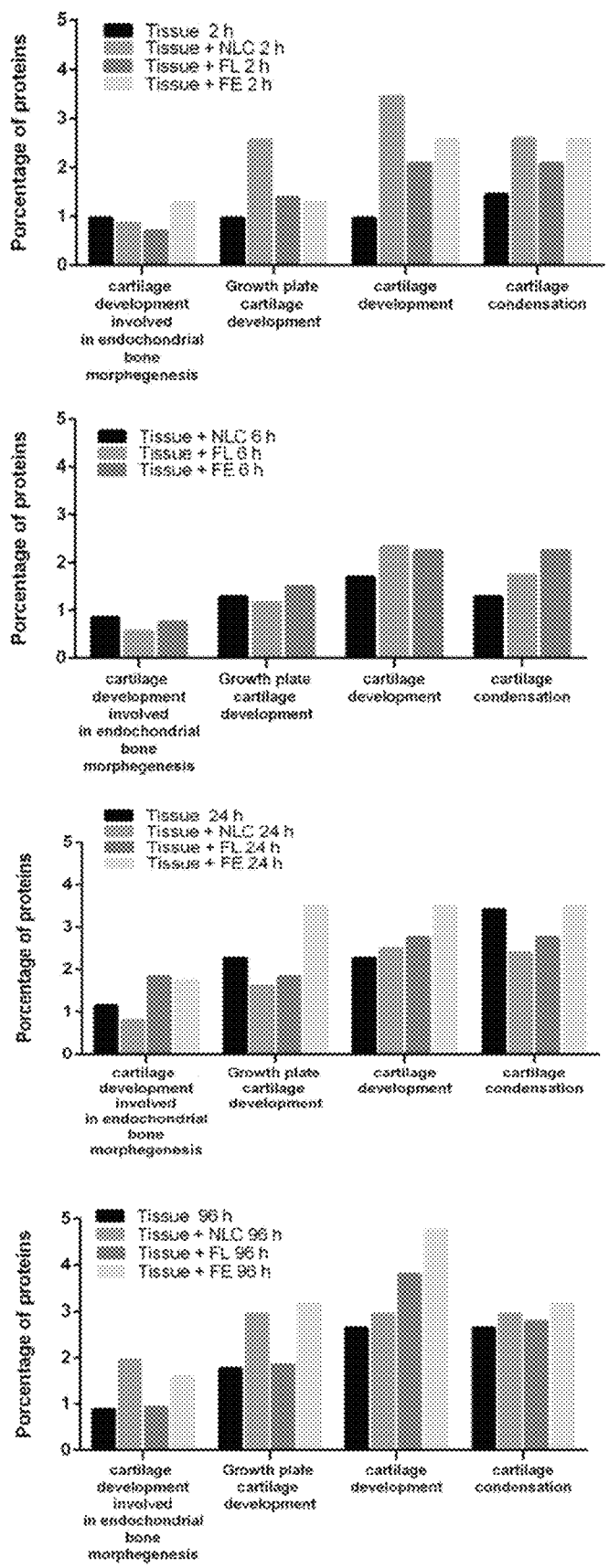
FIG. 31. This figure represents the expression of proteins (% p/p) of cartilage tissue samples from healthy donors from the main biological processes related to the development and growth of cartilage. In all cases and for all the times a greater expression of proteins is observed in tissues incubated with elosulfase alfa immobilized on NLC despite the enzyme concentration is 2000 times lower than the free enzyme solution.
Figure 32:
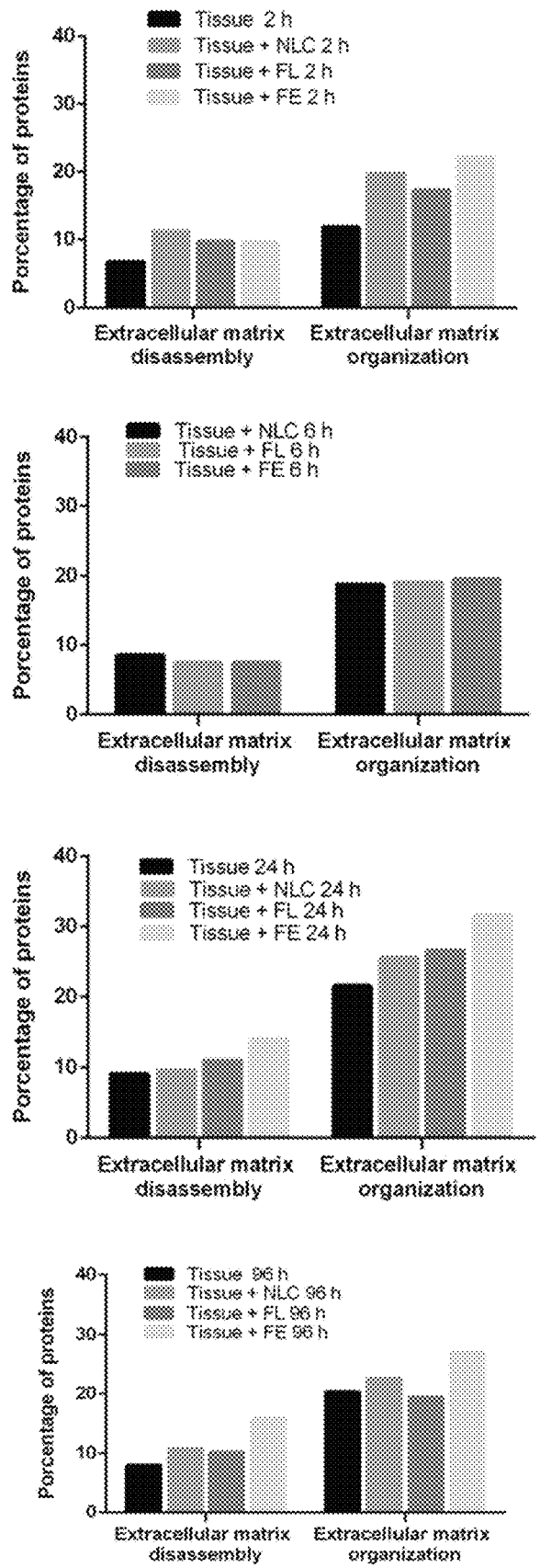
FIG. 32. This figure represents the expression of proteins (% p/p) of cartilage tissue samples from healthy donors of the main biological processes related to the development and growth of the extracellular matrix. In all cases and for all the times investigated a greater expression of proteins is observed in tissues incubated with elosulfase alfa immobilized on NLC despite of the enzyme concentration is 2000 times lower than the free enzyme solution.
Figure 33:
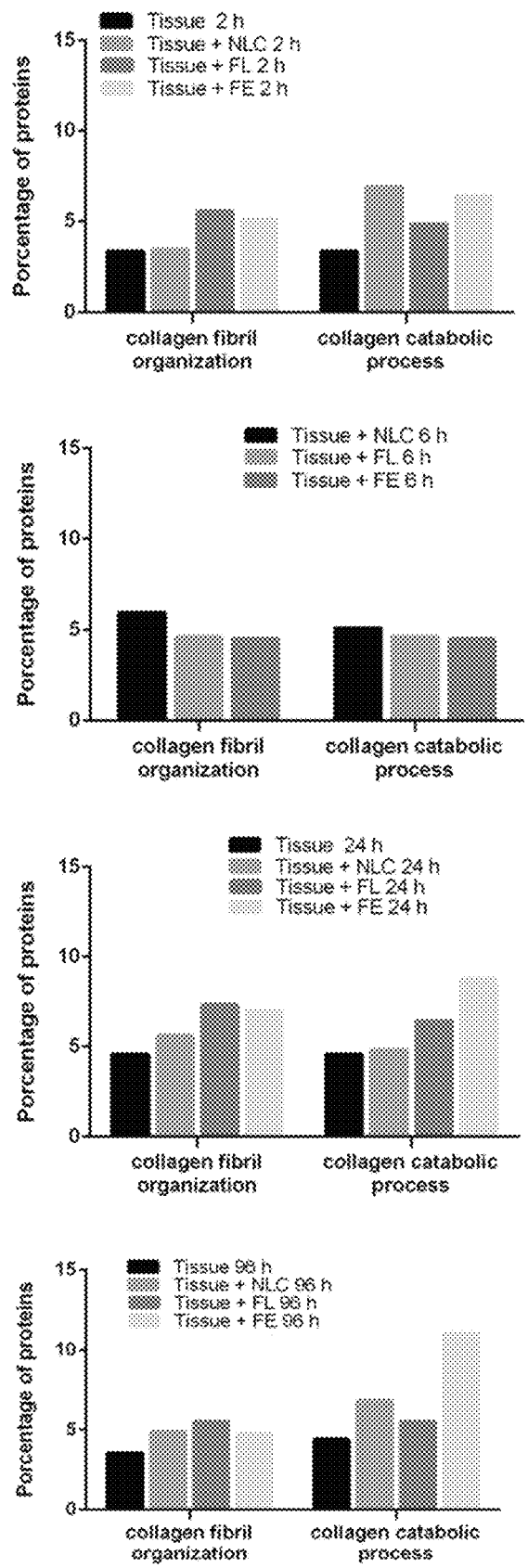
FIG. 33. This figure represents the expression of proteins (% p/p) of cartilage tissue samples from healthy donors of the main biological processes related to the development and growth of the collagen. In all cases and for all the times investigated a greater expression of proteins is observed in tissues incubated with elosulfase alfa immobilized on NLC despite of the enzyme concentration is 2000 times lower than the free enzyme solution.
Figure 34:
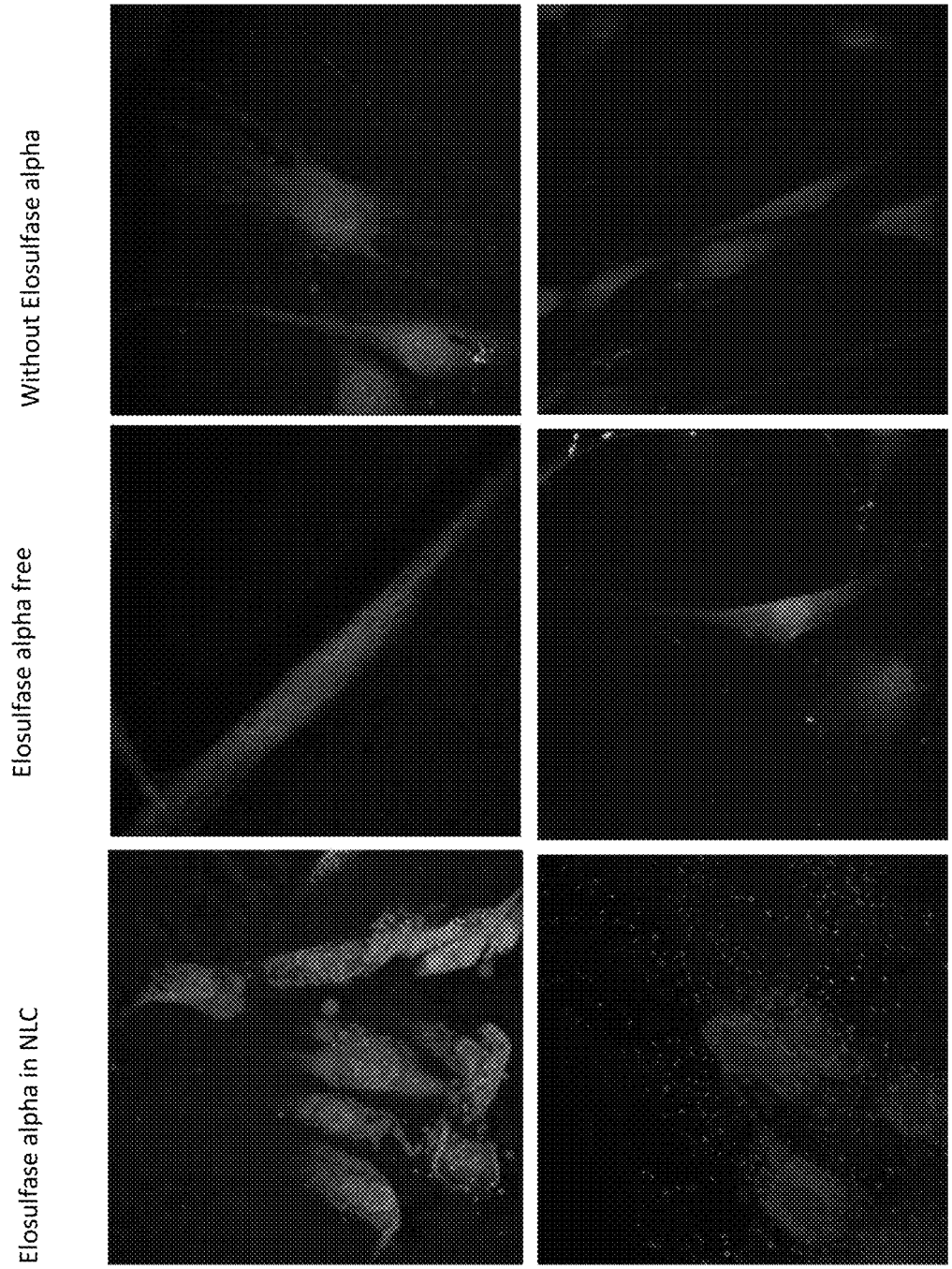
FIG. 34. Images of Immunohistochemistry obtained by the functional test of a protein, Lumican, related to the development of collagen fibers in fibroblast samples from healthy donors and Morquio A patients. The pictures include cells treated with free elosulfase alfa or immobilized in NLC. An increase in the expression of lumican in both cases is observed.

FIG. 28 shows the X rays diffractogram of pure products. Patterns indicate crystalline structure of stearic acid and the glyceryl behenate. In the case of the trimyristin and microcrystalline tristearin, they also show crystalline phases but with less marked peaks than in previous cases. FIG. 29 shows the diffractogram of x-rays of solid lipid mixtures. The diffractogram shows a loss of crystallinity when mixtures of both products are dissolved in dichloromethane and evaporate solvent. The treatment appears to decrease significantly the crystallinity of pure products but the crystalline phase can still be observed. FIG. 30 shows the x-ray diffractogram of the of mixtures of liquid and solid lipid. Patterns of co-evaporated solid and liquid lipids mixtures indicate an increase of the amorphous fraction of mixtures with the presence of some crystalline solid. Mixtures of 1, 3 and 6 show a small fraction of crystalline trimyristin and microcrystalline tristearin and very small portions of glyceryl behenate glyceryl. The product is more amorphous than the pure components.

Therefore, the conclusion is that those tested lipid compositions that work better in the nanostructured lipid system of the invention, are those made up of a mixture of liquid and solid lipids that produces a low crystalline system compared to solid lipids, but with an adequate consistency in coating. High crystallinity of pure products or solid lipid mixtures would destabilize the nanostructured lipid system of the invention. However, the presence of liquid lipids, which act as a plasticizer, enable the cover to be more elastic and therefore, resistant.

In short, the nanostructured lipid system of the present invention comprises solid lipid nanoparticles, whose structure and crystalline network is disrupted by the presence of liquid lipids, which comprises the following structural configuration:

a. A core, comprising an aqueous solution or dispersion, preferably gelled. The inner core is made of an aqueous solution, dissolution or dispersion which may include: water, pH buffer solution, salts, as well as a thermosensitive or ion-sensitive polymer that becomes a gel in function of the temperature or the concentration of ions. Preferably, this polymer is Poloxamer 407. However, other possible gelling agents useful in the present invention be selected from the list which consists of: chitosan, hydroxypropyl cellulose (HPC), hydroxipropilmetil cellulose (HPMC) and diblock copolymer of acid and polyethylene glycol and polilactic acid (PEG-PLGA-PEG);

b. A lipid layer coating made of a mixture of liquid and solid lipids. The mixture can be simple one (a single component of each class, a liquid and a solid lipid) or complex (several components of each classification). It is necessary to put together these two types of lipids for an elastic and resistant lipid layer. If you use only solid lipids, such as for example stearic acid, covers are too rigid and these lipids tend to crystallize destabilizing the NLC. The presence of liquid lipids, which act as a plasticizer, allows layer to be more elastic and therefore resistant. Conversely, if only liquid lipids are used, the consistency of the cover is very low, producing an emulsion instead of NLC. Such layer also comprises lipids soluble or dispersable surfactants, i.e., surface-active molecules with HLB values lower than 10. Lipid-dispersable surfactants are used in the first phase of preparation of the nanostructured lipid system of the present invention, to obtain a primary W/O emulsion containing the aqueous core and the components of the lipid layer. These surfactants are used since they preferentially stabilize water in oil (W/O) emulsions. An example are the soy or eggs lecithins's with HLB of 9.5; and c. A pegylated layer coating the lipid layer. PEG can be used, but PEG esters with other components more hydrophobic, as tocopherol succinate-PEG 1000 are preferred because allows anchoring PEG in the lipid layer increasing its stability. This layer also comprises water soluble or dispersible surfactants (HLB>10). They are used to stabilize the system and to promote the formation of the NLC during the cooling of the solution contributing to the stability of the final system.

Therefore, in a first embodiment the invention refers to a nanostructured lipid system comprising nanoparticles which in turn comprise:

a. a core, preferably gelled, comprising an aqueous solution or dispersion comprising a polymer that becomes a gel in function of the temperature (a temperature responsive polymer) or the concentration of ions;

b. a lipid layer coating the core made of or comprising a mixture of:
   a) a solid or a waxy lipid at room temperature (25° C. at 1 atm), composed of fatty acids, preferably long chain, with a process of fusion that begins (onset temperature) in temperatures above 35° C., determined by differential scanning calorimetry (DSC), preferably above 37° C., more preferably above 40° C., with an HLB value lower than 10 and densities between 0.8 and 1 g/cm$^3$, or a mixture of such solid lipids, and
   b) a lipid which behaves as liquid at room temperature, formed by fatty acids, preferably short chain, with a fusion process that begins (onset temperature) at temperature less than 30° C., differential scanning calorimetry (DSC) and densities ranging from 0.88 to 0.97 g/cm$^3$, where the mixture of lipid and solid lipid presents a fusion process that begins (onset temperature) at temperatures between 20° C. and below 50° C., preferably between 20° C. and 45° C., most preferably between 25° C. and 35° C. even more preferably between 30° C. and 40° C., determined by differential scanning calorimetry (DSC), where the mixture of solid and liquid lipids, are mixed in a ratios (lipid liquid: solid lipid, expressed in % by weight in reference to the total amount of the lipid components of the cover) of 98:2 to 1:99, preferably between 80:20 and 20:80, more preferably between 30:60 to 50:50; and where such lipid layer also comprises lipid soluble or lipid-dispersable surfactants;

and c. a pegylated layer coating the lipid layer that also comprises water soluble or water dispersable surfactants.

Preferably, the solid lipid of the lipid layer is selected from the list consisting of:
(a) saturated fatty acids presenting values of C≥12 and C<41 y D=0;
(b) unsaturated and polyunsaturated trans fatty acids. C>17 and C<25, D≥1, x between 1 y n−2;
(c) monoesters of fatty acids saturated with values of C≥14 and C<41 and D=0 with sorbitan, polyoxyethylene, polyoxyethylensorbitan, glycerine or diethylene glycol;
(d) tri-esters formed between glycerol and fatty acids saturated with C≥3 and C<41 and D=0;
(e) tri-esters formed between glycerol and trans unsaturated fatty acids; or
(f) mixtures of any of them More preferably, lipid layer liquid lipids are selected from the list that consists of:
(a) saturated fatty acids presenting values of C≥3 and C≤11 and D=0;
(b) unsaturated fatty acids and polyunsaturated cis with C≥3 and C≤23, D≥1, x between 1 y n−2;
(c) monoesters of saturated fatty acids with a values of C≥3 and C<14 and D=0 with sorbitan, polyoxyethylene, polyoxyethylensorbitan, glycerine or diethylene glycol;
(d) tri-esters formed between glycerol and fatty acids saturated with C<3 and D=0
(e) tri-esters formed between glycerol and cis unsaturated fatty C≥3 y C≤23, D≥1, x entre 1 y n−2; or
(f) mixtures of any of them Even more preferred, the lipid layer cover is made of a mixture of solid and liquid lipids in a ratio of 30:70 and 50:50 (ratio expressed as a percentage by weight of solid and liquid lipids with respect to the total lipid composition of the layer) and these mixtures have a fusion event that starts at temperatures between 30 and 40 degrees, determined by differential scanning calorimetry (DSC). Also preferably, lipid core layer is made of a mixture of liquid and solid lipid in a 45:55-35:65 ratio (ratio expressed as a percentage by weight of solid and liquid lipids with respect to the total lipid composition of the lipid layer) and such mixtures presents a fusion event that begins (onset temperature) at temperatures between 35 and 40° C., as determined by differential scanning calorimetry (DSC).

In a prefer embodiment of the first aspect of the invention, the aqueous dissolution or dispersion of the core comprises a polymer that become gel according to the temperature (a temperature responsive polymer) selected from the list consisting of: poloxamer 407, chitosan, hydroxypropyl cellulose (HPC), hydroxypropilmethyl cellulose (HPMC) and diblock copolymer of polyethylene glycol and polylactic acid (PLGA-PEG-PEG). Preferably, the polymer is poloxamer 407. In addition, optionally, the core aqueous solution, dissolution or dispersion may comprise water, a buffer pH solution, and/or salts.

In another prefer embodiment of the first aspect of the invention or of any of its preferred embodiments, the solid lipids are selected from the list which consists of: long chain fatty acids and their esters, such as stearic acid, palmitic acid, behenic acid, arachidonic acid, palmitostearate of glyceryl, disterate of glyceryl, dibehenate of glyceryl, cetilpalmitate, tristearate of glyceryl, trimyristin, tripalmitin; phospholipids such as phosphoglycerides and sphingolipids; acids and bile salts, such as taurocholate, deoxicholate, glycocholate, hiodeoxycholate, litocholate and similars. In another favorite embodiment of the first aspect of the invention or any favorite embodiment, the liquid lipids are selected from the list which consists of: chain fatty acids short and medium and its esters, as valeric acid, caproic acid, caprylic acid, capric acid, lauric acid, pelargonic acid, enantic acid, as well as triglycerides of caproic acid, capric acid caprylic acid, or lauroyl-polyoxyglycerides; tocopherol or other derivatives of vitamin E; as well as natural oils of vegetable or animal origin as olive, corn, sesame, cotton, soybean, sunflower, coconut, or cod liver oil.

In another prefer embodiment of the first aspect of the invention or of any of its preferred embodiments, the solid lipids are selected from the list consisting of: glyceryl disterate or glyceryl palmitosterate, trimyristin, triesterin and cholesterol and soy lecithin (which can be replaced by lecithin from egg or sunflower or corn); and the liquid lipids are selected from list consisting of: olive oil and triglycerides caprylic and capric acids (for example, the myglyol 812). For this specific formulation, the percentage by weight of reagents used here was approximately 50%, very similar to the formulation presented as example, in terms of size and zeta potential was also quite similar, as well as the amount of drug encapsulated. It must be noticed that for any of the favorite formulations of the present invention, you can substitute the olive oil for the coco as the sunflower oil. Even though the substitution of olive by the sunflower oil can reduce the amount of drug encapsulated to approximately 40%.

In another preferred embodiment, lipid layer is made of a mixture of glyceryl disterate in proportions ranging from 5-20%, preferably about 11.36%, with trimyristin between 5-20%, preferably around 11.36%, triesterin, between 5-20%, preferably about 11.36%, and cholesterol between 2-10%, preferably about 5.30% as solid components, and soy lecithin and blend of liquid components such as olive oil between 30-70%, preferably about 45.45% and triglycerides of caprylic and capric acids (for example the myglyol 812) 15.15% (preferably between a 10-20%). In this composition the percentage of each component, refers to its proportion in weight/weight percentage with respect to the total amount of lipids forming the layer.

In another preferred embodiment, the lipid layer is made of a mixture of glyceryl palmitate in proportions of 11.36% (preferably between 5-20%) with trimyristin to the 11.36% (preferably between 5-20%), triesterin 11.36% (preferably between 5-20%) and cholesterol 5.3% (preferably between 2-10%) as solid components, and soy lecithin and a blend of liquid components such as olive oil 45.45% (preferably between 30-70%) and triglycerides of caprylic acid and capric acids (for example the myglyol 812) 15.15% (preferably between a 10-20%). In this composition the % of each component, refers to its proportion in weight/weight percentage with respect to the total amount of lipids forming the cover.

In another preferred embodiment, the lipid layer coating the nucleus is formed by a mixture of dibehenate of glyceryl in proportions of 11.36% (preferably between 5-20%) with trimyristin to 11.36% (preferably between 5-20%), Tristearin 11.36% (preferably between 5-20%) and cholesterol 5.3% (preferably between 2-10%) as components Solids plus egg lecithin and mixture of liquid components such as olive oil 45.45% (preferably between 30-70%) and triglycerides of caprylic and capric acids (e.g. Myglyol 812) 15.15% (preferably between 10-20%). In this composition the percentage of each component, refers to its proportion in percentage weight/weight with respect to the total amount of lipids that form the cover.

In another preferred embodiment, the lipid layer coating the nucleus is formed by a mixture of dibehenate of glyceryl in proportions of 11.36% (preferably between 5-20%) with trimyristin to 11.36% (preferably between 5-20%), tristearin 11.36% (preferably between 5-20%) and cholesterol 5.3% (preferably between 2-10%) as solids components, and soy lecithin and a mixture of liquid components such as sunflower oil 45.45% (preferably between 30-70%) and triglycerides of caprylic and capric acids (e.g. Myglyol 812) 15.15% (preferably between 10-20%). In this composition the percentage of each component, refers to its proportion in percentage weight/weight with respect to the total amount of lipids that form the cover.

In another preferred embodiment, the lipid layer of the nucleus is formed by a mixture of glyceryl dibehenate in proportions of 11.36% (preferably between 5-20%) with trimyristin 11.36% (preferably between 5-20%), tristearin 11.36% (preferably between 5-20%) and cholesterol 5.3% (preferably between 2-10%) as solids components, and soy lecithin and a mixture of liquid components such as cod liver oil 45.45% (preferably between 30-70%) and triglycerides of caprylic and capric acids (e.g. Myglyol 812) 15.15% (preferably between 10-20%). In this composition the percentage of each component, refers to its proportion in percentage weight/weight with respect to the total amount of lipids that form the cover.

In a particularly preferred embodiment of the first aspect of the invention or any of its preferred embodiments, the mixture of liquid lipid and solid lipid is qualitatively, and optionally quantitatively, selected from any of the following (M1, M2, M3, and M6). In the table are expressed the mg of each component to obtain 220 mg of lipid mixture):

| M1 | | M2 | | M3 | M6 | |
|---|---|---|---|---|---|---|
| glyceryl dibehenate | 25 mg | glyceryl dibehenate | 75 mg | | glyceryl dibehenate | 37 mg |

-continued

| M1 | | M2 | | M3 | | M6 | |
|---|---|---|---|---|---|---|---|
| Trimyristate of glycerol | 25 mg | | | Trimyristate of glycerol | 37.5 mg | Trimyristate of glycerol | 25 mg |
| Tristearin | 25 mg | | | Tristearin | 37.5 mg | Tristearin | 25 mg |
| Cholesterol | 12 mg | Cholesterol | 12 mg | Cholesterol | 12 mg | | |
| Virgin olive oil | 100 mg | Virgin olive oil | 100 mg | Virgin olive oil | 100 mg | Virgin olive oil | 100 mg |
| Triglycerides caprylic and capric acid | 33 mg | TriglyceridescCaprylic and capric acid | 33 mg | Triglycerides caprylic and capric acid | 33 mg | Triglycerides caprylic and capric acid | 33 mg |

Preferably the lipid layer is formed by mixtures of the following solid and liquid lipids: Glyceryl dibehenate, glyceryl, Tristearin, Trimyristin, cholesterol, Virgin olive oil, capric and caprylic and liquid soy lecithin acid triglycerides.

In another preferred embodiment of the first aspect of the invention or of any of its preferred embodiments, the lipid soluble or lipid-dispersible surfactants, are selected from molecules surface-active with HLB values lower than 10 such as lecithin from soybean, egg, corn or sunflower with a HLB of 9.5, esters of glycerol monooleate (3.3), monoestearate (4.7) or monopalmitate (3.8) and Glycerin monolaurate (5.2), esters of sorbitane as the monooleate (4.3), the monoestearate (4.7) or monopalmitate (4.3).

In another favorite embodiment of the first aspect of the invention or of any of its preferred embodiments, the pegylated coating of the lipid layer includes polyethylene glycol (PEG) or PEG esters with other more hydrophobic components, as the tocopheryl succinate-PEG 1000 which allows anchoring PEG in lipid layer increasing its stability. Preferably, this layer also comprises water soluble or water dispersible surfactants (greater than 10 HLB). Preferably D-α acid tocopheryl polyethylene glycol 1000 succinate In another prefer embodiment of the first aspect of the invention or of any of its preferred embodiments, the system comprises one or several lysosomal enzymes and/or proteins that increase cell metabolism such as infliximab, abatacerpt, rituximab, adalidumab, etanercept, golimumab, certolizumab, sifalimumab, anifrolumab and the like. Preferably the loaded enzymes may be any of those employed in the treatment of diseases of deficit lysosomal or similars, such as elosulfasa alfa, velaglucerase, laronidase, idursulfase, galsulfasa, imiglucerase, agalsidase, Alfa sebelipase, Alfa cerliponase, velmanase, alglucosidase or N-acetyl glucosaminidase. These enzymes or proteins can be immobilized in the core and/or adsorbed on the surface, i.e., adsorbed on the pegylated lipid layer.

A second aspect of the invention refers to a method of preparation of the nanostructured lipid system of the invention, which comprises:

a Addition of an aqueous dissolution or dispersion containing a polymer that gels depending on temperature as for example poloxamer 407 and, optionally, further comprising one or several lysosomal enzymes or proteins that increase the cell metabolism such as infliximab, abatacerpt, rituximab, adalidumab, etanercept, golimumab, certolizumab, sifalimumab, anifrolumab and similar, to an oily phase comprising a mixture of solid and liquid lipids, in such a way that a top layer (the oily phase) and a bottom layer (aqueous phase) are formed; where the aqueous dissolution or dispersion constitutes the dispersed phase and the mixture of liquid and solid lipids the continuous or dispersing phase;

b Preparing a primary emulsion from the mixture obtained in stage a), such preparation can be performed by for example using ultrasonic homogenization;

c Increasing the temperature to produce the gelation of the dispersed phase of the primary emulsion obtained in stage b);

d. Adding to the gel system in oil emulsion resulting in C), a new external aqueous phase that comprises pegylants agents like polyethylene glycols, vitamin D or derivatives such as tocopherol-succinate-PEG 1000, hydrophilic colloids (natural hydrophilic polymer as polyvinyl alcohol . . . ) or peptides, and preparing a secondary emulsion, the emulsion can be made for example by using ultrasound homogenization, resulting in a multiple emulsion of the type aqueous gel in oil in water; and e Solidifying the lipid layer, by adding the resulting system of stage (D) to an aqueous dispersion of surfactants with HLB>10, preferably in an ice bath, the lipid layer is deposited on the surface of the gel particle forming the nanostructured lipid systems.

The nanostructured lipid system can be obtained as powdery solids that can be easily redispersed in an aqueous vehicle, giving rise to an aqueous dispersion of the NLC with appropriate characteristics for intravenous administration or for any further administration mode. To obtain the powdery solid drying techniques such as freeze drying or atomization may be used. In the case of freeze-drying, it is necessary to add cryoprotective agents to avoid the aggregation of the NLC which would prevent the correct re-dispersion. Cryoprotectant agents that can be used include sucrose, glucose, maltose, trehalose, sorbitol, cyclodextrins, glycerin, among others. For lyophilization, the NLC containing cryoprotective agents are frozen, preferably quickly, to then remove the water by freeze-drying.

In a preferred embodiment of the second aspect of the invention, the aqueous dissolution or dispersion of the stage a) comprises a thermogelling polymer selected in the list consisting of: poloxamer 407, chitosan, hydroxypropyl cellulose (HPC), hydroxypropylmethyl cellulose (HPMC) and diblock copolymer of polyethylene glycol and polylactic acid (PLGA-PEG-PEG). Preferably, the polymer is poloxamer 407. Additionally and optionally comprises an aqueous dissolution or dispersion can be understood as water, buffer solution of pH, and/or salts.

In another prefer embodiment of the second aspect of the invention or of any of its preferred embodiments, the solid lipids are selected from the list which consists of: long-chain fatty acids and their esters, such as stearic acid, palmitic acid, behenic acid, arachidonic acid, palmitostearate of glyceryl, disterate of glyceryl, dibehenate of glyceryl, cetylpalmitate, tristearate of glyceryl, trimyristin, tripalmitin; phospholipids such as phosphoglycerides and sphingolipids; acids and bile salts, such as taurocholate, deoxycholate, glicocholate, hiodeoxicholate, litocholate and similars. In another favorite embodiment of the second aspect of the invention or any favorite embodiment, the liquid lipids are selected from the list which consists of: short and medium chain fatty acids and its esters, as valeric acid, caproic acid, caprylic acid, capric acid, lauric acid, pelargonic acid, enanthic acid, as well as triglycerides of caproic acid, capric acid, caprylic acid, or lauroyl-polyoxyglycerids; tocopherol or other derivatives of vitamin E; as well as natural oils of vegetable or animal origin as olive, corn, sesame, cotton, soybean, sunflower, coconut, or cod liver oil.

In another prefer embodiment of the second aspect of the invention or of any of its preferred embodiments, the solid lipids are selected from the list consisting of: glyceryl disterate or glyceryl palmitosterate, trimyristin, tristearin, cholesterol and soy lecithin (which can be replaced by lecithin from egg or sunflower or corn); and the liquid lipids are select of the list consisting of: olive oil and triglycerides of caprylic and capric acids (for example the myglyol 812). For this specific formulation, the quantities, in percentage by weight, of reagents used was approximately 50%, similar to the formulation of the example, in terms of size and zeta potential was also quite similar, as well as the amount of drug encapsulated. It must be noted that for any of the favorite formulations of the present invention, you can substitute olive oil for coco or sunflower oil. Although the substitution of olive by the sunflower oil can reduce the amount of drug encapsulated to approximately 40%.

In another prefer embodiment, the lipid layer is made of a mixture of glyceryl disterate in proportions ranging from 5-20%, preferably about an 11.36%, with trimyristin between 5-20%, preferably approximately an 11.36%, tristearin, between 5-20%, preferably about an 11.36%, and cholesterol between 2-10%, preferably about a 5.30% as a solid components, and soy lecithin and blend of liquid components such as olive oil between 30-70%, preferably about a 45.45% and triglycerides of caprylic and capric acids (for example the myglyol 812) 15.15% (preferably between a 10-20%). In this composition the % of each component, refers to its proportion in weight/weight percentage with respect to the total amount of lipids forming the lipid layer.

In another prefer embodiment, the lipid layer is made of a mixture of glyceryl palmitate in proportions of 11.36% (preferably between 5-20%) with trimyristin to the 11.36% (preferably between 5-20%), tristearin 11.36% (preferably between 5-20%) and cholesterol 5.30% (preferably between 2-10%) as solid components, and soy lecithin and blends of liquid lipids such as olive oil 45.45% (preferably between 30-70%) and triglycerides of capric and caprilic acids (for example the myglyol 812) 15.15% (preferably between a 10-20%). In this composition the % of each component, refers to its proportion in weight/weight percentage with respect to the total amount of lipids forming the cover.

In another preferred embodiment, the lipid layer is made of a mixture of glyceryl dibehenate in proportions of 11.36% (preferably between 5-20%) with trimyristin to the 11.36% (preferably between 5-20%), tristearin 11.36% (preferably between 5-20%) and cholesterol 5.30% (preferably between 2-10%) as solid components, and lecithin egg and mixing of liquid liquids such as olive oil at 45.45% (preferably between 30-70%) and triglycerides of capric and caprilic acids (for example the myglyol 812) 15.15% (preferably between a 10-20%). In this composition the % of each component, refers to its proportion in weight/weight percentage with respect to the total amount of lipids forming the cover.

In another preferred embodiment, the lipid layer is made of a mixture of glyceryl dibehenate in proportions of 11.36% (preferably between 5-20%) with trimyristin to the 11.36% (preferably between 5-20%), tristearin 11.36% (preferably between 5-20%) and cholesterol 5.3% (preferably between 2-10%) as solid components, and soy lecithin and blend of liquid lipids such as oil sunflower 45.45% (preferably between 30-70%) and triglycerides of capric and caprilic acids (for example the myglyol 812) 15.15% (preferably between a 10-20%). In this composition the percentage of each component, refers to its proportion in weight/weight percentage with respect to the total amount of lipids forming the cover.

In another preferred embodiment, the lipid layer is made of a mixture of dibehenate of glyceryl in proportions of 11.36% (preferably between 5-20%) with trimyristin to the 11.36% (preferably between 5-20%), tristearin 11.36% (preferably between 5-20%) and cholesterol 5.3% (preferably between 2-10%) as solid components, and soy lecithin and blend of liquid components as cod liver oil % 45.45 (preferably between 30-70%) and triglycerides caprylic and capric acids (for example the myglyol 812) 15.15% (preferably between a 10-20%). In this composition the percentage of each component, refers to its proportion in weight/weight percentage with respect to the total amount of lipids forming the cover.

In a particularly preferred embodiment of the second aspect of the invention or of any of its preferred embodiments, the liquid and solid lipid mixture of the oil phase of the stage a) is qualitatively, and optionally quantitatively, selected from any of the following (M1 and M2, M3, M6). In the table the mg of each component for 220 mg of lipid mixture are expressed:

| M1 | | M2 | | M3 | | M6 | |
|---|---|---|---|---|---|---|---|
| Glyceryl Dibehenate | 25 mg | Glyceryl Dibehenate | 75 mg | | | Glyceryl Dibehenate | 37 mg |
| Glyceryl Trimistiate | 25 mg | | | Glyceryl Trimistiate | 37.5 mg | Glyceryl Trimistiate | 25 mg |
| Tristearin | 25 mg | | | Tristearin | 37.5 mg | Tristearin | 25 mg |
| Cholesterol | 12 mg | Cholesterol | 12 mg | Cholesterol | 12 mg | | |
| Virgin olive oil | 100 mg | Virgin olive oil | 100 mg | Virgin olive oil | 100 mg | Virgin olive oil | 100 mg |
| Triglycerides Caprylic and capric acid | 33 mg | Triglycerides caprylic and capric acid | 33 mg | Triglycerides caprylic and capric acid | 33 mg | Triglycerides caprylic and capric acid | 33 mg | liquid lipids such as olive oil 45.45% (preferably between 30-70%) and triglycerides of capric and caprilic acids (for example the myglyol 812) 15.15% (preferably between a 10-20%). In this composition the % of each component, Preferably the oily phase of the stage a) is made up of mixtures of solid and liquid lipids as following: cholesterol, olive oil, glyceryl dibehenate, glyceryl, tristearin, trimyristin capric and caprylic acid triglycerides and liquid soy lecithin.

In another preferred embodiment of the second aspect of the invention or of any of its preferred embodiments, the lipid soluble or lipid dispersable surfactants are selected from surface-active molecules with HLB values lower than 10 such as solid or fluid soy lecithin or egg lecithin with HLB of 9.5.

In another prefer embodiment of the second aspect of the invention or of any of its preferred embodiments, the new external aqueous phase comprises polyethylene glycol, or PEG esters with other more hydrophobic components, as tocopherol succinate-PEG 1000 which allows anchoring PEG in the lipid layer increasing its stability. Preferably, the aqueous phase also comprises water soluble or water dispersible surfactants in (HLB>10). Preferably are D-α acid tocopheryl polyethylene glycol 1000 succinate In another prefer embodiment of the second aspect of the invention or of any of its preferred embodiments, the system comprises one or several lysosomal enzymes or proteins that increase cell metabolism such as infliximab, abatacerpt, rituximab, adalidumab, etanercept, golimumab, certolizumab, sifalimumab, anifrolumab and similars. Preferably, loaded enzymes may be any of those employed in the treatment of lisosomal storage diseases or similar, such as elosulfasa alpha, velaglucerase, laronidase, idursulfase, galsulfasa, imiglucerase, agalsidase, alfa sebelipase, alfa cerliponase, velmanase, alglucosidase or N-acetyl glucosaminidase. These enzymes or proteins can be immobilized in the nucleus core and/or adsorbed on the surface, i.e., adsorbed on the pegylated lipid layer.

A third aspect of the invention is related to the lipid nanostructured system that can be obtained according to the second aspect of the invention.

A fourth aspect of the invention is related to the nanostructured lipid system of the first aspect of the invention or the third aspect of the invention, to be used as a pharmaceutical composition.

A fifth aspect of the invention relates to the nanostructured lipid system of the first aspect of the invention or the third aspect of the invention, where the system comprises one or several lysosomal enzymes, and it may be used for the treatment of a lysosomal storage diseases.

In a prefer performance of the fifth aspect of the invention, Lysosomal Storage Disease is the Hurler, Herler-Scheie, disease or the disease of Scheie, and at least one of the Lysosomal enzymes is the Laronidase.

In another prefer performance of the fifth aspect of the invention, Lysosomal Storage Disease is the disease of Hunter, and at least one of the Lysosomal enzymes is idursulfase [Elaprase®].

In another prefer performance of the fifth aspect of the invention, Lysosomal Storage Disease is the Morquio disease, and at least one of the Lysosomal enzymes is the elosulfase alfa.

In another prefer performance of the fifth aspect of the invention, Lysosomal Storage Disease is syndrome Maroteaux-Lamy, and at least one of the Lysosomal enzymes is the Galsulfase.

In another prefer performance of the fifth aspect of the invention, Lysosomal Storage Disease is the disease of Gaucher, and at least one of the Lysosomal enzymes is the imiglucerase.

In another prefer performance of the fifth aspect of the invention, the Lysosomal Storage Disease is the disease of Fabry, and at least one of the Lysosomal enzymes is the Agalsidase b or agalsidase.

In another prefer performance of the fifth aspect of the invention, Lysosomal Storage Disease is the disease of Pompe, and at least one of the lysosomal enzymes is the alglucosidase.

In another prefer performance of the fifth aspect of the invention, Lysosomal Storage Disease is the Mucopolysaccharidosis Type IIIB, and at least one of the lysosomal enzymes is the N-acetyl glucosaminidase (see A Treatment Extension Study of Mucopolysaccharidosis Type IIIB, Drug: BMN 250).

It must be noted that other Lysosomal Storage Diseases and the enzymes suitable to treat them are included in the background of the present invention. These enzymes can also be loaded within the nanostructured lipid system of the first aspect of the invention to treat the associated disease.

In addition, the nanostructured lipid system of the invention may serve not only to treat lysosomal diseases but as it is illustrated in the FIGS. 31 to 35, and 37 to 38 and depending on the type of loaded protein, can be also used to the treatment or prevention of degeneration of the cartilage or bone, and therefore, this system could prevent or treat diseases such as osteoarthritis, rheumatoid arthritis and erythematosus lupus or traumatic origin. Enzymes particularly useful for the said treatment or prevention of degeneration of the cartilage in the nanostructured lipid system of the invention can be selected from the list consisting of: Laronidase [Aldurazyme®], idursulfase [Elaprase®], elosulfase alfa, and alfa vestronidasa [Mepsevii®]. An enzyme particularly useful for the said treatment or prevention of degeneration of the bone in the nanostructured lipid system of the invention is elosulfase alfa.

Finally, the nanostructured lipid system of the invention can be administered by any suitable route such as Intramuscular, intravenous, bolus, arterial, and subcutaneous administration. In case, the subcutaneous administration is chosen, and as illustrated in the examples, a surfactant must be use such as, but not limited to, bile salts, deoxicholate, taurocholate, glycocholate, hiodeoxycholate, litocholate, lecitins such as soy, egg, corn, sunflower, or poloxamers such as 188 or 407). A surfactant must be use in a concentration ranging from 0.5 to 2% wt/total volume to be administered. The best results in obtaining a stable homogeneous suspension were achieved with sodium taurocholate (1% in saline solution). The size of NLC after resuspension in sodium taurocholate was checked and remained in the range between 300-400 nm.

The following examples serve merely for the purpose of illustrating the present invention and may not serve to limit the present invention.

EXAMPLES

Example 1

1.1. Formulation as an Example of (Formulation 1) Nanostructured Lipid System of the Invention.
Lipids:
  75 mg of glyceryl behenate;
  75 mg of microcrystalline trimyristin;
  75 mg microcrystalline tristearin;
  35 mg cholesterol;
  w/v 300 μl oil virgin olive; and
  100 μl w/v of capric and caprylic acid triglycerides.
Surfactants
  250 mg p/v liquid soy lecithin; and
  500 mg Poloxamer 188

Aqueous Phase
   600 μL of poloxamer 407 prepared to 35% (Sigma Aldrich) in water.
   400 μL elosulfase alfa (Vimizim® 1 mg/mL, Biomarin).
Aqueous Phase
   600 μL of succinate, D-α-tocopherol polyethylene glycol 1000 prepared at 0.5% (Sigma Aldrich).
Preparation Lipids are dissolved in dichloromethane. A poloxamer 407 aqueous dispersion at 35% with the enzyme (in this case elosulfase alfa to treat Morquio) is prepared, mixed with lipids solution and homogenized by sonication with a ultrasonic probe (could be replaced with high pressure homogenizer) for 5 minutes. After this time, the second phase containing succinate of D-α tocopherol poliethyleneglycol 1000 prepared at 0.5% in PBS is added and homogenized for 10 minutes. Finally, the mixture is added to a dissolution of poloxamer at 188 5% in PBS.

FIG. 1 shows an example of the size distribution of nanostructured lipid systems (NLC), determined by DLS.

Figure 2:
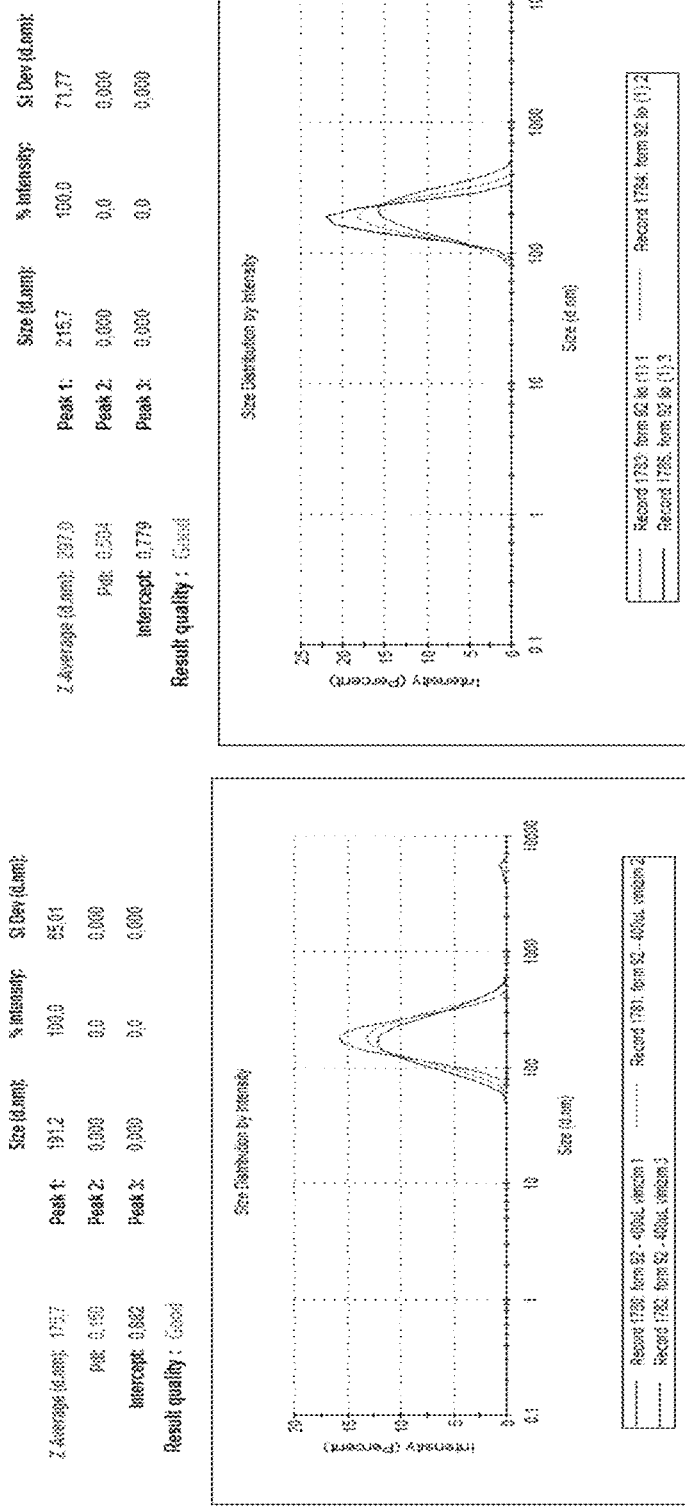
FIG. 2 Example of the particle size before and after freeze drying and reconstitution of formulations.
Figure 3:
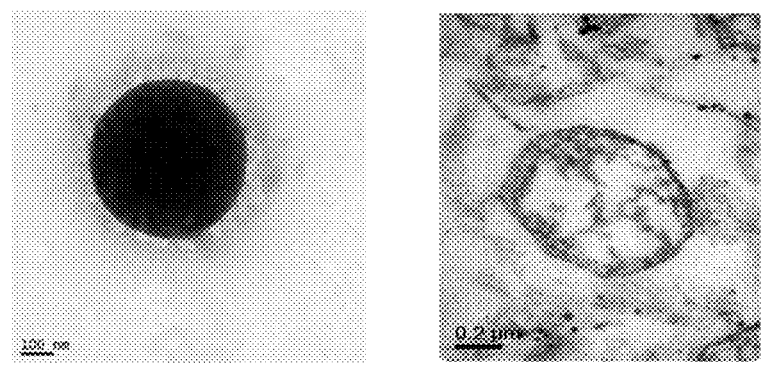
FIG. 3 Transmission electron microscopy Images (TEM) of the lipid nanostructured carriers: (left) external morphology; (Right) internal structure of the NLC containing enzyme.

To preserve the NLC formulation, particles are ultracentrifugated at 35000 rpm for 25 minutes at 14-20° C., the supernatant is removed and the NLC resuspend in a water solution containing a cryoprotectant (e.g. glucose, sorbitol, sucrose, cyclodextrins . . . ). The obtained dispersion is frozen by submerging it in liquid nitrogen (−60 to −80° C.) to be freeze-dried. The lyophilized solid powder is stored in dry and cool environment. FIG. 2 illustrates an example of the particle size before and after freeze-drying and reconstituted the formulations and FIG. 3 shows images of transmission electron microscopy (TEM) of the nanostructured lipid systems in which the external and internal morphology of the NLC containing the enzyme can be observed.

Figure 4:
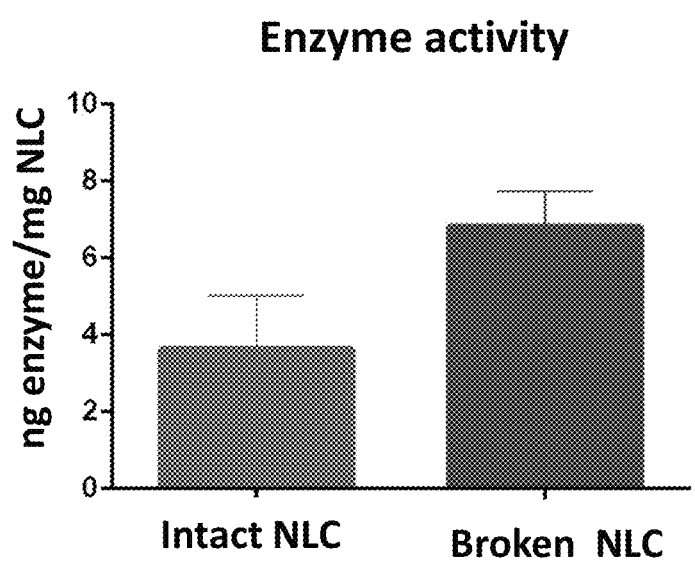
FIG. 4 Enzyme activity before and after NLC breakage, enzyme release and recovery.

To determine the degree of immobilization of enzyme in the NLC, the enzyme activity in these systems before and after breaking them was assessed to quantify the amount of enzyme could be adsorbed in the surface or immobilized in the core of the particles. The enzyme activity was determined by fluorimetry techniques describes in "*Practical and reliable enzyme test for the detection of Mucopolysaccharidosis IVA (Morquio Syndrome type A) in dried blood samples*"." To break the particles and release the immobilized enzyme from the gelled nucleus, NLC were treated with Triton X 100. Results are shown in FIG. 4.

1.2. Stability of the NLC in Human Plasma

Figure 5:
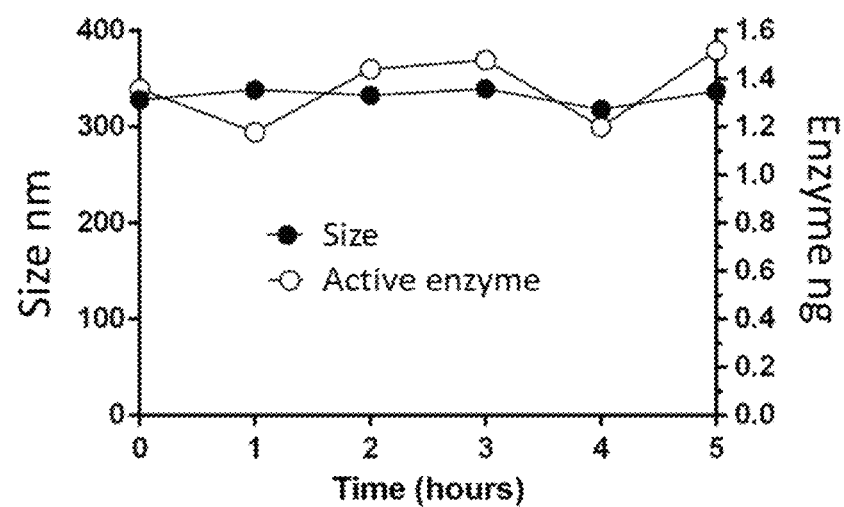
FIG. 5 NLC particle size and enzyme activity of the NLC containing Alpha elosulfasa after different times of incubation in human plasma. The graphs show the stability of the enzyme and the NLC in the presence of plasma.

The stability in plasma of the enzymes immobilized on the NLC was determined to quantify the level of protection against proteases. This assay is performed by incubating the NLC in plasma samples from 20 healthy patients at different time. Plasma samples were extracted each hour and NLC were isolated by ultracentrifugation. Samples of NLC were resuspended in water and the size and adsorbed enzyme activity remnant was measured (FIG. 5). As can be seen, the activity of the enzyme was maintained for at least five hours in the two compositions of NLC studied.

1.3. Study of Cellular Internalization of the Cell Line of Chondrocytes TC28a2 Nanostructured Lipid Systems.

The ability of internalization of the NLC 1.1 example containing the enzyme in chondrocytes TC28a2 cell lines was studied and also, the capacity of internalization of the NLC and intracellular enzyme release was determined.

Figure 6:
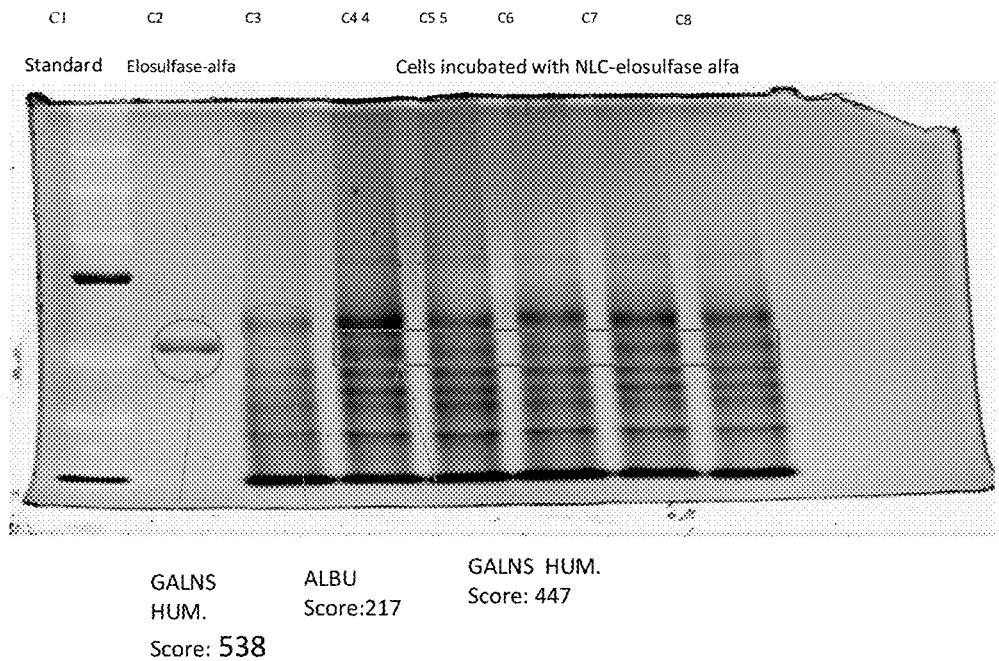
FIG. 6 Electrophoresis in acrylamide gel: Lane 1—standard molecular sizes. Lane 2—free enzyme (elosulfase alfa (GALNS)). 3—protein extract of chondrocyte cells untreated (Street cell line TC28a2). 4-5-6-7-8: different samples of protein extracts of cells incubated with various NLC with immobilized elosulfase alfa. All of them shows the protein band appearing in lane 2 corresponding to the elosulfasa alfa with the exception of 3 which includes the untreated cells.

Chondrocytes were seeded in plates and incubated for an hour in the presence of 150 mg of reconstituted freeze-dried NLC. Cells were detached by trypsin and after several washings, cells were lysed ultrasonically and the protein extract recovered. The total amount of protein is determined by the method of LOWRY (Biorad kit; protocol catalog #500-0119). Then, polyacrylamide electrophoresis gel was loaded with the same amount of protein and reveals with stained Sypro. A standard molecular weights, the free enzyme, and cells without trying were also included. The result is shown in FIG. 6. All the formulations, the standard and the free enzyme showed the protein band corresponding to the elosulfase alfa with the exception of the cells without treatment.

Figure 7:
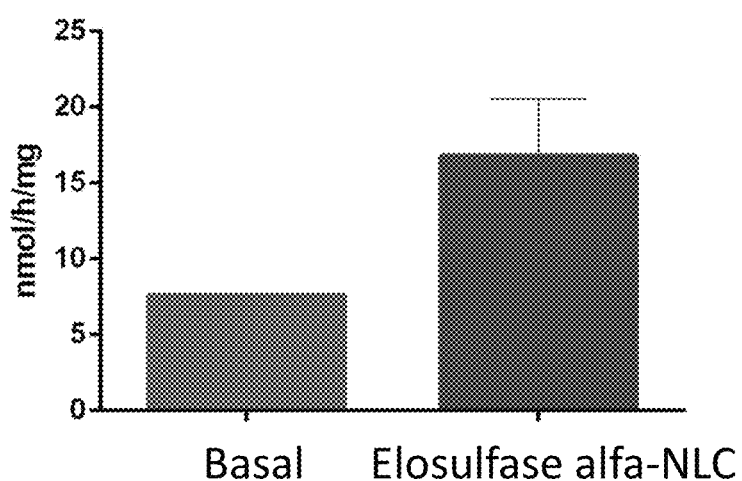
FIG. 7 Enzyme activity (Galactose 6-sulphate-sulphaatase and its recombinant enzyme elosulfasa alfa) found in chondrocytes of the cell line TC28a2 after incubation with the enzyme immobilized on NLC and in its comparison with the basal activity.

The same samples were also analyzed by fluorimetry techniques for determining the enzyme activity using the method describes in "*Practical and reliable enzyme test for the detection of Mucopolysaccharidosis IVA (Morquio Syndrome type A) in dried blood samples*". The results are illustrated in FIG. 7 in which it ca be observed an increase in enzyme activity of the cell treated with NLC compared to untreated cells (differences significant p<0.05, test t). These results indicate the internalization of the NLC and the intracellular release of the enzyme in its active form.

Figure 8:
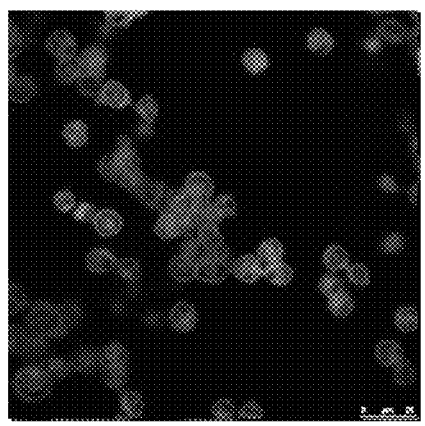
FIG. 8 Results of the internalization study in chondrocytes by confocal microscopy. In the photographs it can be seen red points (NLC) inside cells (stained green). (A) Images after incubation of the cells with NLC for 1 hour at 37° C. B) 2 hours of incubation at 37° C. and C) 1 hour incubation at 4° C.
Figure 8:
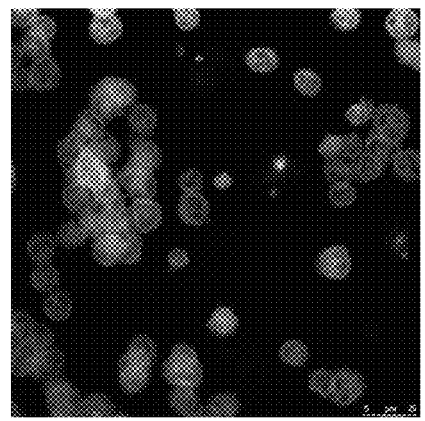
Figure 8:
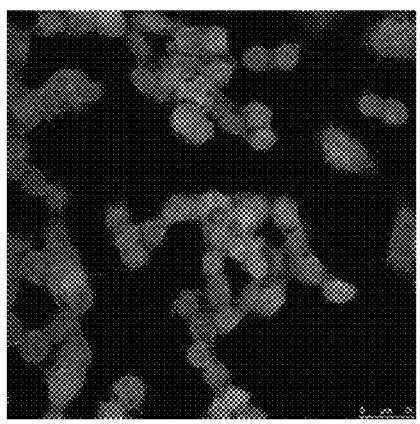

To study the internalization of the NLC in chondrocytes, confocal laser microscopy and transmission (TEM) electron microscopy techniques were used. For confocal microscopy, the NLC containing the elosulfase alfa were stained with DID (probe that stain lipids in red) and incubated in the co-culture of chondrocytes during variable time to 37° C. or 4° C. Images obtained by confocal microscopy are display in FIG. 8. It shows small red areas (corresponding to the NLC with elosulfase Alfa) inside cells which are stained in green. Using this technique NLC inside of the chondrocytes from 30 min of incubation at 37° C. as at 4° C. were observed. FIGS. 8 A and 8 B shows the result at 37° C. after 1 and 2 hours of incubation and in FIG. 8 *c* to 4° C. after 1 hour of incubation.

Figure 9:
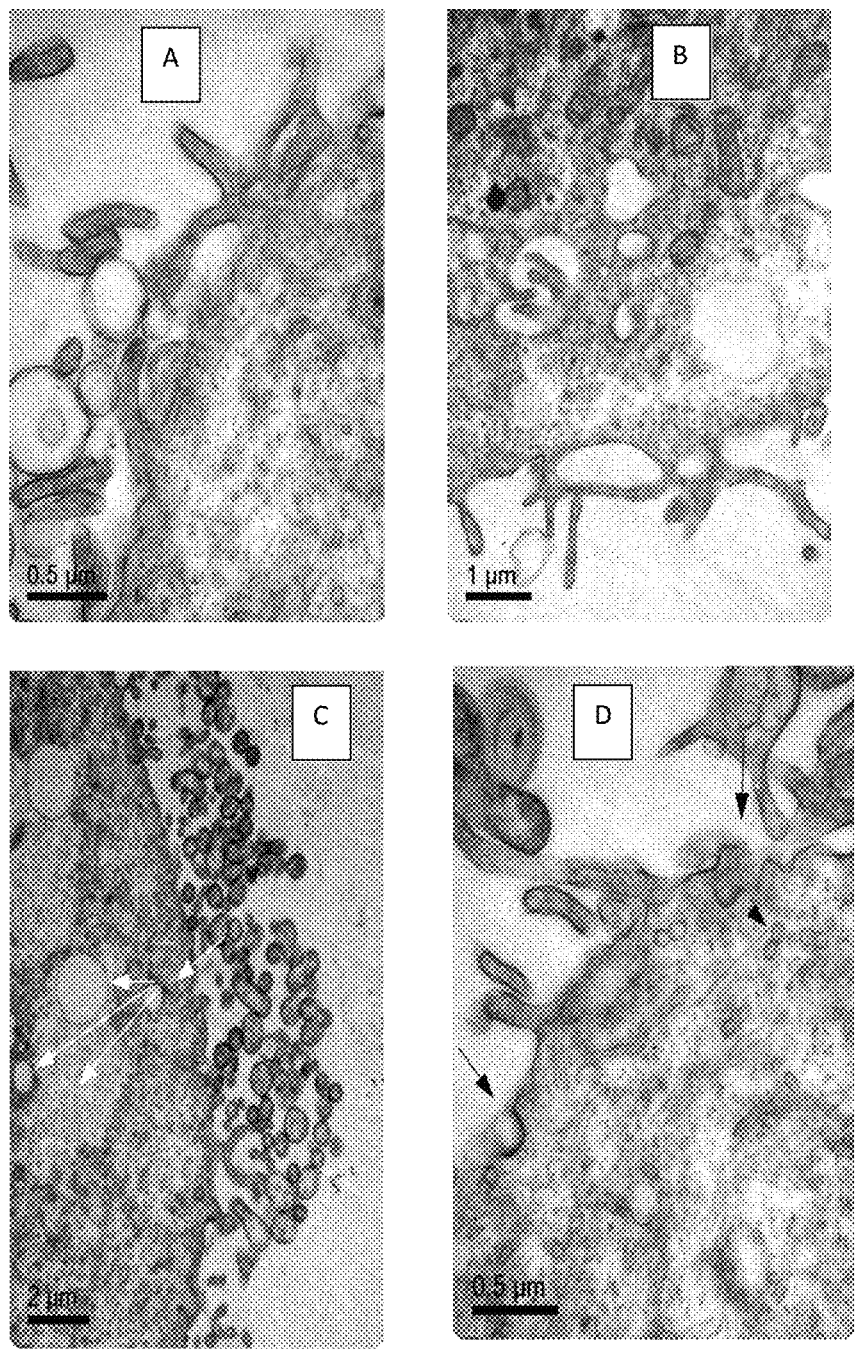
FIG. 9 Transmission Electron Microscopy pictures of chondrocytes incubated with the NLC containing elosulfase alfa after 1 h of incubation at 37° C. It is observed in the surface of chondrocytes the formation of typical invaginations associated to the process of pinocytosis and phagocytosis and the NLC; ((B) it is observed NLC inside cells after its internalization through these mechanisms; C and D) it is observed the internalization of the NLC through mechanisms associated with endocytosis.
Figure 10:
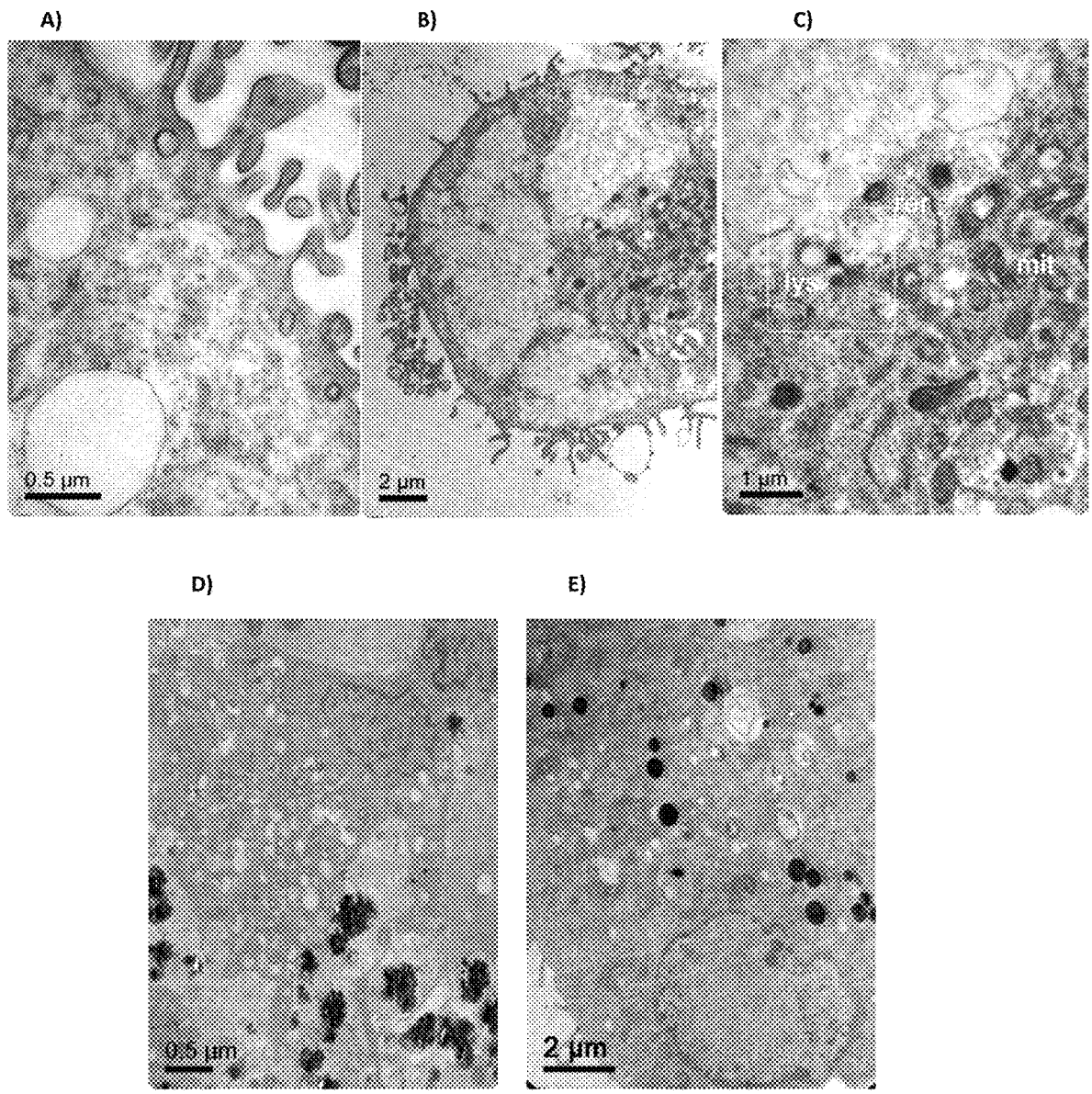
FIG. 10 Transmission electronic microscopy images of chondrocytes incubated with the NLC containing elosulfase Alfa after 1 h of incubation at 37° C. In figures A and B the formation of vesicles within the cell as a result of the internalization of the NLC is observed, in C, the fusion with Lysosomes, and in D and E the NLC in the interior of the Lysosomes after 3 and 6 hours of incubation.

As confirmation assay, acquisition of images of fixed cells by transmission (TEM) electron microscopy was obtained. Cells incubated for 1 hour in the presence NLC with enzyme were immobilized and observed by TEM. The images are shown in FIG. 9. In summary, it can observe the internalization of NLC in chondrocytes by phagocytosis or pinocytosis by establishing invaginations that surround and internalize the NLC (A and B). Also, it is possible to observe some of the NLC internalizing through (C) and (D) by endocytosis. Once inside the cytoplasm, vesicles are formed, which are gradually trapped by lysosomes (FIG. 10).

1.4. Study of Cellular Internalization of the Lipid Nanostructured Systems in Samples from Healthy Donors' Cartilage.

For these studies, samples of cartilage tissue obtained after traumatology surgery of two donors without metabolic diseases were used. The studies consisted in the incubation of the tissue in a culture containing the NLC with elosulfase alfa at different times and their study through TEM and proteomic techniques to determine the biological functions expressed by protein before and after treatment.

Figure 11:
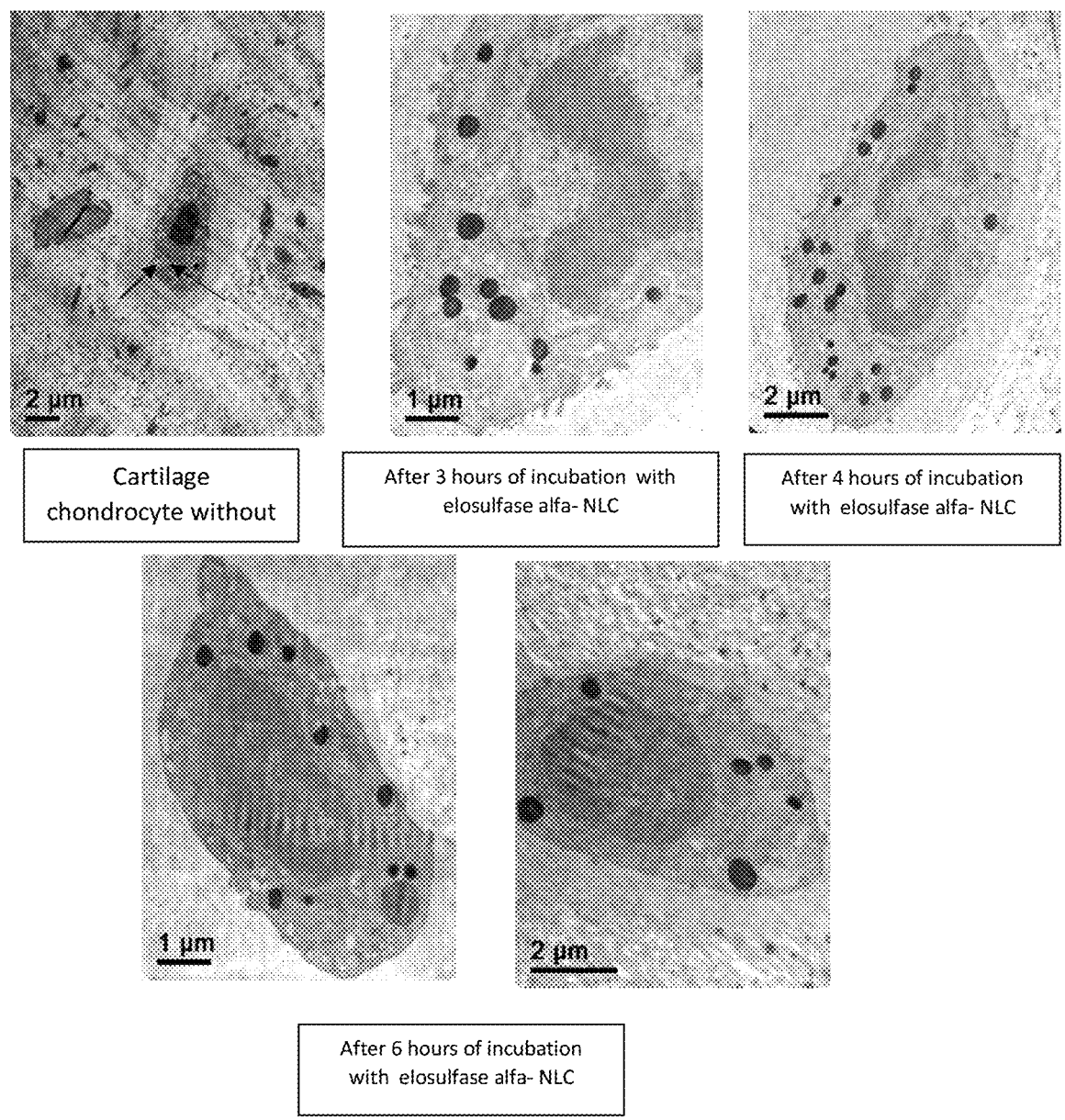
FIG. 11 Transmission electronic microscopy image of the cartilages without treatment and incubated with the NLC containing elosulfase alfa after 3, 4, and 6 hours of incubation at 37° C. The images correspond to cells that are taking part of the cartilage tissue. In untreated sample images there is observed a macrophage that contains several deposits of GAGs inside (pale grey, arrow) and in the treated samples it is observed the internalization of NLC into GAGs deposits that increase in size and become black as a result of the lipids accumulation.

Study of Internalization by Transmission Electron Microscopy:

FIG. 11 shows TEM microphotographs of chondrocytes in cartilage tissue. Chondrocytes with lysosomes and natural deposits of typical GAGs of healthy cells (small spots of light gray) are observed in untreated tissue. After 4-6 hours of treatment, the NLC internalized in deposits inside the cells is observed which acquired greater volume and a black color due to lipids.

Cartilage Proteomic Study

Figure 12:
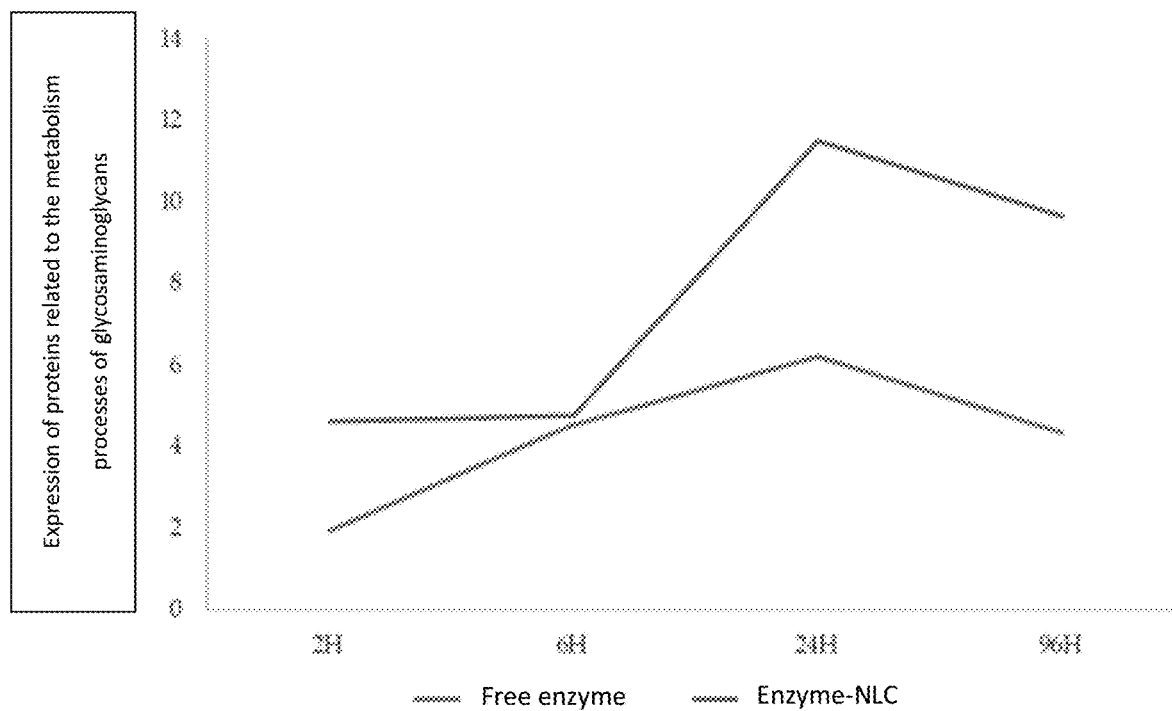
FIG. 12 Comparison of the amount of proteins related to the processes of synthesis, catabolization and metabolization of the keratan sulfate, expressed in cartilage cells at different times. The keratan sulfate is a glycosaminoglycan of Morquio related disease. The figure shows that treatment with the enzyme immobilized on NLC produces a greater expression of proteins that free elosulfase alfa, despite enzyme is in 2000 times lower concentration in NLC.

Cartilage was treated and analyzed using proteomic techniques by a triple TOF 6600 for the analysis of data. This process was conducted with the aim to compare normal tissue with a second group consisting of cartilage incubated with NLC that were not including enzyme, a third group made up of cartilage tissue incubated with the enzyme elosulfase alfa at a dose of 100 µg/100 µL, and finally, a fourth group constituted by the cartilage tissue incubated with elosulfase alfa immobilized on the NLC to an approximate dose of 50 ng of enzyme/1004 (2000 times lower than the free enzyme concentrations). The time of treatment of cells with each of the above systems (NLC, free and NLC immobilized enzyme) was 2 hours, 6 hours, 24 hours and 96 hours. In FIG. 12 it is shown the total expression of proteins related to the processes of synthesis and metabolism of the Keratan sulfate and glycosaminoglycan that accumulates in lysosomes of Morquio A patients.

Figure 13:
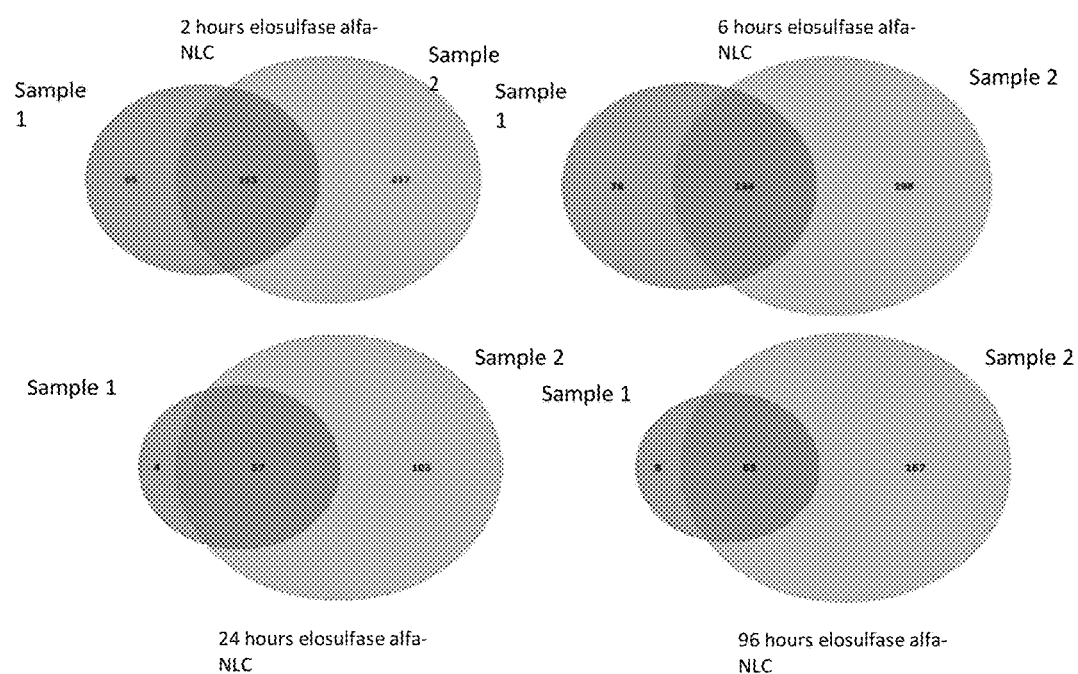
FIG. 13 Venn diagrams which identify the sharing protein expression between the tissues from the two donors treated at different times with inmovilized elosulfasa alfa. These diagrams identify the common processes to analyze the changes produced by the same treatment in both tissues.
Figure 14:
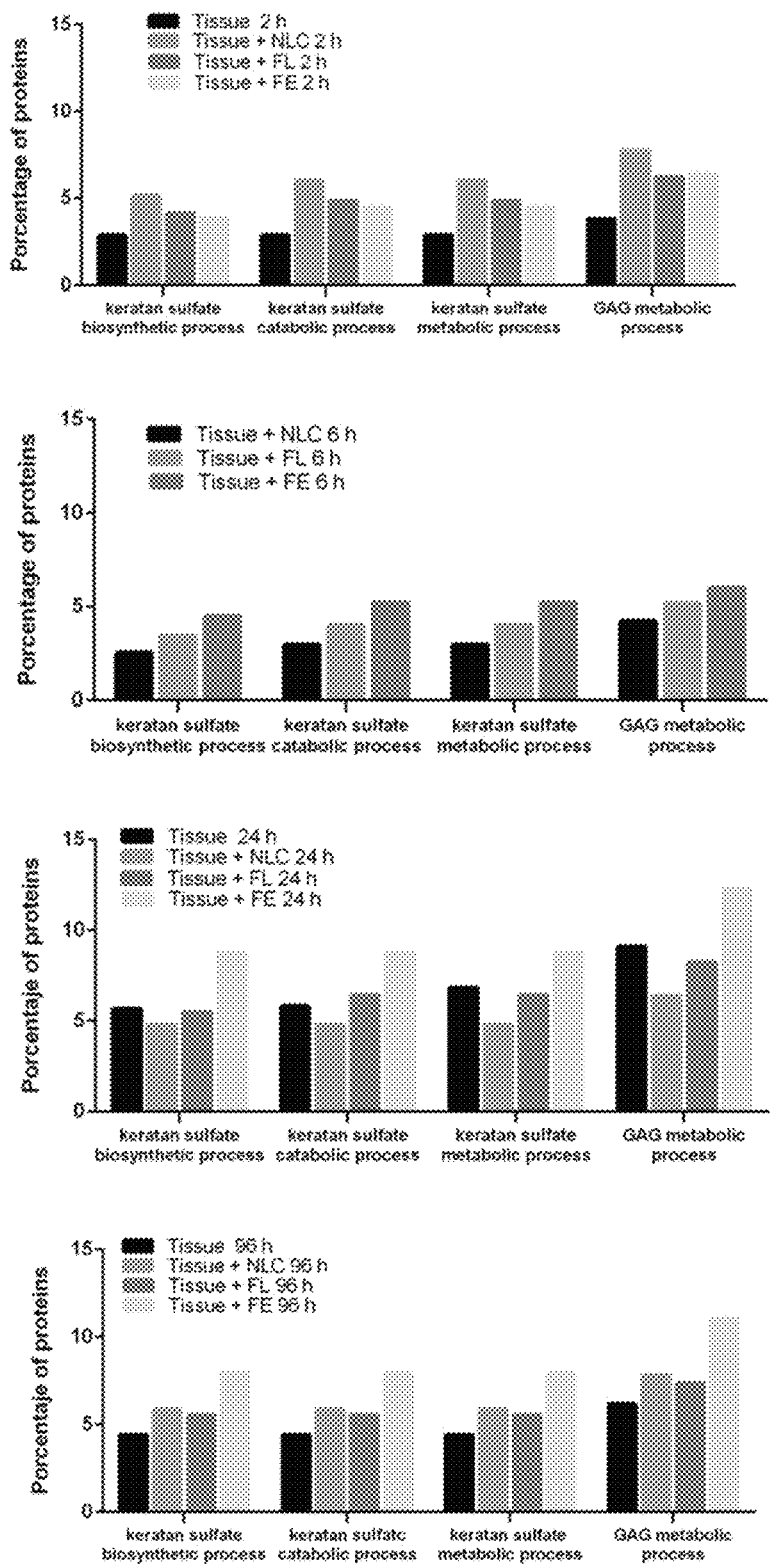
FIG. 14 This figure represents the expression of proteins (%) at different times of the biological processes involved in biosynthesis, catabolism and metabolic processes of glycosaminoglycans and the keratan sulfate metabolism. In all cases and for all the times investigated, a greater expression of proteins is observed in tissues incubated with elosulfase alfa immobilized on NLC, despite of the enzyme concentration is 2000 times lower than the free enzyme solution.

In order to analyze the results obtained from samples tissue of the two donors, Venn diagrams were used to find out similarities in the protein expression in tissue after treatment with the NLC (FIG. 13) and a new proteomic analysis was performed from the similarities. FIG. 14 shows examples of the expression of some proteins related to the biological function of processes of biosynthesis, catabolization and metabolization of keratan sulfate, which are those that are altered in disease of Morquio A. Tissue treated with the elosulfasa immobilized on the NLC produces a greater expression of biological functions related to this glycosaminoglycan, even longer times (96 hours) and taking into account the lowest dose of enzyme used in the treatment with the immobilized alfa elosulfasa (2000 times lower concentration than in the treatment with the free enzyme)

The administration of the elosulfase alfa in NLC also produces an increase in the expression of proteins from biological processes related to the development and growth of the cartilage (FIG. 31), the extracellular matrix (FIG. 32) and collagen (FIG. 33) in the healthy donors samples of cartilage treated at different times. This increase in the protein expression indicates an increase in the synthesis of these molecules that are closely related with the regeneration of connective tissue. Also, the immunohistochemical results made using a functional test indicates that the enzyme immobilized in NLC induces an increase of the protein lumican expression in fibroblasts from healthy and patients of Morquio tissues samples, indicating its potential to promote the this type of tissue repair and regeneration processes.

1.5. Study of Cellular Internalization of Lipid Systems Nanostructured in Samples of Tonsil Surgery of Patients Diagnosed with the Disease of Morquio.

Tonsil tissue from a patient diagnosed with Morquio A was used. The samples were donated after tonsillectomy surgery. The donor (5 years of age) was treated with Vimizim® (elosulfase Alfa) over a period of a year and a half. For performing this study, the tissue was extracted and the cells were isolated from the tissue using techniques of explants.

Cells or tissues were incubated for two hours in a medium containing immobilized elosulfase alfa in NLC, the internalization was studied by transmission electron microscopy and the keratan sulfate that was accumulated in deposits before and after treatments were quantified.

Figure 15:
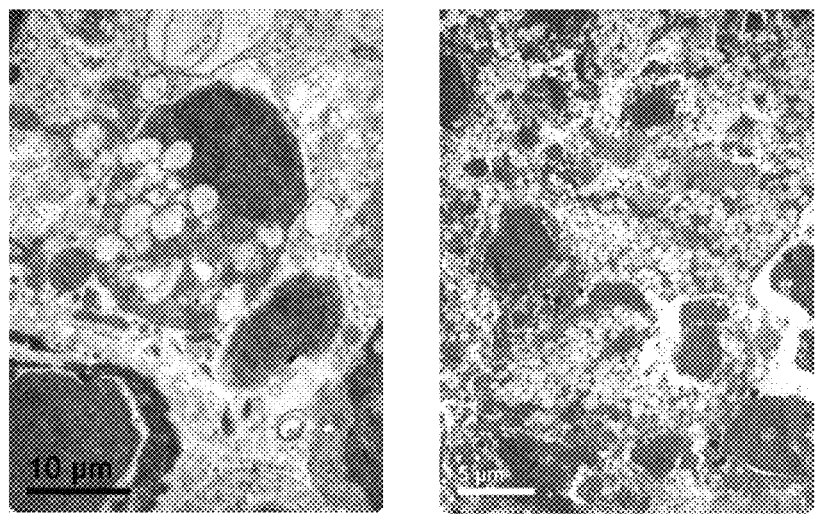
FIG. 15 Microphotographs obtained by transmission electronic microscopy of tissue specimens from the tonsil of a patient diagnosed with Morquio A disease. The images show macrophages with spherical grey deposits of keratan sulfate, which are characteristic of the disease.
Figure 16:
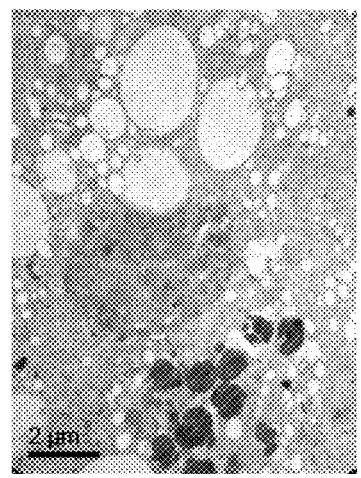
FIG. 16 Microphotographs obtained by transmission electronic microscopy of tissue specimens from the tonsil of a patient diagnosed with Morquio A disease after one hour (photo above left) and two hours of incubation (rest of images) with NLC containing immobilized elosulfase Alfa. A progressively keratan sulfate deposits change to black color and an increase in size is observed as a result of the accumulation the NLC in the Lysosomes.
Figure 16:
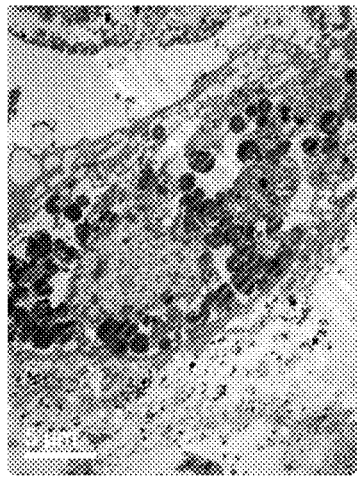
Figure 16:
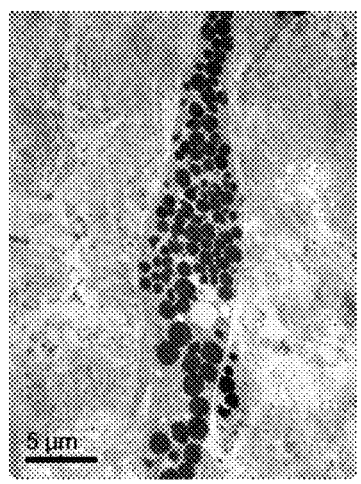
Figure 16:
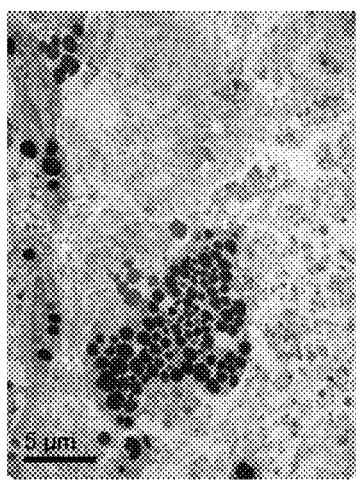

Study of Internalization by Transmission Electron Microscopy:

The TEM microphotographs obtained from the tissue before and after the treatments are shown in FIGS. 15 and 16. The photomicrographs of untreated tissue shows macrophages with large amount of GAGs deposits (keratan sulfate), appearing as rounded grey spots, which are typical of this disease. The presence of a large number of these deposits in macrophages suggests that treatment of the patient with Vimicin® is not at completely effective. In FIG. 16 tissue samples incubated for one hour with the NLC containing immobilized enzyme are shown. It can be observed a progressive change in the color of the deposits, from light gray to black, as the time of incubation was increased (top right figure 1 hour and two hours of incubation, the rest). This change occurs because of the internalization and the progressive accumulation of the NLC in the interior of the lysosomes. Lipids-forming the NLC are much more dense molecules to electrons than glycosaminoglycans, so this is the reason why they appear as dark spots.

Quantification of Enzyme Activity

Figure 17:
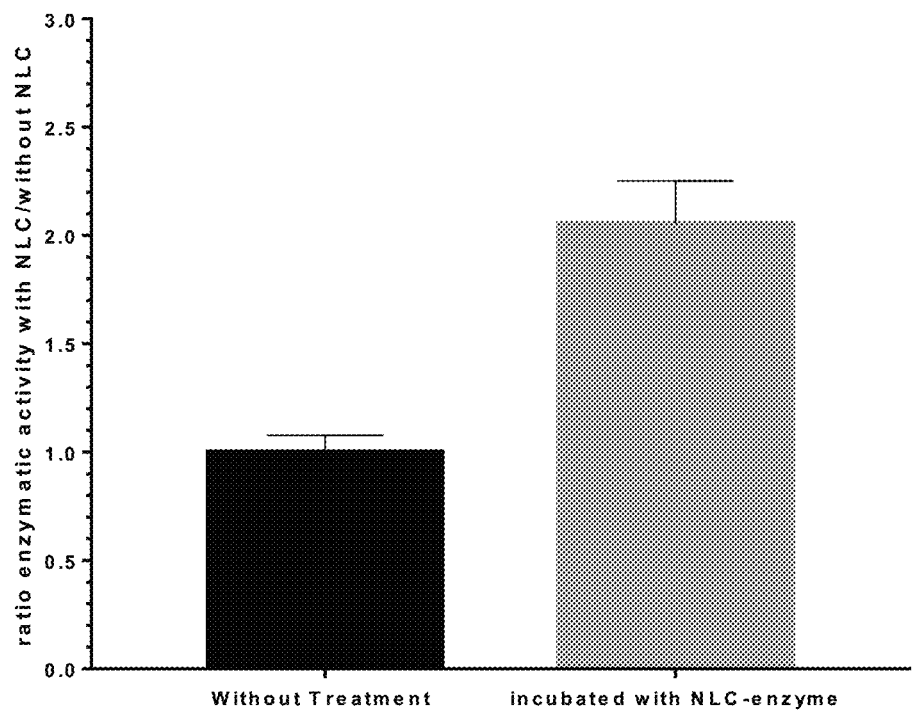
FIG. 17 Relationship between the enzymatic activity of the untreated cells and the cell incubated with NLC containing elosulfase Alfa. A significant increase in the cell enzyme activity is observed after incubation with the NLC immobilized drug.

Enzymatic activity of cell and tissue samples was determined using the same techniques used previously in section 1.3. The results are shown in FIG. 17, where it is observed a two-folder increase in cell enzyme activity tissues when incubated with elosulfasa alfa immobilized on NLC compared to untreated tissue.

1.6.—Study of Biodistribution In Vivo of the NLC Containing Elosulfase Alfa in Mouse Model, after the Intravenous Bolus.

To determine the in vivo distribution, the NLC containing the enzyme was administered intravenously to animals.

For these set of studies, different formulations were used: the formulation NLC described in paragraph 1.1 of the example 1, and a second formulation with identical composition but in this case, the amount of D-succinate α-tocopherol polietileneglicol 1000 was increased to enhance the degree of surface pegylation. To carry out the experiment, the NLC were stained with fluorophore DID and administered by injection at mice in the tail lateral vein. 24 hours after administration the animals were euthanatized and the organs and tissues were extracted for studies by confocal fluorescence microscopy and transmission electron microscopy (TEM).

Figure 18:
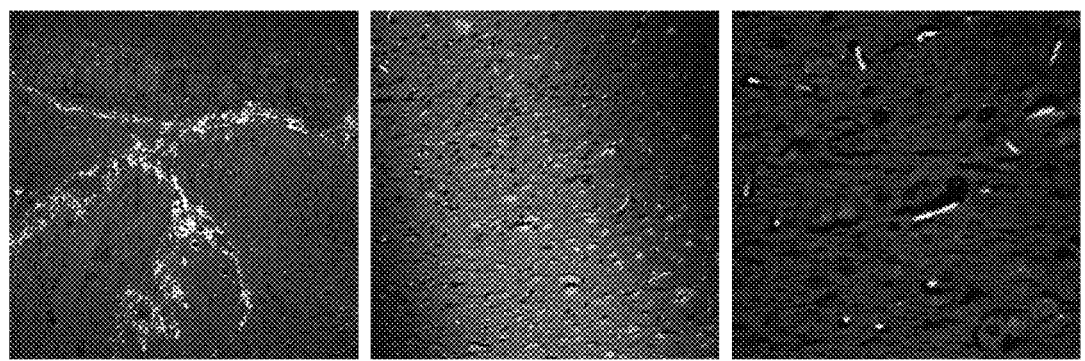
FIG. 18 Fluorescence confocal microscopy images of mouse brain samples 24 hours after intravenous administration of the NCL. The images are taken at different magnifications.

Confocal microscopy images confirmed the presence of NLC in all analyzed tissues, including the lung, kidney, liver, spleen, skeletal muscle and tissue of the central nervous system. As example, in FIG. 18, the results of confocal microscopy study corresponding to a small section of the brain are shown. NLC in brain tissue indicates that these systems have been able to cross the blood brain barrier (BBB).

Figure 19:
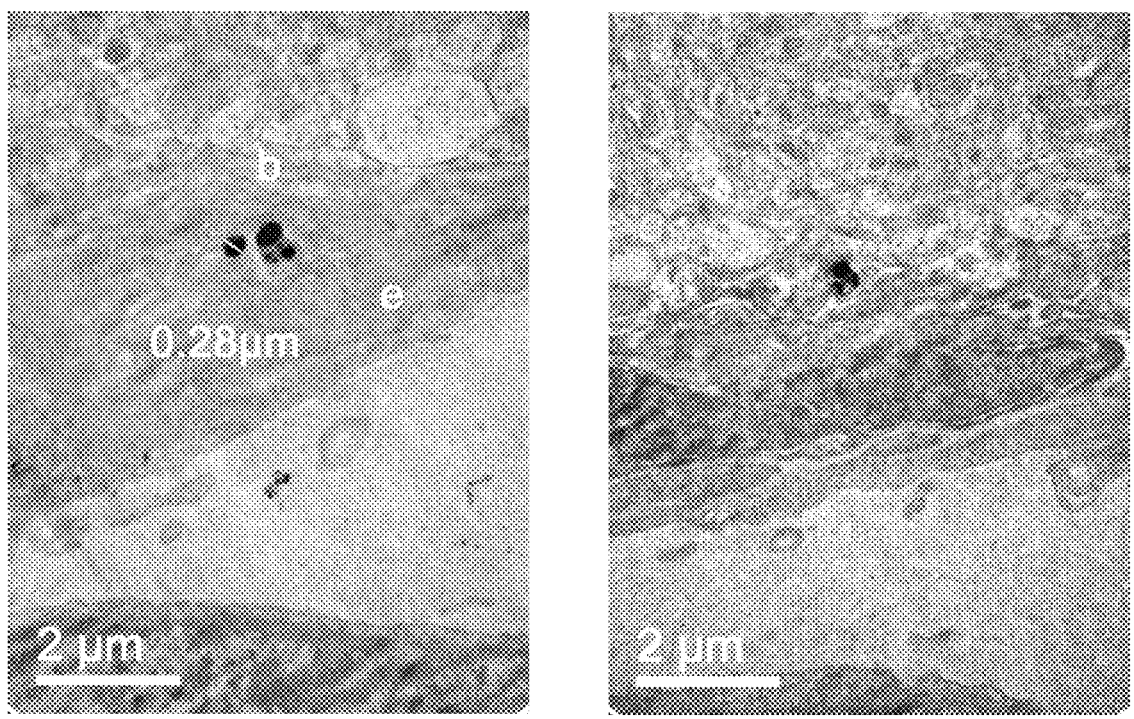
FIG. 19 Microphotographs obtained by transmission electronic microscopy of brain tissue samples from mice euthanatized 24 hours after the NLC administration by intravenous injection. The image shows a section of the epithelium that is part of the blood-brain barrier and several NLC diffusing across it are also appreciated.

To confirm that the NLC were distributed into the brain structures, a study of TEM microscopy was developed. FIG. 19 shows an example of the images obtained. The results confirm the capacity of the NLC to traverse the BBB. In the figure NLC going through the vascularized epithelium can be seen.

Figure 20:
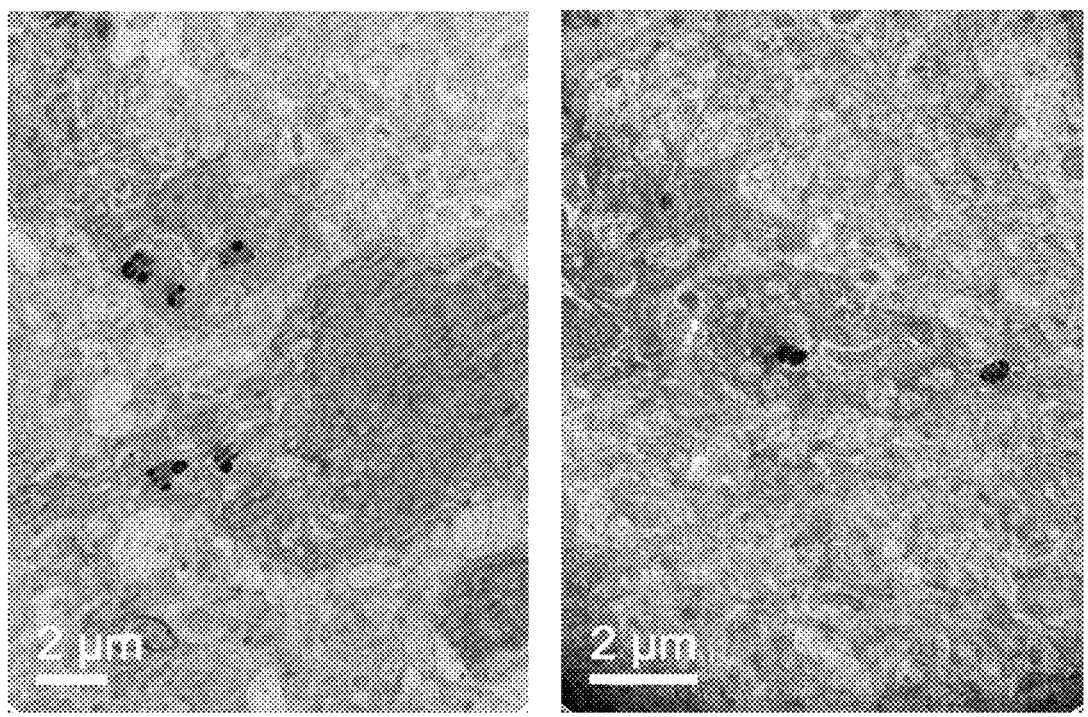
FIG. 20 Microphotographs obtained by transmission electronic microscopy of brain tissue samples from mice euthanatized 24 hours after the NLC administration by intravenous injection. In the image, astrocytes containing inside several NLC are shown.
Figure 22:
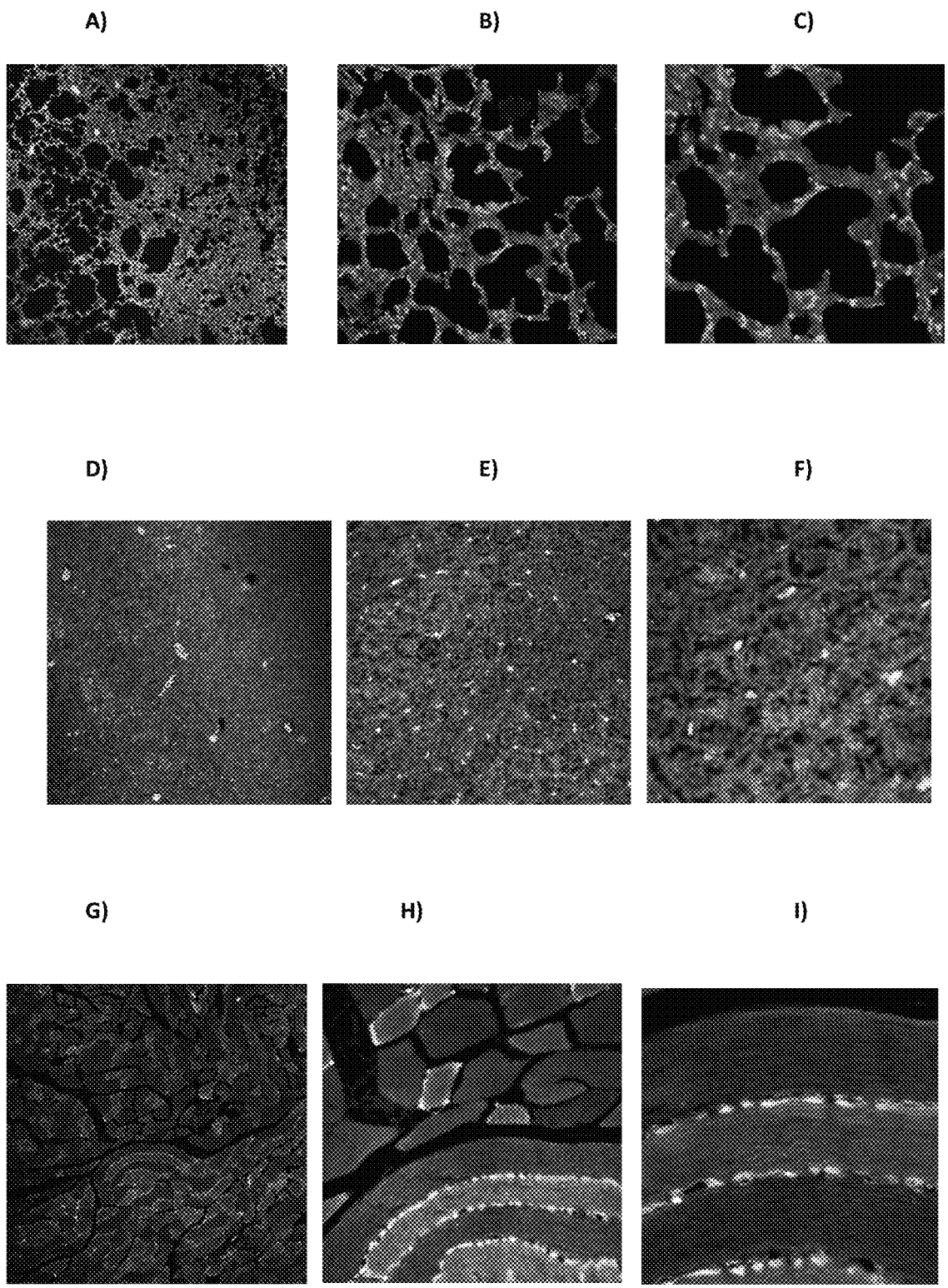
FIG. 22 Fluorescence confocal microscopy images of mouse tissue samples 24 hours after intravenous administration of the NCL to mice. A, B and C pictures correspond to lung samples at different magnifications (10×, 40× and C B×63). D, E and F: correspond to the liver (D×10, ×40 and ×100 F). G, H, I pictures are corresponding to muscle tissue (G×10, H 40× and I×63).

FIG. 20 shows a number of NLC in the interior of astrocytes and in FIG. 22 there are two images in which are clearly observed how NLC are localized in the cytoplasm of neurons.

Finally, and as an example, the FIG. 22 shows images obtained using confocal fluorescence microscopy of samples from different organs from mice in which is possible to distinguish the presence of NLC in all of them 24 hours after the intravenous administration. The letters A, B and C correspond to samples of lung were well distributed NLC in the tissue is appreciated. The letters D, E and F are corresponding to the liver, with numerous NLC well distributed all over the organ and the latest letters G, H, I are corresponding to images of muscle tissue that demonstrate that the administered NLC have also reached this tissue.

1.7. Ex Vivo Study of Regeneration of Cartilage by Stimulation of Elosulfase Alfa-Loaded NLC.

Human cartilage samples from knee surgery were treated with elosulfase alfa immobilized in NLC for 24 h. Several controls of cartilage samples were also assayed: non-treated tissue, elosulfase alone, and naïve NLC (empty). After this period of incubation time, protein were extracted from cultures and analyzed by proteomic techniques by a triple TOF 6600. The dose of NLC formulations was 50 ng/100 µl. Once the protein was extracted, the analysis was performed as follows:

Protein Identification by LC-MS/MS

An amount of 100 µg from each sample were loaded on a 10% SDS-PAGE gel. The protein band was detected by Sypro-Ruby fluorescent staining (Lonza, Switzerland), excised and processed by manual tryptic digestion as described elsewhere (Shevchenko et al., 1996). Peptides were extracted by carrying out three 20-min incubations in 40 µL of 60% acetonitrile dissolved in 0.5% HCOOH. The resulting peptide extracts were pooled, concentrated in a SpeedVac, and stored at −20° C.

Mass Spectrometric Analysis

Four µg of digested peptides were separated using Reverse Phase Chromatography. Gradient (micro liquid chromatography system; Eksigent Technologies nanoLC 400, SCIEX, coupled to high speed Triple TOF 6600 mass spectrometer (SCIEX) with a micro flow source). The analytical column used for analysis was a silica-based reversed phase column Chrom XP C18 150×0.30 mm, 3 mm particle size and 120 Å pore size (Eksigent, SCIEX). The trap column was a YMC-TRIART C18 (YMC Technologies, Teknokroma with a 3 mm particle size and 120 Å pore size, switched on-line with the analytical column. The loading pump delivered a solution of 0.1% formic acid in water at 10 µl/min. The micro-pump generated a flow-rate of 5 µl/min and was operated under gradient elution conditions, using 0.1% formic acid in water as mobile phase A, and 0.1% formic acid in acetonitrile as mobile phase B. Peptides were separated using a 90 minutes gradient ranging from 2% to 90% mobile phase B (mobile phase A: 2% acetonitrile, 0.1% formic acid; mobile phase B: 100% acetonitrile, 0.1% formic acid).

Data acquisition was performed using a TripleTOF 6600 System (SCIEX, Foster City, Calif.) using a Data dependent workflow. Source and interface conditions were the following: ionspray voltage floating (ISVF) 5500 V, curtain gas (CUR) 25, collision energy (CE) 10 and ion source gas 1 (GS1) 25. Instrument was operated with Analyst TF 1.7.1 software (SCIEX, USA). Switching criteria was set to ions greater than mass to charge ratio (m/z) 350 and smaller than m/z 1400 with charge state of 2-5, mass tolerance 250 ppm and an abundance threshold of more than 200 counts (cps). Former target ions were excluded for 15 s. The instrument was automatically calibrated every 4 hours using as external calibrant tryptic peptides from PepCalMix.

Data Analysis

Data files from MS/MS analysis were processed using ProteinPilot™ 5.0.1 software from Sciex (algorithm Paragon™ was used for database search and Progroup™ for data grouping). Data were searched using a Human specific Uniprot database. False discovery rate was performed using a non-lineal fitting method displaying only those results that reported a 1% global false discovery rate or better. (Shilov et al., 2007) Identified proteins of interest, see table below, were analyzed with Fun Rich software (http://www.funrich.org/). Protein-protein interactions were explored using the database on web resource (https://string-db.org/).

| Entry | Entry name | Protein names | Gene names | Organism |
|---|---|---|---|---|
| P13647 | K2C5_HUMAN | Keratin | KRT5 | Homo sapiens (Human) |
| P02679 | FIBG_HUMAN | Fibrinogen gamma chain | FGG PR02061 | Homo sapiens (Human) |
| P08133 | ANXA6_HUMAN | Annexin | ANXA6 ANX6 | Homo sapiens (Human) |
| P02538 | K2C6A_HUMAN | Keratin, | KRT6A K6A KRT6D | Homo sapiens (Human) |
| P08582 | TRFM_HUMAN | Melanotransferrin | MELTF MAP97 MFI2 | Homo sapiens (Human) |
| P09525 | ANXA4_HUMAN | Annexin A4 | ANXA4 ANX4 | Homo sapiens (Human) |
| P08779 | K1C16_HUMAN | Keratin | KRT16 KRT16A | Homo sapiens (Human) |
| P02671 | FIBA_HUMAN | Fibrinogen | FGA | Homo sapiens (Human) |
| P16403 | H12_HUMAN | Histone) | HIST1H1C H1F2 | Homo sapiens (Human) |
| P04004 | VTNC_HUMAN | Vitronectin | VTN | Homo sapiens (Human) |
| Q9Y240 | CLC11_HUMAN | C-type lectin domain family 11 member A | CLEC11A CLECSF3 LSLCL SCGF | Homo sapiens (Human) |
| P36955 | PEDF_HUMAN | Pigment epithelium-derived factor | SERPINF1 PEDF PIG35 | Homo sapiens (Human) |

-continued

| Entry | Entry name | Protein names | Gene names | Organism |
|---|---|---|---|---|
| Q04695 | K1C17_HUMAN | Keratin | KRT17 | Homo sapiens (Human) |
| P62987 | RL40_HUMAN | Ubiquitin-60S ribosomal protein L40 | UBA52 UBCEP2 | Homo sapiens (Human) |
| P08294 | SODE_HUMAN | Extracellular superoxide dismutase | SOD3 | Homo sapiens (Human) |
| P02771 | FETA_HUMAN | Alpha-fetoprotein | AFP HPAFP | Homo sapiens (Human) |
| P02788 | TRFL_HUMAN | Lactotransferrin | LTF GIG12 LF | Homo sapiens (Human) |
| P08493 | MGP_HUMAN | Matrix Gla protein | MGP MGLAP GIG36 | Homo sapiens (Human) |
| P06727 | APOA4_HUMAN | Apolipoprotein A-IV | APOA4 | Homo sapiens (Human) |
| P61626 | LYSC_HUMAN | Lysozyme C | LYZ LZM | Homo sapiens (Human) |
| P35613 | BASI_HUMAN | BSG | UNQ6505/PRO21383 | Homo sapiens (Human) |
| P01009 | A1AT_HUMAN | Alpha-1-antitrypsin (Alpha-1 protease inhibitor) (Alpha-1-antiproteinase) (Serpin A1) [Cleaved into: Short peptide from AAT (SPAAT) | SERPINA1 AAT PI PR00684 PR02209 | Homo sapiens (Human) |
| P02649 | APOE_HUMAN | Apolipoprotein E (Apo-E) | APOE | Homo sapiens (Human) |
| P10451 | OSTP_HUMAN | Osteopontin | SPP1 BNSP OPN P5EC0156 | Homo sapiens (Human) |
| Q9Y639 | NPTN_HUMAN | Neuroplastin | NPTN SDFR1 SDR1 | Homo sapiens (Human) |
| P13646 | K1C13_HUMAN | Keratin | KRT13 | Homo sapiens (Human) |
| Q9BYJ0 | FGFP2_HUMAN | Fibroblast growth factor-binding protein 2 | FGFBP2 K5P37 UNQ425/PRO1065 | Homo sapiens (Human) |
| Q07507 | DERM_HUMAN | Dermatopontin | DPT | Homo sapiens (Human) |
| P81605 | DCD_HUMAN | Dermcidin | DCD AIDD DSEP | Homo sapiens (Human) |
| P06756 | ITAV_HUMAN | Integrin alpha-V | ITGAV MSK8 VNRA VTNR | Homo sapiens (Human) |
| P02774 | VTDB_HUMAN | Vitamin D-binding protein | GC | Homo sapiens (Human) |
| P12111 | CO6A3_HUMAN | Collagen alpha-3 | COL6A3 | Homo sapiens (Human) |
| P02751 | FINC_HUMAN | Fibronectin (EN) | FN1 FN | Homo sapiens (Human) |
| P04264 | K2C1_HUMAN | Keratin, type II cytoskeletal 1 | KRT1 KRTA | Homo sapiens (Human) |
| P35527 | K1C9_HUMAN | Keratin, type I cytoskeletal 9 | KRT9 | Homo sapiens (Human) |
| P12109 | CO6A1_HUMAN | Collagen alpha-1 | COL6A1 | Homo sapiens (Human) |

| Entry | Entry name | Protein names | Gene names | Organism |
|---|---|---|---|---|
| P49747 | COMP_HUMAN | Cartilage oligomeric matrix protein | COMP | Homo sapiens (Human) |
| P13645 | K1C10_HUMAN | Keratin, type I cytoskeletal 10 | KRT10 KPP | Homo sapiens (Human) |
| P35908 | K22E_HUMAN | Keratin, type II cytoskeletal 2 epidermal | KRT2 KRT2A KRT2E | Homo sapiens (Human) |
| P12110 | CO6A2_HUMAN | Collagen alpha-2 | COL6A2 | Homo sapiens (Human) |
| P51888 | PRELP_HUMAN | Prolargin | PRELP SLRR2A | Homo sapiens (Human) |
| P07355 | ANXA2_HUMAN | Annexin A2 | ANXA2 ANX2 ANX2L4 CAL1H LPC2D | Homo sapiens (Human) |
| O75339 | CILP1_HUMAN | Cartilage intermediate layer protein 1 | HCILP UNQ602/PRO1188 | omo sapiens (Human) |
| Q08431 | MFGM_HUMAN | Lactadherin | MFGE8 | Homo sapiens (Human) |
| P07585 | PGS2_HUMAN | Decorin | DCN SLRR1B | Homo sapiens (Human) |
| PO2768 | ALBU_HUMAN | Serum albumin | ALB GIG20 GIG42 PRO0903 PRO1708 PRO2044 PRO2619 PRO2675 UNQ696/PRO1341 | Homo sapiens (Human) |
| P10915 | HPLN1_HUMAN | Hyaluronan and proteoglycan link protein 1 | HAPLN1 CRTL1 | Homo sapiens (Human) |
| Q15582 | BGH3_HUMAN | Transforming growth factor-beta-induced protein ig-h3 protein) (RGD-CAP) | TGFBI BIGH3 | Homo sapiens (Human) |
| P21810 | PGS1_HUMAN | Biglycan | BGN SLRR1A | Homo sapiens (Human) |
| P16112 | PGCA_HUMAN | Aggrecan core protein | ACAN AGC1 CSPG1 MSK16 | Homo sapiens (Human) |
| P08758 | ANXA5_HUMAN | Annexin A5 | ANXA5 ANX5 ENX2 PP4 | Homo sapiens (Human) |
| P08670 | VIME_HUMAN | Vimentin | VIM | Homo sapiens (Human) |
| P02533 | K1C14_HUMAN | Keratin, type I cytoskeletal 14 | KRT14 | Homo sapiens (Human) |
| O15335 | CHAD_HUMAN | Chondroadherin | CHAD SLRR4A | Homo sapiens (Human) |
| P04083 | ANXA1_HUMAN | Annexin Al | ANXA1 ANX1 LPC1 | Homo sapiens (Human) |
| Q8IUL8 | CILP2_HUMAN | Cartilage intermediate layer protein 2 | CILP2 | Homo sapiens (Human) |
| P20774 | MIME_HUMAN | Mimecan | OGN OIF SLRR3A | Homo sapiens (Human) |
| P10909 | CLUS_HUMAN | Clusterin | CLU APOJ CLI KUB1 AAG4 | Homo sapiens (Human) |
| Q06828 | FMOD_HUMAN | Fibromodulin | FMOD FM SLRR2E | Homo sapiens (Human) |
| P51884 | LUM_HUMAN | Lumican | LUM LDC SLRR2D | Homo sapiens (Human) |

| Entry | Entry name | Protein names | Gene names | Organism |
| --- | --- | --- | --- | --- |
| P06733 | ENOA_HUMAN | Alpha-enolase | ENO1 ENO1L1 MBPB1 MPB1 | Homo sapiens (Human) |
| P68871 | HBB_HUMAN | Hemoglobin subunit beta | HBB | Homo sapiens (Human) |
| O60687 | SRPX2_HUMAN | Sushi repeat-containing protein SRPX2 | SRPX2 SRPUL | Homo sapiens (Human) |
| O43854 | EDIL3_HUMAN | EGF-like repeat and discoidin l-like domain-containing protein 3 | EDIL3 DEL1 | Homo sapiens (Human) |
| P60174 | TPIS_HUMAN | Triosephosphate isomerase | TPI1 TPI | Homo sapiens (Human) |
| P07996 | TSP1_HUMAN | Thrombospondin-1 | THBS1 TSP TSP1 | Homo sapiens (Human) |
| P63261 | ACTG_HUMAN | Actin, cytoplasmic 2 | ACTG1 ACTG | Homo sapiens (Human) |
| P69905 | HBA_HUMAN | Hemoglobin subunit alpha | HBA1; HBA2 | Homo sapiens (Human) |
| Q9BXN1 | ASPN_HUMAN | Asporin | ASPN PLAP1 SLRR1C UNQ215/PRO241 | Homo sapiens (Human) |
| P04406 | G3P_HUMAN | Glyceraldehyde-3-phosphate dehydrogenase | GAPDH GAPD CDABP0047 OK/SW-cl.12 | Homo sapiens (Human) |
| P21589 | 5NTD_HUMAN | 5'-nucleotidase (5'-NT) | NT5E NT5 NTE | Homo sapiens (Human) |
| P00338 | LDHA_HUMAN | L-lactate dehydrogenase A | LDHA PIG19 | Homo sapiens (Human) |
| P00558 | PGK1_HUMAN | Phosphoglycerate kinase 1 | PGK1 PGKA MIG10 OK/SW-cl.110 | Homo sapiens (Human) |
| P08123 | CO1A2_HUMAN | Collagen alpha-2 | COL1A2 | Homo sapiens (Human) |
| Q06830 | PRDX1_HUMAN | Peroxiredoxin-1 | PRDX1 PAGA PAGB TDPX2 | Homo sapiens (Human) |
| Q5VTE0 | EF1A3_HUMAN | Putative elongation factor 1-alpha-like 3 | EEF1A1P5 EEF1AL3 | Homo sapiens (Human) |
| P02458 | CO2A1_HUMAN | Collagen alpha-1 | COL2A1 | Homo sapiens (Human) |
| P06396 | GELS_HUMAN | Gelsolin (AGEL) | GSN | Homo sapiens (Human) |
| P02545 | LMNA_HUMAN | Prelamin-A/C | LMNA LMN1 | Homo sapiens (Human) |
| P62805 | H4_HUMAN | Histone H4 | HIST1H4A H4/A H4FA; HIST1H4B H4/I H4FI; HIST1H4C H4/G H4FG; HIST1H4D H4/B H4FB; HIST1H4E H4/J H4FJ; HIST1H4F H4/C H4FC; HIST1H4H H4/H H4FH; HIST1H4I H4/M H4FM; HIST1H4J H4/E H4FE; HIST1H4K H4/D H4FD; HIST1H4L H4/K H4FK; HIST2H4A H4/N H4F2 H4FN HIST2H4; HIST2H4B H4/O H4FO; HIST4H4 | Homo sapiens (Human) |
| P02647 | APOA1_HUMAN | Apolipoprotein A-I | AP0A1 | Homo sapiens (Human) |

-continued

| Entry | Entry name | Protein names | Gene names | Organism |
|---|---|---|---|---|
| P02765 | FETUA_HUMAN | Alpha-2-HS-glycoprotein | AHSG FETUA PRO2743 | Homo sapiens (Human) |
| Q9BQE3 | TBA1C_HUMAN | Tubulin alpha-1C | TUBA1C TUBA6 | Homo sapiens (Human) |
| P14618 | KPYM_HUMAN | Pyruvate kinase PKM | PKM OIP3 PK2 PK3 PKM2 | Homo sapiens (Human) |
| O75596 | CLC3A_HUMAN | C-type lectin domain family 3 member A | CLEC3A CLECSF1 UNQ700/PRO1345 | Homo sapiens (Human) |
| P02452 | CO1A1_HUMAN | Collagen alpha-1 | COL1A1 | Homo sapiens (Human) |
| P02042 | HBD_HUMAN | Hemoglobin subunit delta | HBD | Homo sapiens (Human) |
| Q71DI3 | H32_HUMAN | Histone H3.2 | HIST2H3A; HIST2H3C H3F2 H3FM; HIST2H3D | Homo sapiens (Human) |
| Q99983 | OMD_HUMAN | Osteomodulin | OMD SLRR2C UNQ190/PRO216 | Homo sapiens (Human) |
| P24821 | TENA_HUMAN | Tenascin (TN) | TNC HXB | Homo sapiens (Human) |
| Q7Z7G0 | TARSH_HUMAN | Target of Nesh-SH3 | ABI3BP NESHBP TARSH | Homo sapiens (Human) |
| P07237 | PDIA1_HUMAN | Protein disulfide-isomerase | P4HB ERBA2L PDI PDIA1 PO4DB | Homo sapiens (Human) |
| O15232 | MATN3_HUMAN | Matrilin-3 | MATN3 | Homo sapiens (Human) |
| Q92743 | HTRA1_HUMAN | Serine protease HTRA1 | HTRA1 HTRA PRSS11 | Homo sapiens (Human) |
| P29353 | SHC1_HUMAN | SHC-transforming protein 1 | SHC1 SHC SHCA | Homo sapiens (Human) |
| Q9BTM1 | H2AJ_HUMAN | Histone H2A.J | H2AFJ | Homo sapiens (Human) |
| P06576 | ATPB_HUMAN | ATP synthase subunit beta, mitochondrial | ATP5F1B ATP5B ATPMB ATPSB | Homo sapiens (Human) |
| P34059 | GALNS_HUMAN | N-acetylgalactosamine-6-sulfatase (EC 3.1.6.4) | GALNS | Homo sapiens (Human) |
| P00915 | CAH1_HUMAN | Carbonic anhydrase 1 | CA1 | Homo sapiens (Human) |
| Q99879 | H2B1M_HUMAN | Histone H2B type 1-M | HIST1H2BM H2BFE | Homo sapiens (Human) |
| P32119 | PRDX2_HUMAN | Peroxiredoxin-2 | PRDX2 NKEFB TDPX1 | Homo sapiens (Human) |
| P04075 | ALDOA_HUMAN | Fructose-bisphosphate aldolase A | ALDOA ALDA | Homo sapiens (Human) |
| P02652 | APOA2_HUMAN | Apolipoprotein A-II | APOA2 | Homo sapiens (Human) |
| P36957 | ODO2_HUMAN | Dihydrolipoyllysine-residue succinyltransferase component of 2-oxoglutarate dehydrogenase complex, mitochondrial | DLST DLTS | Homo sapiens (Human) |

| Entry | Entry name | Protein names | Gene names | Organism |
|---|---|---|---|---|
| P02461 | CO3A1_HUMAN | Collagen alpha-1 | COL3A1 | Homo sapiens (Human) |

Figure 35:
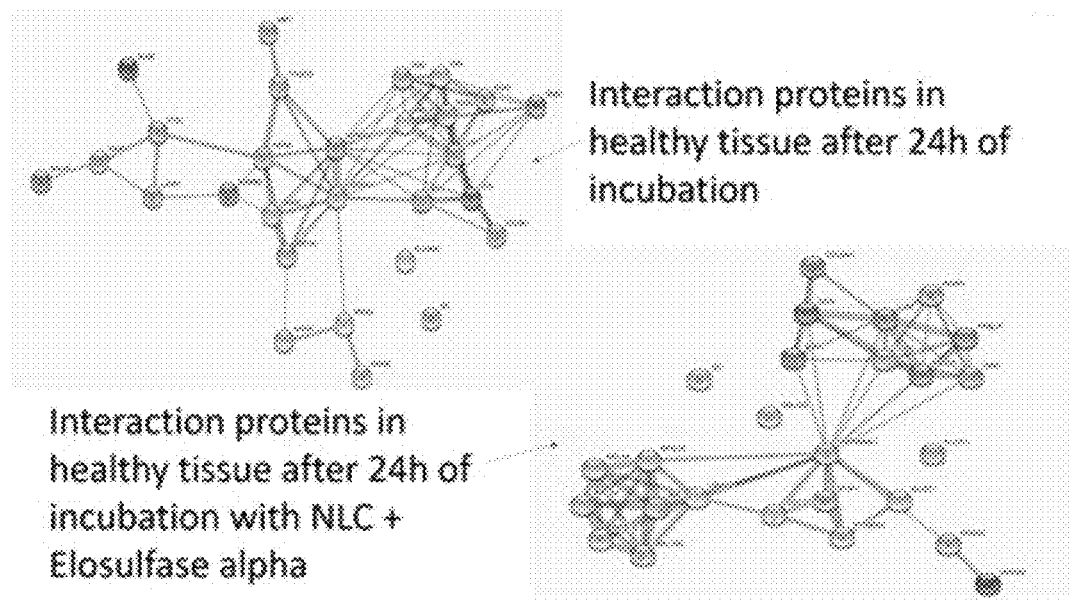
FIG. 35. Comparison of protein interactions of non-treated healthy cartilage tissue with treated cartilage by 24 h-incubation with NLC loaded with elosulfase alfa.

From the comparison of the different treatment of the cartilage samples, proteins related to keratan sulphate (the glycosaminoglycan of special relevance in the physiological development of the cartilage matrix) were identified with a 99% reliability of the presence of these proteins, generating through the afore mentioned program "String". The protein-protein interactions (represented by arrow and cycles where the name the proteins are show near cycles) are displayed in FIG. 35, represented as the lines that are crossed where the connection between proteins are found (balls). As can be seen, only the protein-protein interaction in treated samples with elosulfase alfa loaded-NLC are relevant in case of keratan sulfate expression, even when compared with the samples treated with free elosulfase alfa, see below table.

The NLC formulation was stained with a fluorescent probe, DID' (DilC$_{18}$(5) solid (1,1'-dioctadecyl-3,3,3',3'-tetramethylindodicarbocyanine, 4-chlorobenzenesulfonate salt), and dispersed at a concentration of 200 mg/ml in saline solution with 1% sodium taurocholate.

Formulations were administered via subcutaneous route (150 μl) at the lumbar region of three rats (Sprague Dawley; males; 300-330 mg). After 24 h, the animals were euthanatized with $CO_2$ and the organs and tissues were removed for examination under confocal fluorescence microscopy.

Figure 36:
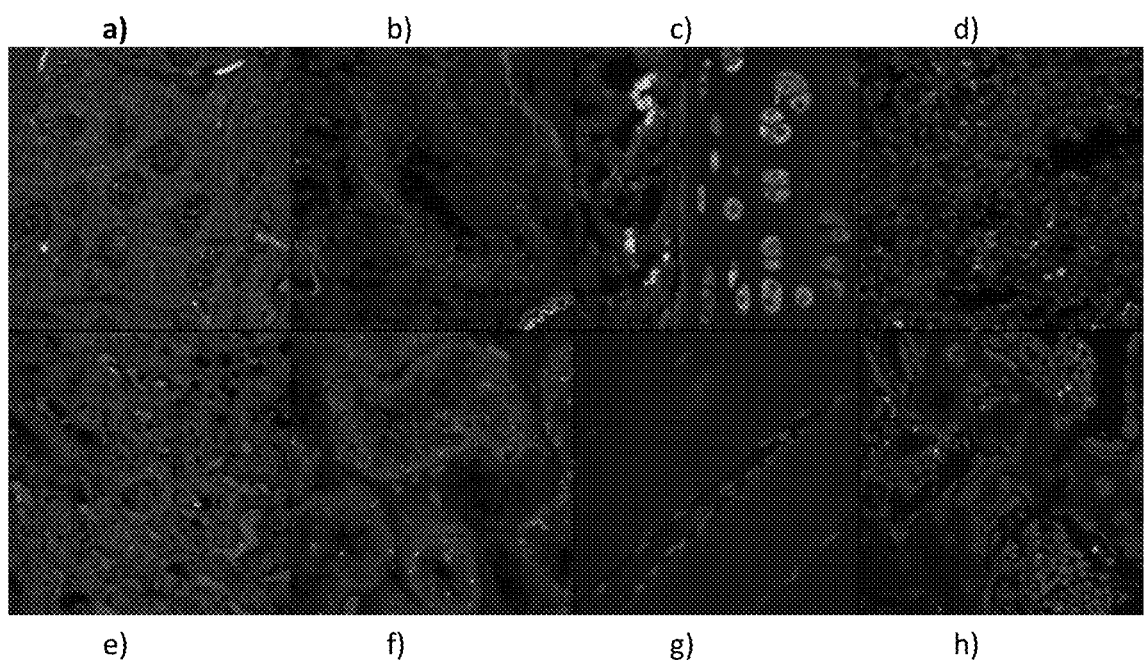
FIG. 36. Confocal fluorescence microscopy showing (in red) the presence of NLC formulations in different organs and tissues after 24 h of subcutaneous administration. a) brain, b) lung, c) rib, d) liver, e) spleen, f) kidney, g) skeletal muscle and h) bone.
Figure 37:
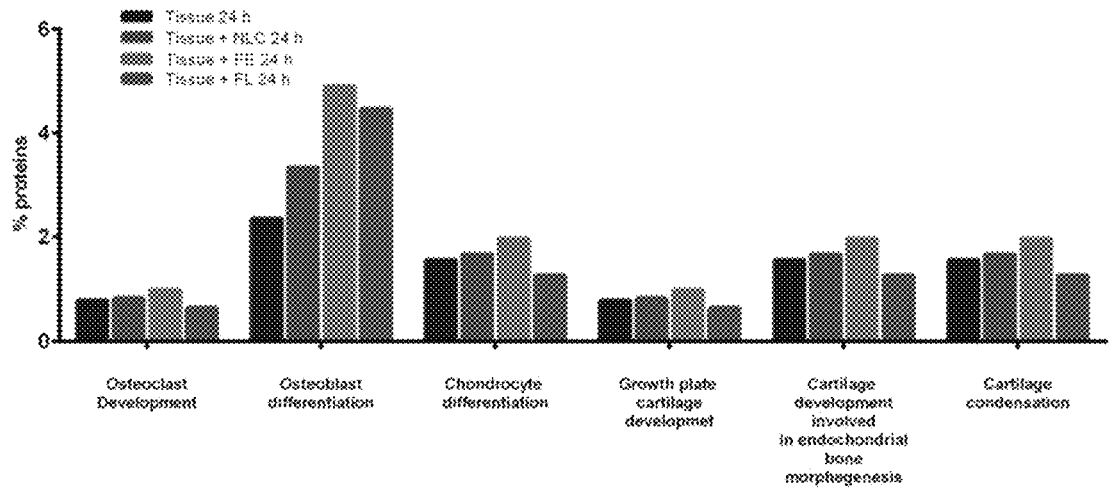
FIG. 37. These figures show that encapsulated alpha elosulfase aids regenerating cartilage and bone, in particular these figure illustrate studies of proteins made in cartilage of healthy patients and pathological cells of fibroblasts finding similarity of proteins in the different cells for these functions.
Figure 37:
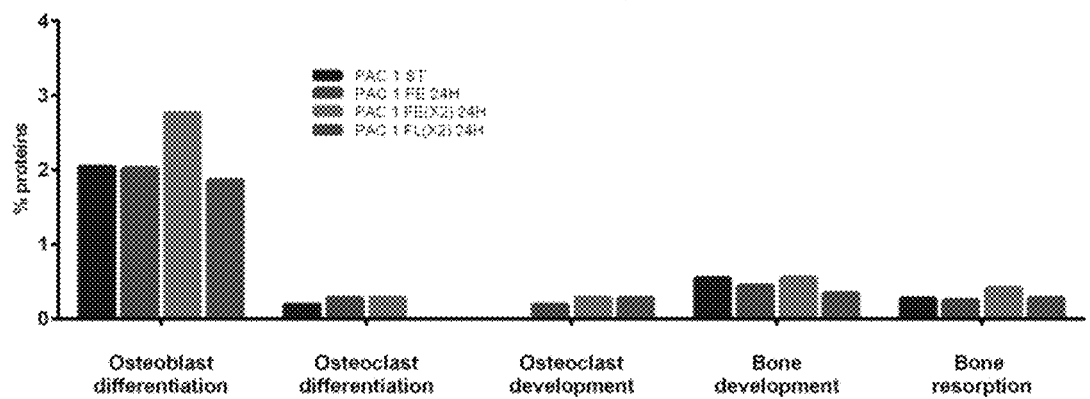
Figure 38:
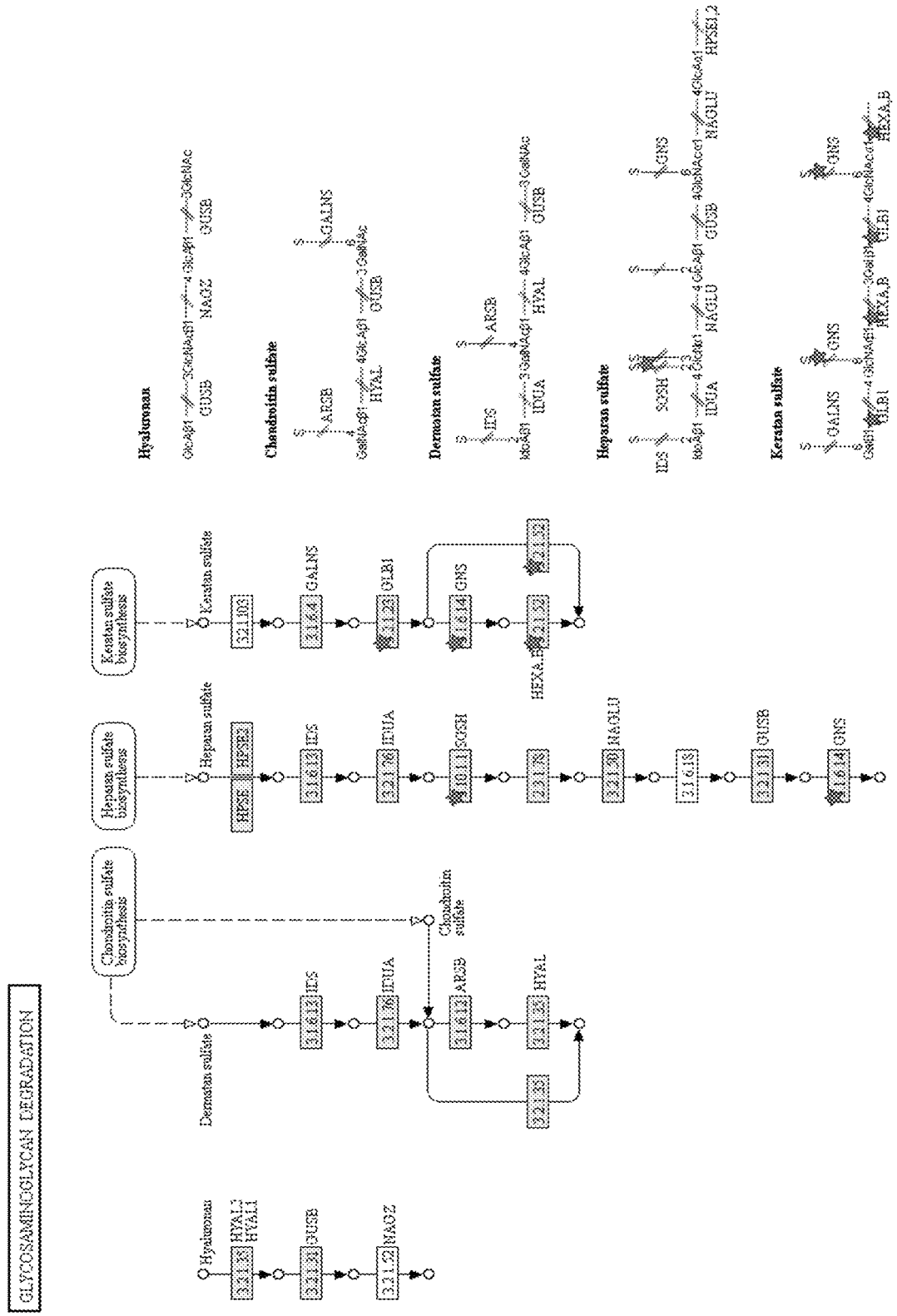
FIG. 38. Metabolic pathway where the regeneration of the route can be seen once the NLCs are incorporated with elosulfase alfa (image above without treatment, below image with treatment with NLC+elosulfase alfa).
Figure 38:
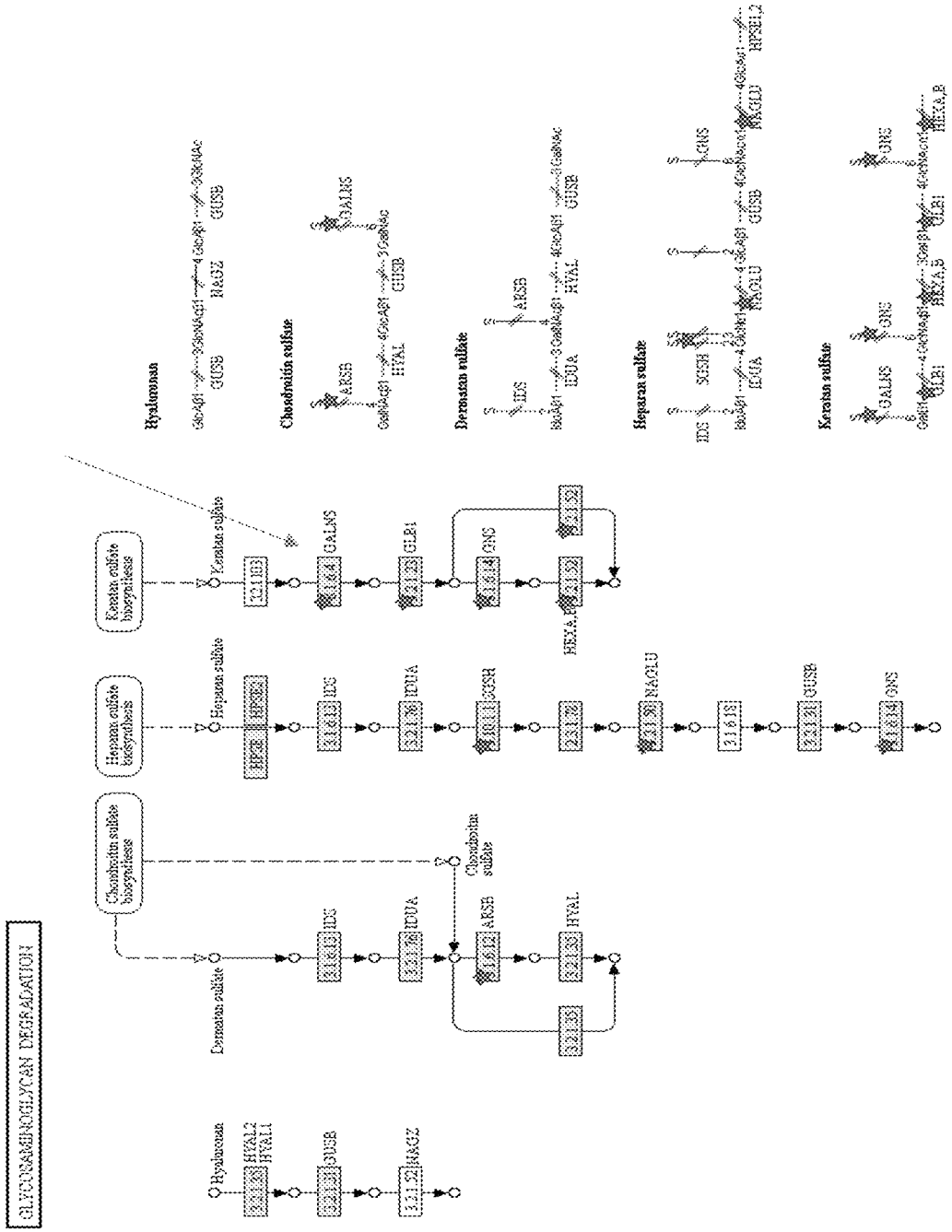

Confocal images (FIG. 36) of all analyzed tissues showed the presence of NLC formulations, including the lung, rib,

| Entry | Entry name | Protein names | Gene names | Organism |
|---|---|---|---|---|
| P51888 | PRELP_HUMAN | Prolargin | PRELP SLRR2A | Homo sapiens (Human) |
| P16112 | PGCA_HUMAN | Aggrecan | ACAN AGC1 CSPG1 MSK16 | Homo sapiens (Human) |
| P20774 | MIME_HUMAN | Mimecan | OGN OIF SLRR3A | Homo sapiens (Human) |
| Q06828 | FMOD_HUMAN | Fibromodulin | FMOD FM SLRR2E | Homo sapiens (Human) |
| P51884 | LUM_HUMAN | Lumican | LUM LDC SLRR2D | Homo sapiens (Human) |
| Q99983 | OMD_HUMAN | Osteomodulin | OMD SLRR2C UNQ190/PRO216 | Homo sapiens (Human) |
| P34059 | GALNS_HUMAN | N-acetylgalactosamine-6-sulfatase | GALNS | Homo sapiens (Human) |

In FIG. 35 it is shown the up-regulated function of ribosome stimulation related to the biosynthesis of proteoglycans of keratan sulfate after the co-incubation of elosulfase alfa-loaded NLC. This result confirmed the ability of immobilized elosulfase alfa to increase the expression of proteins involved in the regeneration of matrix cartilage. Also, it has been demonstrated that NLC enable the elosulfase alfa to enter the cells and to stimulate the proteins that normally are expressed in the matrix of the cartilage tissue.

1.8. Study of Subcutaneous Administration of NLC Formulations.

The subcutaneous administration of elosulfase alfa-loaded NLC formulations in rats was assessed by incorporating different surfactants (bile salts, deoxicholate, taurocholate, glycocholate, hiodeoxycholate, litocholate), lecitins (soy, egg, corn, sunflower), poloxamers (188, 407). All of them were used in different concentrations ranged between 0.5-2% wt/total volume to be administered. The best results in obtaining a stable homogeneous suspension were achieved with sodium taurocholate (1% in saline solution). The size of NLC after resuspension in sodium taurocholate was checked to remained in the range between 300-400 nm.

kidney, spleen, muscle and central nervous samples, thereby, confirming NLC were widely distributed through the whole organism.

The invention claimed is:

1. A lipid nanostructured system which comprises nanoparticles which in turn comprise:
   a. a gelled core comprising an aqueous dissolution, solution or dispersion comprising a temperature responsive polymer that becomes a gel as a function of the temperature, and which further comprises one or more enzymes or other proteins immobilized in the core;
   b. a lipid layer coating the inner core comprising a mixture of:
      i. a solid lipid, which is solid or waxy at 25° C. and a pressure of 1 atm, comprising fatty acids, with a fusion process that begins at temperatures above 35° C., as determined by differential scanning calorimetry (DSC), with a hydrophilic-lipophilic balance (HLB) value lower than 10 and densities between 0.8 and 1 g/cm$^3$, or a mixture of the solid lipids, and
      ii. a liquid lipid which behaves as a liquid at 25° C. and a pressure of 1 atm, constituted by fatty acids with a fusion process that begins at temperatures below 30° C., as determined by differential scanning calorimetry (DSC), and densities ranging from 0.88 to 0.97 g/cm³, where the mixture of liquid lipid and solid lipid presents a fusion process that begins at temperatures between 20° C. and below 50° C. as determined by differential scanning calorimetry (DSC), wherein the solid lipid and liquid lipid are mixed in a ratio of liquid lipid to solid lipid of 98:2 to 1:99%, wherein the ratio is expressed as a percentage by weight of solid lipid and liquid lipid with respect to the total lipid composition of the lipid layer coating the inner core;

wherein the lipid layer also comprises lipid soluble or dispersible surfactants; wherein the lipid soluble or lipid dispersible surfactants, are selected from molecules surface-active with HLB values lower than 10; and c. a pegylated coating of the lipid layer that also comprises water soluble or water dispersible surfactants, wherein said pegylated coating comprises polyethylene glycol (PEG), or PEG esters, and the water soluble or water dispersible surfactants have a HLB greater than 10.

2. The lipid system of claim 1, wherein fatty acids of the lipid layer comprise the following formula:

$$C:D\ n-x,$$

wherein:
C represents the number of carbon atoms of the fatty acid;
D is the number of double bonds in the fatty acid;
n is the position of a distal double bond, where n is the total number of carbons and x a number provided by the position, and wherein any multiple double bonds are separated by a methylene group;

wherein the solid lipid is selected from the group consisting of:
a. saturated fatty acids that have values of $C \geq 12$ and $C < 41$ and $D=0$;
b. unsaturated and polyunsaturated trans fatty acids with values of $C > 17$y $C < 25$, $D \geq 1$, x between 1 and n–2;
c. monoesters of fatty acids saturated with values of $C \geq 14$ and $C < 41$ and $D=0$ with sorbitan, polyoxyethylene, polioxietilensorbitano, glycerine or diethylene glycol;
d. triesters formed between glycerol and fatty acids saturated with values of $C \geq 3$ and $C < 41$ and $D=0$;
e. triesters formed between glycerol and trans unsaturated fatty acids; and
f. any combination thereof; and wherein the liquid lipid is selected from the group consisting of:
a. saturated fatty acids that have values of $C \geq 3$ and $C \leq 11$ and $D=0$;
b. unsaturated and polyunsaturated cis acid fatty with values of $C \geq 3$ and $C \leq 23$, $D \geq 1$, x between 1 and n–2;
c. monoesters of fatty acids saturated with values of $C \geq 3$ and $C < 14$ y $D=0$ with sorbitan, polyoxyethylene, polyoxyethylensorbitane, glycerin or diethylene glycol;
d. triesters formed between glycerol and fatty acids saturated with values of $C < 3$ and $D=0$
e. triesters formed between glycerin and unsaturated cis fatty acids with values of $C \geq 3$ y $C \leq 23$, $D \geq 1$, x between 1 and n–2; and
f. any combination thereof.

3. The lipid system of claim 1, where the lipid layer is made of a mixture of solid and liquid lipids in a ratio between 30:70 and 50:50, and wherein the mixture presents a fusion process that starts at temperatures between 30 and 40° C., as determined by differential scanning calorimetry (DSC).

4. The lipid system of claim 1, wherein the lipid layer is made up of a mixture of solid and liquid lipids in a ratio between 35:65 and 45:55, and the mixture has a fusion process that begins at temperatures between 35 and 40° C., as determined by differential scanning calorimetry (DSC).

5. The lipid system of claim 1, where the dissolution solution, or dispersion of aqueous nature of the core comprises a temperature responsive polymer selected from the group consisting of: poloxamer 407, Chitosan, hydroxypropyl cellulose (HPC), hydroxypropylmethyl cellulose (HPMC) and diblock copolymer of polyethylene glycol and polylactic acid (PLGA-PEG-PEG).

6. The lipid system of claim 1 wherein the gelled core comprises one or more enzymes selected from group list consisting of: elosulfase alfa, velaglucerase, laronidase, idursulfase, galsulfase, imiglucerase, agalsidase, sebelipase alfa, cerliponase alfa, velmanase and alglucosidase, immobilized in the core.

7. The lipid system of claim 1, where the solid lipid is selected from the group consisting of: glyceryl disterate, glyceryl palmitosterate, trimyristin, tristearin, cholesterol, soy lecithin, egg lecithin, sunflower lecithin and corn lecithin; and the liquid lipid is selected from the group consisting of: olive oil and triglycerides of caprilic and capric acids.

8. The lipid system of claim 1, wherein the lipid layer is made of a mixture of glyceryl disterate or glycerol palmitate in an amount ranging from 5-20%, with trimyristin in an amount between 5-20%, tristearin in an amount between 5-20%, and cholesterol in an amount between 2-10%, as solid components, and soy lecithin and a blend of liquid components comprising olive oil in an amount between 30-70%, and triglycerides of caprilic and capric acids in an amount between a 10-20%, wherein the percentage of each component, refers to its proportion in weight/weight percentage with respect to the total amount of lipids that form the layer.

9. The lipid system of claim 1, wherein the lipid layer is made of a mixture of dibehenate of glyceryl in an amount ranging from 5-20%, with trimyristin in an amount between 5-20%, tristearin in an amount between 5-20%, and cholesterol in an amount between 2-10% as solid components and egg lecithin or soy lecithin, and a blend of liquid lipid as olive oil, cod liver oil or sunflower oil in an amount between 30-70% and triglycerides of caprilic and capric acids in an amount between a 10-20%, wherein % refers to weight/weight percentage of each component related to the total amount of lipids forming the layer.

10. The lipid system of claim 1, wherein the lipid layer that coats the aqueous core is formed by mixtures of the following solid and liquid lipids: glyceryl dibehenate, glyceryl, Tristearin, Trimyristine, Cholesterol, olive oil, triglycerides of caprylic and capric acid and liquid soy lecithin.

11. The lipid system of claim 1, wherein the gelled core comprises one or more proteins with activity on cellular metabolism selected from the group consisting of infliximab, abatacerpt, rituximab, adalidumab, etanercept, golimumab, certolizumab, sifalimumab, and anifrolumab, immobilized in the core.

12. A method for delivering an enzyme or protein for therapy of a subject in need thereof, comprising administering the nanostructured lipid system of claim 1 to the subject.

13. A method for the treatment or prevention of the degeneration of the cartilage or bone or for treatment of a lysosomal storage disease, comprising administering the nanostructured lipid system of claim 1 to a subject in need thereof.

* * * * *